(12) United States Patent
Schumm et al.

(10) Patent No.: US 9,310,304 B2
(45) Date of Patent: Apr. 12, 2016

(54) METHODS AND COMPOSITIONS FOR RAPID MULTIPLEX AMPLIFICATION OF STR LOCI

(75) Inventors: James W. Schumm, Lakewood Ranch, FL (US); Richard F. Selden, Lincoln, MA (US); Eugene Tan, Arlington, MA (US)

(73) Assignee: NetBio, Inc., Waltham, MA (US)

( * ) Notice: Subject to any disclaimer, the term of this patent is extended or adjusted under 35 U.S.C. 154(b) by 0 days.

(21) Appl. No.: 13/469,971

(22) Filed: May 11, 2012

(65) Prior Publication Data

US 2012/0309637 A1 Dec. 6, 2012

Related U.S. Application Data

(60) Provisional application No. 61/485,459, filed on May 12, 2011.

(51) Int. Cl.
- *C12Q 1/68* (2006.01)
- *G01N 21/64* (2006.01)
- *C07H 21/04* (2006.01)

(52) U.S. Cl.
CPC ............ *G01N 21/6486* (2013.01); *C07H 21/04* (2013.01); *C12Q 1/6876* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 2,817,264 A | 12/1957 | Pearson | |
| 4,832,815 A | 5/1989 | Kambara et al. | |
| 4,855,225 A | 8/1989 | Fung et al. | |
| 4,865,707 A | 9/1989 | Karger | |
| 4,881,812 A | 11/1989 | Ohkubo et al. | |
| 4,945,135 A | 7/1990 | Grubbs | |
| 5,112,460 A | 5/1992 | Karger | |
| 5,198,511 A | 3/1993 | Brown-Wensley | |
| 5,208,466 A | 5/1993 | Pentoney | |
| 5,234,809 A | 8/1993 | Boom et al. | |
| 5,273,638 A | 12/1993 | Konrad et al. | |
| 5,275,710 A | 1/1994 | Gombocz et al. | |
| 5,307,148 A | 4/1994 | Kambara et al. | |
| 5,312,940 A | 5/1994 | Grubbs | |
| 5,332,666 A | 7/1994 | Prober et al. | |
| 5,334,424 A | 8/1994 | Hani | |
| 5,342,909 A | 8/1994 | Grubbs | |
| 5,462,995 A | 10/1995 | Hosaka | |
| 5,545,901 A | 8/1996 | Pentoney et al. | |
| 5,561,208 A | 10/1996 | Takahashi | |
| 5,614,726 A | 3/1997 | Wilbur | |
| 5,663,129 A | 9/1997 | Emert | |
| 5,800,996 A | 9/1998 | Lee et al. | |
| 5,840,338 A | 11/1998 | Roos | |
| 5,847,162 A | 12/1998 | Lee et al. | |
| 5,876,675 A | 3/1999 | Kennedy | |
| 5,976,336 A | 11/1999 | Dubrow | |
| 5,981,956 A | 11/1999 | Stern | |
| 6,017,434 A | 1/2000 | Simpson et al. | |
| 6,017,765 A | 1/2000 | Yamada et al. | |
| 6,100,541 A | 8/2000 | Nagle | |
| 6,131,072 A | 10/2000 | Holden et al. | |
| 6,150,180 A | 11/2000 | Parce | |
| 6,156,181 A | 12/2000 | Parce | |
| 6,167,910 B1 | 1/2001 | Chow | |
| 6,211,955 B1 | 4/2001 | Basiji et al. | |
| 6,224,732 B1 | 5/2001 | Imasaka et al. | |
| 6,225,635 B1 | 5/2001 | Brewer | |
| 6,225,636 B1 | 5/2001 | Ginestet | |
| 6,226,635 B1 | 5/2001 | Laurence et al. | |
| 6,316,781 B1 | 11/2001 | Nagle | |
| 6,321,791 B1 | 11/2001 | Chow | |
| 6,329,661 B1 | 12/2001 | Perov | |
| 6,358,387 B1 | 3/2002 | Kopf | |
| 6,361,672 B1 | 3/2002 | Zhu et al. | |
| 6,391,541 B1 | 5/2002 | Petersen et al. | |
| 6,407,395 B1 | 6/2002 | Perov | |
| 6,409,900 B1 | 6/2002 | Parce | |
| 6,413,782 B1 | 7/2002 | Parce | |
| 6,431,476 B1 | 8/2002 | Taylor et al. | |
| 6,444,461 B1 | 9/2002 | Knapp et al. | |
| 6,471,916 B1 | 10/2002 | Noblett | |
| 6,479,235 B1 | 11/2002 | Schumm et al. | |
| 6,479,299 B1 | 11/2002 | Parce | |
| 6,485,623 B1 | 11/2002 | Anderson | |
| 6,485,625 B1 | 11/2002 | Simpson et al. | |
| 6,494,230 B2 | 12/2002 | Chow | |

(Continued)

FOREIGN PATENT DOCUMENTS

| | | | |
|---|---|---|---|
| EP | 1135530 B1 | 9/2012 | |
| JP | 2000/508539 A | 7/2000 | |
| WO | 97/39138 A1 | 10/1997 | |
| WO | 00/22424 A1 | 4/2000 | |
| WO | 00/31306 | 6/2000 | |
| WO | 01/41931 A2 | 6/2001 | |
| WO | 02/24322 A2 | 3/2002 | |
| WO | 02/097398 A2 | 12/2002 | |
| WO | 2005073691 A1 | 8/2005 | |
| WO | 2006/124842 A2 | 11/2006 | |
| WO | 2007021814 A2 | 2/2007 | |
| WO | WO 2011047329 A2 * | 4/2011 | |

OTHER PUBLICATIONS

Tong et al. Combinatorial fluorescence energy transfer tags for multiplex biological assays. Nature Biotechnology 2001;29:756-9.*

(Continued)

*Primary Examiner* — Kenneth Horlick
(74) *Attorney, Agent, or Firm* — Proskauer Rose LLP

(57) ABSTRACT

Provided are methods for multiplex polymerase chain reaction (PCR) amplification of short tandem repeat (STR) loci that can be used to rapidly generate a highly specific STR profile from target nucleic acids. The resulting STR profiles are useful for human identification purposes in law enforcement, homeland security, military, intelligence, and paternity testing applications.

2 Claims, 30 Drawing Sheets

(56) References Cited

U.S. PATENT DOCUMENTS

| | | |
|---|---|---|
| 6,498,353 B2 | 12/2002 | Nagle |
| 6,531,044 B1 | 3/2003 | Anazawa et al. |
| 6,602,472 B1 | 8/2003 | Zimmennann |
| 6,630,063 B1 | 10/2003 | Li et al. |
| 6,630,680 B2 | 10/2003 | Hakamata et al. |
| 6,635,487 B1 | 10/2003 | Lee |
| 6,646,271 B2 | 11/2003 | Yokokawa |
| 6,648,015 B1 | 11/2003 | Chow |
| 6,664,057 B2 | 12/2003 | Albertson |
| 6,764,512 B2 | 7/2004 | Keller |
| 6,787,016 B2 | 9/2004 | Tan |
| 6,857,449 B1 | 2/2005 | Chow |
| 6,916,614 B1 | 7/2005 | Takenaka |
| 6,929,730 B2 | 8/2005 | Lee |
| 6,952,008 B2 | 10/2005 | Corson |
| 6,987,018 B2 | 1/2006 | Taylor et al. |
| 6,995,841 B2 | 2/2006 | Scott et al. |
| 7,029,562 B2 | 4/2006 | Anazawa et al. |
| 7,033,474 B1 | 4/2006 | Dubrow |
| 7,038,775 B2 | 5/2006 | Sakai |
| 7,069,952 B1 | 7/2006 | McReynolds |
| 7,261,859 B2 | 8/2007 | Andersson et al. |
| 7,280,204 B2 | 10/2007 | Robinson et al. |
| 7,300,199 B2 | 11/2007 | Andersson et al. |
| 7,332,126 B2 | 2/2008 | Tooke et al. |
| 8,018,593 B2 | 9/2011 | Tan et al. |
| 8,206,974 B2 | 6/2012 | Stern |
| 8,425,861 B2 | 4/2013 | Selden |
| 8,961,765 B2 | 2/2015 | Tan et al. |
| 2002/0015147 A1 | 2/2002 | Maher et al. |
| 2002/0046949 A1 | 4/2002 | Nakamura et al. |
| 2002/0530121 | 9/2002 | Promega |
| 2002/0146734 A1 | 10/2002 | Ortyn |
| 2002/0155485 A1 | 10/2002 | Kao |
| 2003/0007898 A1 | 1/2003 | Bohm |
| 2003/0020022 A1 | 1/2003 | Kuwabata et al. |
| 2003/0058440 A1 | 3/2003 | Scott et al. |
| 2003/0059820 A1 | 3/2003 | VoDinh |
| 2003/0082080 A1 | 5/2003 | Zimmermann |
| 2003/0098239 A1 | 5/2003 | Anazawa et al. |
| 2003/0134431 A1 | 7/2003 | Paree |
| 2003/0146145 A1 | 8/2003 | Krotz et al. |
| 2003/0152931 A1 | 8/2003 | Chiou |
| 2004/0011975 A1 | 1/2004 | Nicoli |
| 2004/0150217 A1 | 8/2004 | Heffelfinger et al. |
| 2004/0197816 A1 | 10/2004 | Empedocles et al. |
| 2005/0179901 A1 | 8/2005 | Ostlin et al. |
| 2005/0244879 A1 | 11/2005 | Schumm et al. |
| 2005/0280817 A1* | 12/2005 | Horchner et al. ............ 356/318 |
| 2006/0257958 A1 | 11/2006 | Bruno |
| 2006/0260941 A1 | 11/2006 | Tan et al. |
| 2006/0269922 A1* | 11/2006 | Sagner et al. .................... 435/6 |
| 2006/0286552 A1 | 12/2006 | Goldsmith et al. |
| 2007/0206187 A1 | 9/2007 | Lundquist et al. |
| 2009/0059222 A1* | 3/2009 | Tan et al. ..................... 356/318 |
| 2009/0142764 A1 | 6/2009 | Hennessey |
| 2012/0122093 A1 | 5/2012 | Henessey |

OTHER PUBLICATIONS

Niklas et al. A real-time multiplex SNP melting assay to discriminate individuals; J Forensic Sci 2008;53(6):1316-23.*
Berosik et al. Innovative Software, Hardware, and Consumable Development for the New 3500 Genetic Analyzer System. J Biomol Tech 2010;PMCID PMC2918000: S27.*
Applied Biosystems. Applied Biosystems 3500 and 3500xL Genetic Analyzers. Specification Sheet (2009).*
Giese et al., "Fast Multiplexed Polymerase Chain Reaction for Conventional and Microfluidic Short Tandem Repeat Analysis." J. Forensic Sci, Nov. 2009, vol. 54, No. 6, pp. 1287-1296.
Krenke et al., "Validation of male-specific, 12-locus fluorescent short tandem repeat (STR) multiplex." Forensic Sci Int, 2005, vol. 148, pp. 1-14.
Auroux et al., Micro Total Analysis Systems. 2. Analytical Standard Operations and Applications. 2002, Anal Chem., 74,2637-2652.
Becker and Gärtner, "Polymer microfabrication technologies for microfluidic systems", 2008, Analytical and Bioanalytical Chemistry, 390(1):89.
Becker et al., "Polymer microfabrication methods for microfluidic analytical applications", 2000, Electrophoresis 21: 12-26.
Burns et al., "An Integrated Nanoliter DNA Analysis Device", 1998, Science, 282, 484-487.
Cambridge Technology Inc., "Instruction Manual for Model 6240H Galvanometer Optical Scanner", Sep. 23, 2004, 22 pages.
Dittrich et al., "Micro Total Analysis Systems. Latest Advancements and Trends", 2006, Anal Chem. 78, 3887-3907.
Edwards et al., "DNA typing and genetic mapping with trimeric and tetrameric tandem repeats", 1991, Am J Hum Genet, 49(4): 746-756.
Fiorini and Chiu, "Disposable Microfluidic Devices: Fabrication, Function, and Application", 2005, Bio Techniques, 38, 429-446.
Geiss et al., "Direct Multiplexed Measurement of Gene Expression with Color-Coded Probe Pairs", 2008, Nature Biotechnology, 26(3), 317-325.
Gerstner Andreas Oh et al; "Near-infrared dyes for six-color immunophenotyping by laser scanning cytometry"; Cytometry; Jul. 1, 2002; pp. 115-123; vol. 48; No. 3; Wiley.
Giese et al., "Fast Multiplex ad Polymerase Chain Reaction for Conventional and Microfluidic Short Tandem Repeat Analysis", J Forensic Sci. Nov. 2009 vol. 54 No. 6 pp. 1287-1296. Especially p. 1288 col. 1 para 3.
Hawkins and Yager, "Nonlinear decrease of background fluorescence in polymer thin-films—a survey of materials and how they can complicate fluorescence detection in μTAS", 2003, Lab Chip, 3(4): 248-52.
Hill article, ("A 26 Plex Autosomal STR Assay to Aid Human Identity Testing"), J. Forensic Sci. Sep. 2009, vol. 54, No. 5, pp. 1008-1015.
Imai et al, "Multi-capillary DNA sequencer", Hitachi Review, vol. 48 (1999), pp. 107-109.
Janasek et al., "Scaling and the Design of Miniaturized Chemical-Analysis Systems", 2006, Nature, 442, 374-380.
Kamentsky LA et al, "Side-Based laser scanning cytometry"; ACTA Cytologica; Jan. 1, 1997; pp. 123-143; vol. 41; No. 1; International Academy of Cytology, Chicago, IL, US.
Kan et al, "DNA sequencing and genotyping in miniaturized electrophoresis systems", 2004, Electrophoresis 25 (21-22): 3564-3588.
Karlinsey, J.M., et al., "Pressure Injection on a Valved Microdevice for Electrophoretic Analysis of Submicroliter Samples," Analytical Chemistry, vol. 77, No. 11, Jun. 1, 2005, pp. 3637-3643.
Koh, C.G., et al., "Integrating Polymerasc Chain Reaction, Valving, and Electrophoresis in a Plastic Device for Bacterial Detection," Analytical Chemistry, vol. 75, No. 17, Sep. 1, 2003, pp. 4591-4598.
Krenke et al. Validation of male-specific, 12-locus fluorescent short tandem repeat (STR) multiplex. Forensic Sci. Int. Jun. 30, 2005 vol. 151 No. 1 pp. 1-14.
Liu et al, Integrated Portable Polymerase Chain Reaction-Capillary Electrophoresis Microsystem for Rapid Forensic Short Tandem Repeat Typing, 2007, Anal. Chem., 79, 1881-9.
Maxam and Gilbert, A new method for sequencing DNA, 1977, Proc. Natl. Academy Sci. USA 74, 560-564.
McCormick, et al., Microchannel Electrophoretic Separations of DNA in Injection-Molded Plastic Substrates, 1997, Anal Chem. 69(14): 2626-2630.
Metzker, Emerging Technologies in DNA Sequencing, 2005, Genome Research 15: 1767-1776.
Milligan el al., Current concepts in antisense drug design, 1993, J. Med. Chem. 36:1923-1937 17.
Mittag Anja et al.; "Polychromatic (eight-color) slide-based cytometry for the phenotyping of leukocyte, NK, and NKT subsets"; Cytometry; Jun. 2005; pp. 10 3-115; vol. 65A; No. 2; Wiley.
Paegel et al., "High Throughput DNA Sequencing with a Microfabricated 96-lane Capillary Array Electrophoresis Bioprocessor", 2002, Proc. Natl. Academy Sci., 99(2), 574-579.
Pal et al., "An Integrated Microfluidic Device for Influenza and Other Genetic Analyses", 2005, Lab Chip, 5, 1024-1032.
Piruska et al., "The autofluorescence of plastic materials and chips measured under laser irradiation", 2005, Lab Chip 5(12): 1348-1354.

(56) References Cited

OTHER PUBLICATIONS

Sanger et al., "DNA sequencing with chain-terminating inhibitors", 1977, Proc. Natl. Academy Sci., USA 74, 5463-5467.

Sassi, et al., "Rapid, parallel separations of D1S80 alleles in a plastic microchannel chip", 2000, J Chromatogra, 894 (1-2): 203-217.

Shi and Anderson, "High-resolution single-stranded DNA analysis on 4.5 cm plastic electrophoretic microchannels", 2003, Electrophoresis 24(19-20): 3371-3377.

Shi, Yining, DNA sequencing and multiplex STR analysis on plastic microfluidic devices; Wiley-VCH, 2006 pp. 3703-3711.

Strauss-Soukup et al., Effects of Neutralization Pattern and Stereochemistry on DNA Bending by Methylphosphonate Substitutions, 1997, Biochemistry 36:8692-8698.

Summary of Lectures (a discussion meeting in Tokyo) 1993, vol. 1993, pp. 73-74.

Wabuyele et al., "Single molecule detection of double-stranded DNA in poly(methylmethacrylate) and polycarbonate microfluidic devices", 2001, Electrophoresis 22(18): 3939-48.

Zhang and Da Xing, "Miniaturized PCR Chips for Nucleic Acid Amplification and Analysis: Latest Advances and Future Trends", 2007, Nucleic Acids Research, 1-15.

Declaration of Eugene Tan Under 37 C.F.R §1.132, filed in U.S. Appl No. 13/834,226, signed May 1, 2015, 9 pages.

Declaration of Eugene Tan Under 37 C.F.R §1.132, filed in U.S. Appl. No. 13/835,347, signed Oct. 6, 2015, 12 pages.

Amendment and Interview Summary filed in the PTO on Sep. 30, 2015 in U.S. Appl. No. 13/191,952.

\* cited by examiner

EXAMPLE 1

EXAMPLE 1

EXAMPLE 2

EXAMPLE 3

EXAMPLE 4

EXAMPLE 5

EXAMPLE 7

EXAMPLE 8

EXAMPLE 10

EXAMPLE 10

EXAMPLE 10

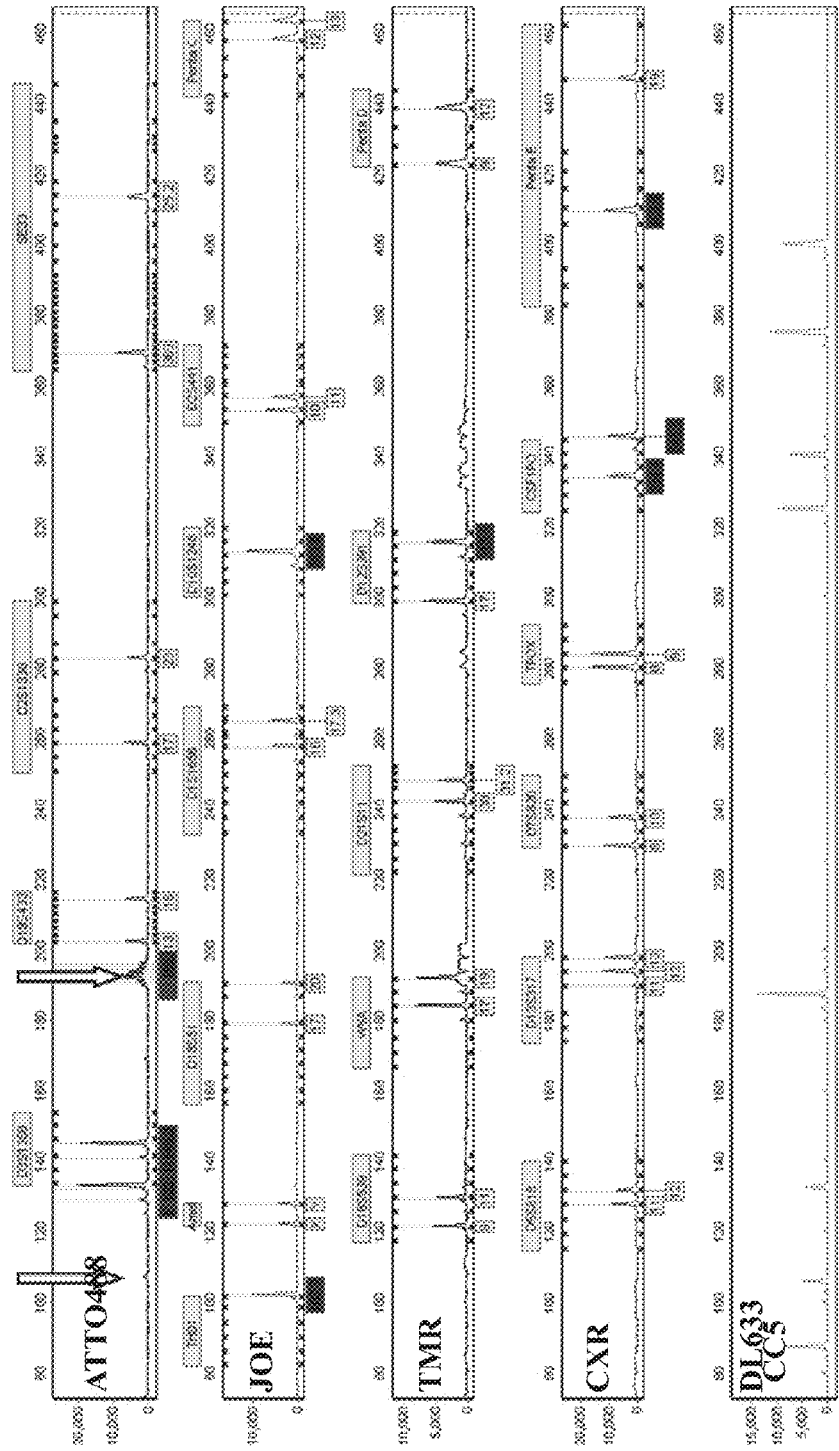

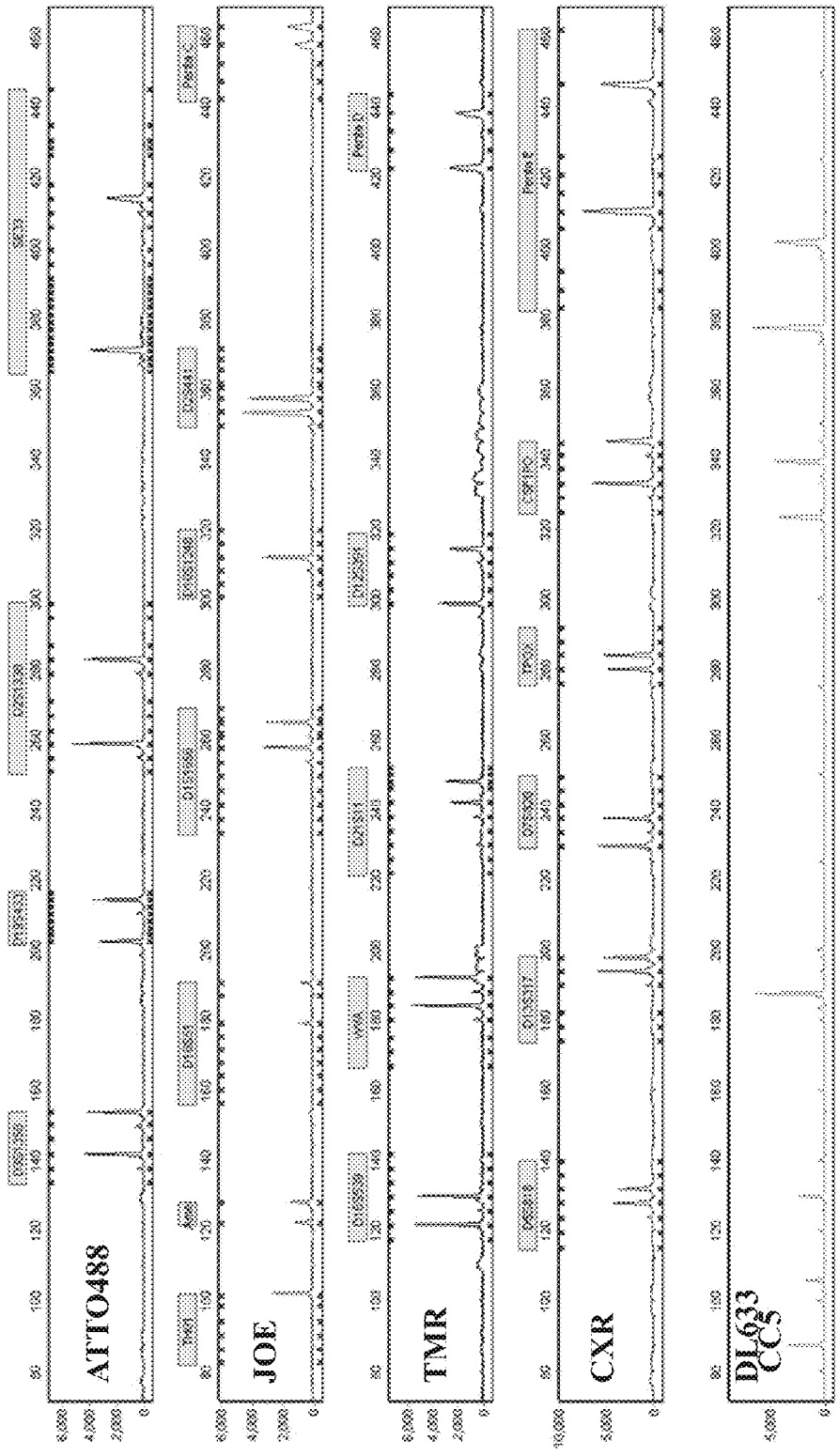

EXAMPLE 12

EXAMPLE 13

EXAMPLE 13

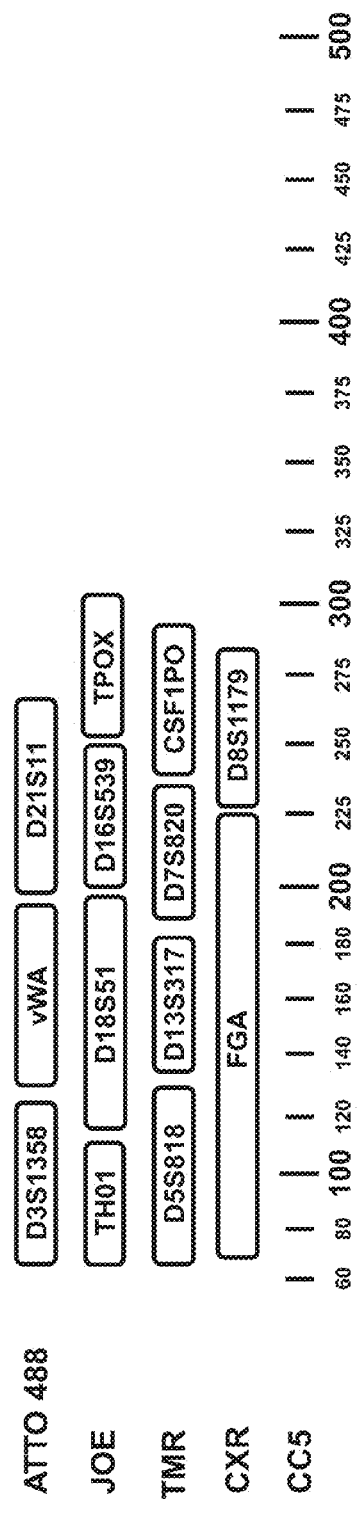

EXAMPLE 14
FIG 15B

| Dye | Loci |
|---|---|
| ATTO 488 | D3S1358, vWA, D21S11 |
| JOE | TH01, D18S51, D16S539 |
| TMR | D5S818, D13S317, D7S820 |
| CXR | FGA |
| DL633 | D8S1179, CSF1PO, TPOX |
| CC5 | (size standard) |

Size scale (bp): 60, 80, 100, 120, 140, 160, 180, 200, 225, 250, 275, 300, 325, 350, 375, 400, 425, 450, 475, 500

EXAMPLE 14
FIG 15C

ATTO 488    [D3S1358]  [TPOX]
JOE         [TH01]     [D18S51]
TMR         [D5S818]   [D13S317]
CXR         [    FGA    ]
DL633       [D8S1179]   [CSF1PO]
Lissamine-  [D16S539]   [D21S11]
Rhodamine
ATTO 594    [D7S820]    [vWA]
CC5

60  80  100  120  140  160  180  200  225  250  275  300  325  350  375  400  425  450  475  500

| Multiplex Content | STR Locus Size Range Sum | Multiplex Size Range | Multiplex Density |
|---|---|---|---|
| 13 Loci – 5 Dyes | 689 | 235 | 2.93 |
| 13 Loci – 6 Dyes | 689 | 205 | 3.36 |
| 13 Loci – 8 Dyes | 689 | 160 | 4.31 |

EXAMPLE 15

EXAMPLE 16

EXAMPLE 17

EXAMPLE 18

METHODS AND COMPOSITIONS FOR RAPID MULTIPLEX AMPLIFICATION OF STR LOCI

RELATED APPLICATIONS

This application claims priority from provisional application No. 61/485,459 filed May 12, 2011.

INCORPORATION BY REFERENCE

This application incorporates by reference in their entireties, the following applications: U.S. application Ser. No. 11/132,712 entitled "Ruggedized Apparatus for Analysis of Nucleic Acid and Proteins"; U.S. application Ser. No. 12/080,746 entitled "Methods for Rapid Multiplexed Amplification of Target Nucleic Acids"; U.S. application Ser. No. 12/080,745 entitled "Plastic Microfluidic Separation and Detection Platforms"; U.S. application Ser. No. 12/080,751 entitled "Integrated Nucleic Acid Analysis"; and U.S. application Ser. No. 13/044,485 entitled "Unitary Biochips."

GOVERNMENT SUPPORT

This invention was made with government support under an SBIR Grant from the Department of Homeland Security, No. N10PC2010S. The government may have certain rights in the invention.

FIELD OF THE INVENTION

The present invention relates generally to compositions and methods for the rapid amplification of Short Tandem Repeat loci within a nucleic acid sample.

BACKGROUND OF THE INVENTION

A polymerase chain reaction (PCR) is an enzymatic reaction that facilitates rapid exponential amplification of nucleic acid sequences in vitro. In forensics, PCR can be utilized to identify individuals based on the amplification of small regions of the human genome containing a class of repeated DNA known as Short Tandem Repeats (STRs). The unit length of a given STR repeat ranges between 2-10 base pairs, and STRs generally fall within non-coding and flanking sequences but occasionally within coding regions (Edwards et al., Am. J. Hum. Genet. 1991, 49, 746-756). There are several hundred thousand STR loci in the human genome, occurring on average every 6-10 kb (Beckman and Weber, Genomics 1992, 12, 627-631) and many of these are highly polymorphic (Edwards et al., Trans. Assoc. Am. Physicians 1989, 102, 185-194). STR analysis has become a major tool in the forensic armamentarium with a growing set of applications including law enforcement, paternity testing, human identification in mass disasters, and routine typing of children.

SUMMARY OF THE INVENTION

In one aspect, this invention provides method for multiplex amplification of STR loci comprising (a) contacting in solution a sample with at least six different primer pairs for STR loci wherein at least one primer of each pair is labeled with a fluorescent dye and wherein the resultant STR multiplex has a Multiplex Density equal to or greater than 3.20; (b) simultaneously amplifying by polymerase chain reaction (PCR) in one reaction chamber using said at least six primer pairs to produce amplified nucleic acid products; and (c) detecting the nucleic acid products by laser induced fluorescence. In related aspects, the multiplex STR assay has a multiplex density of 3.0 or greater, 3.1 or greater, 3.2 or greater, 3.3 or greater, 3.4 or greater, 3.5 or greater, 3.6 or greater, 3.7 or greater, 3.8 or greater, 3.9 or greater, 4.0 or greater, 4.2 or greater, 4.4 or greater, 4.6 or greater, 4.8, or greater, 5.0 or greater, 5.5 or greater, 6.0 or greater, 6.5 or greater, 7.0 or greater, 7.5 or greater, 8.0 or greater, 8.5 or greater, 9.0 or greater, 9.5 or greater, or 10.0 or greater. In some embodiments, a total of 4, 5, 6, 7, 8, 9, 10, 11, 12, 13, 14, 15, 16, 17, 18, 19, 20, 21, 22, 23, 24, 25, 26, 27, 28, 30, 35, 40 or more fluorescent dyes are utilized to label primers (one member of each primer pair is labeled), and the dye-labeled fragments are detected based on laser excitation and detection. Increasing the number of fluorescent dyes allows a greater multiplex density.

In another aspect, this invention provides methods for multiplex amplification of STR loci comprising (a) contacting in solution a sample with at least six different primer pairs for STR loci wherein at least one primer of each pair is labeled with a fluorescent dye and wherein at least six different fluorescent dye-labels are used and wherein the resultant STR multiplex has an STR Locus Size Range Sum greater than 1044; (b) simultaneously amplifying by polymerase chain reaction (PCR) in one reaction chamber using said at least six primer pairs to produce amplified nucleic acid products; and (e) detecting the nucleic acid products by laser induced fluorescence. In related aspects, the multiplex STR assay has a STR Locus Size Range Sum of 1050 bases or greater, 1075 bases or greater, 1100 bases or greater, 1125 bases or greater, 1150 bases or greater, 1175 bases or greater, 1200 bases or greater, 1225 bases or greater, 1250 bases or greater, 1275 bases or greater, 1300 bases or greater, 1325 bases or greater, 1350 bases or greater, 1375 bases or greater, 1400 bases or greater, 1425 bases or greater, 1450 bases or greater, 1475 bases or greater, 1500 bases or greater, 1600 bases or greater, 1700 bases or greater, 1800 bases or greater, 1900 bases or greater, 2000 bases or greater, 2500 bases or greater, 3000 bases or greater, 4000 bases or greater, or 5000 bases or greater. In some embodiments, a total of 4, 5, 6, 7, 8, 9, 10, 11, 12, 13, 14, 15, 16, 17, 18, 19, 20, 21, 22, 23, 24, 25, 26, 27, 28, 30, 35, 40 or more fluorescent dyes are utilized to label primers (one member of each primer pair is labeled), and the dye-labeled fragments are detected based on laser excitation and detection. Increasing the number of fluorescent dyes allows a greater STR Locus Size Range Sum.

Certain aspects provided herein relate to methods of multiplex amplification of polymorphic loci, comprising (a) contacting in one solution a sample of one more nucleic acid templates obtained from one or more sources with at least six different primer pairs, each pair hybridizing to one of at least six STR loci in the one or more nucleic acid templates, wherein at least one primer of the primer pair is labeled, and wherein at least six (and in some aspects five, and in yet other aspects, more than six) different labels are used; (b) amplifying by polymerase chain reaction (PCR) in one reaction chamber at least six STR polymorphic loci in the one or more nucleic acids to produce at least six nucleic acid products. In some embodiments, 6 or more loci are amplified. In some embodiments, 7 or more, 8 or more, 9 or more, 10 or more, 11 or more, 12 or more, 13 or more, 14 or more, 15 or more, 16 or more, 17 or more, 18 or more, 19, or more, 20 or more, 21 or more, 22 or more, 23 or more, 24 or more, 25 or more, 26 or more, 27 or more, 28 or more, 29 or more, 30 or more, 31 or more, 32 or more, 34 or more, 36 or more, 38 or more, or 40 or more STR loci are amplified.

In some embodiments, the multiplex STR assay contains primer pairs for STR loci D3S1358, D19S433, D2S1338, TH01, D18S51, D1S1656, D10S1248, D2S441, D16S539, vWA, D21S11, D12S391, D22S1045, FGA, D8S1179, and a primer pair for at least one additional STR locus. In some embodiments, the multiplex STR assay contains primer pairs for STR loci D3S1358, D19S433, D2S1338, TH01, D18S51, D1S1656, D10S1248, D2S441, D16S539, vWA, D21S11, D12S391, D22S1045, FGA, D8S1179, and at least one primer pair for an STR loci selected from the set of STR loci SE33, Penta C, Penta D, Penta E, D5S818, D13S317, D7S820, TPOX, CSF1PO, DYS391, and D6S1043. In some embodiments, a total of 4, 5, 6, 7, 8, 9, 10, 11, 12, 13, 14, 15, 16, 17, 18, 19, 20, 21, 22, 23, 24, 25, 26, 27, 28, 30, 35, 40 or more fluorescent dyes are utilized to label primers (one member of each primer pair is labeled), and the dye-labeled fragments are detected based on laser excitation and detection. In some embodiments, amelogenin or another marker for sex identification may optionally be included in the multiplex.

In some embodiments, the multiplex STR assay contains primer pairs for STR loci D3S1358, D19S433, D2S1338, TH01, D18S51, D16S539, vWA, D21S11, Penta D, D5S818, D13S317, D7S820, TPOX, CSF1PO, Penta E, FGA, D8S1179, and a primer pair for at least one additional STR locus. In some embodiments, the multiplex STR assay contains primer pairs for STR loci D3S1358, D19S433, D2S1338, TH01, D18S51, D16S539, vWA, D21S11, Penta D, D5S818, D13S317, D7S820, TPOX, CSF1PO, Penta E, FGA, D8S1179, and at least one primer pair for an STR locus selected from the set of STR loci SE33, D1S1656, D10S1248, D2S441, Penta C, D12S391, D22S1045, DYS391, and D6S1043. In some embodiments, a total of 4, 5, 6, 7, 8, 9, 10, 11, 12, 13, 14, 15, 16, 17, 18, 19, 20, 21, 22, 23, 24, 25, 26, 27, 28, 30, 35, 40 or more fluorescent dyes are utilized to label primers (one member of each primer pair is labeled), and the dye-labeled fragments are detected based on laser excitation and detection. In some embodiments, amelogenin or another marker for sex identification may optionally be included in the multiplex.

In some embodiments, the multiplex STR assay contains primer pairs for STR loci D3S1358, D19S433, D2S1338, TH01, D18S51, D1S1656, D16S539, vWA, D21S11, D12S391, Penta D, D5S818, D13S317, D7S820, TPOX, CSF1PO, Penta E, FGA, D8S1179, D6S1043, and a primer pair for at least one additional STR locus. In some embodiments, the multiplex STR assay contains primer pairs for STR loci D3S1358, D19S433, D2S1338, TH01, D18S51, D1S1656, D16S539, vWA, D21S11, D12S391, Penta D, D5S818, D13S317, D7S820, TPOX, CSF1PO, Penta E, FGA, D8S1179, D6S1043, and at least one additional primer pair for an STR locus selected from the set of STR loci SE33, D10S1248, D2S441, Penta C, D22S1045, and DYS391. In some embodiments, a total of 4, 5, 6, 7, 8, 9, 10, 11, 12, 13, 14, 15, 16, 17, 18, 19, 20, 21, 22, 23, 24, 25, 26, 27, 28, 30, 35, 40 or more fluorescent dyes are utilized to label primers (one member of each primer pair is labeled), and the dye-labeled fragments are detected based on laser excitation and detection. In some embodiments, amelogenin or another marker for sex identification may optionally be included in the multiplex.

In some embodiments, the multiplex STR assay contains primer pairs for STR loci D3S1358, D19S433, D2S1338, TH01, D18S51, D1S1656, D10S1248, D2S441, D16S539, vWA, D21S11, D12S391, D5S818, D13S317, D7S820, CSF1PO, DYS391, FGA, D8S1179, and a primer pair for at least one additional STR locus. In some embodiments, the multiplex STR assay contains primer pairs for STR loci D3S1358, D19S433, D2S1338, TH01, D18S51, D1S1656, D10S1248, D2S441, D16S539, vWA, D21S11, D12S391, D5S818, D13S317, D7S820, CSF1PO, DYS391, FGA, D8S1179, and at least one additional primer pair for an STR locus selected from the set of STR loci SE33, Penta C, Penta D, TPOX, Penta E, D22S1045, and D6S1043. In some embodiments, a total of 4, 5, 6, 7, 8, 9, 10, 11, 12, 13, 14, 15, 16, 17, 18, 19, 20, 21, 22, 23, 24, 25, 26, 27, 28, 30, 35, 40 or more fluorescent dyes are utilized to label primers (one member of each primer pair is labeled), and the dye-labeled fragments are detected based on laser excitation and detection. In some embodiments, amelogenin or another marker for sex identification may optionally be included in the multiplex.

In some embodiments, the multiplex STR assay contains primer pairs for STR loci D3S1358, D19S433, D2S1338, TH01, D18S51, D1S1656, D10S1248, D2S441, D16S539, vWA, D21S11, D12S391, D5S818, D13S317, D7S820, TPOX, CSF1PO, D22S1045, DYS391, FGA, D8S1179, and a primer pair for at least two additional STR loci. In some embodiments, the multiplex STR assay contains primer pairs for STR loci D3S1358, D19S433, D2S1338, TH01, D18S51, D1S1656, D10S1248, D2S441, D16S539, vWA, D21S11, D12S391, D5S818, D13S317, D7S820, TPOX, CSF1PO, D22S1045, DYS391, FGA, D8S1179, and at least one additional primer pair, respectively, for an STR locus selected from the set of STR loci Penta C, Penta D, Penta E, SE33, and D6S1043. In some embodiments, a total of 4, 5, 6, 7, 8, 9, 10, 11, 12, 13, 14, 15, 16, 17, 18, 19, 20, 21, 22, 23, 24, 25, 26, 27, 28, 30, 35, 40 or more fluorescent dyes are utilized to label primers (one member of each primer pair is labeled), and the dye-labeled fragments are detected based on laser excitation and detection. In some embodiments, amelogenin or another marker for sex identification may optionally be included in the multiplex.

In some embodiments, the multiplex STR assay contains primer pairs for STR loci D3S1358, D19S433, D2S1338, SE33, TH01, D18S51, D1S1656, D10S1248, D2S441, D16S539, vWA, D21S11, D12S391, D5S818, D13S317, D7S820, TPOX, CSF1PO, D22S1045, DYS391, FGA, D8S1179, and a primer pair for at least one additional STR locus. In some embodiments, the multiplex STR assay contains primer pairs for STR loci D3S1358, D19S433, D2S1338, SE33, TH01, D18S51, D1S1656, D10S1248, D2S441, D16S539, vWA, D21S11, D12S391, D5S818, D13S317, D7S820, TPOX, CSF1PO, D22S1045, DYS391, FGA, D8S1179, and at least one additional primer pair for an STR locus selected from the set of STR loci Penta C, Penta D, Penta E, and D6S1043. In some embodiments, a total of 4, 5, 6, 7, 8, 9, 10, 11, 12, 13, 14, 15, 16, 17, 18, 19, 20, 21, 22, 23, 24, 25, 26, 27, 28, 30, 35, 40 or more fluorescent dyes are utilized to label primers (one member of each primer pair is labeled), and the dye-labeled fragments are detected based on laser excitation and detection. In some embodiments, amelogenin or another marker for sex identification may optionally be included in the multiplex.

In some embodiments, the multiplex STR assay contains primer pairs for STR loci D3S1358, TH01, D18S51, D16S539, vWA, D21S11, D5S818, D13S317, D7S820, TPOX, CSF1PO, FGA, D8S1179, and at least six additional primer pairs each, respectively, amplifying at least one additional STR locus. In some embodiments, the multiplex STR assay contains primer pairs for STR loci D3S1358, TH01, D18S51, D16S539, vWA, D21S11, D5S818, D13S317, D7S820, TPOX, CSF1PO, FGA, D8S1179, and at least six additional primer pairs containing at least one primer pair for at least 1, 2, 3, 4, 5, 6, 7, 8, 9, 10, 11, or 12 additional STR locus selected from the set of STR loci D19S433, D2S1338, SE33, D1S1656, D10S1248, D2S441, Penta C, D12S391, Penta D, Penta E, D22S1045, and DYS391, In some embodiments, a total of 4, 5, 6, 7, 8, 9, 10, 11, 12, 13, 14, 15, 16, 17, 18, 19, 20, 21, 22, 23, 24, 25, 26, 27, 28, 30, 35, 40 or more fluorescent dyes are utilized to label primers (one member of each primer pair is labeled), and the dye-labeled fragments are detected based on laser excitation and detection. In some embodiments, amelogenin or another marker for sex identification may optionally be included in the multiplex.

In some embodiments, the multiplex STR assay contains primer pairs for STR loci D3S1358, D19S433, D2S1338, TH01, D18S51, D1S6156, D10S1248, D2S441, D16S539, vWA, D21S11, D12S391, D22S1045, FGA, D8S1179 and at least two additional primer pairs each, respectively, amplifying at least one additional STR locus. In some embodiments, the multiplex STR assay contains primer pairs for STR loci D3S1358, D19S433m D2S1338, TH01, D18S51, D16S539, D10S1248, D2S441, D16S539, vWA, D21S11, D12S391, D22S1045, FGA, D8S1179 and at least two additional primer pairs each, respectively, amplifying at least one additional STR locus and selected from the group of STR loci SE33, Penta C, Penta D, D5S818, D13S317, D7S820, TPOX, CSF1PO, Penta E, DYS391, and D6S1043. In some embodiments, a total of 4, 5, 6, 7, 8, 9, 10, 11, 12, 13, 14, 15, 16, 17, 18, 19, 20, 21, 22, 23, 24, 25, 26, 27, 28, 30, 35, 40 or more fluorescent dyes are utilized to label primers (one member of each primer pair is labeled), and the dye-labeled fragments are detected based on laser excitation and detection. In some embodiments, amelogenin or another marker for sex identification may optionally be included in the multiplex.

In some embodiments, the multiplex STR assay contains primer pairs for STR loci D3S1358, D19S433, D2S1338, D18S51, D16S539, D21S11, D12S391, D5S818, D13S317, D7S820, CSF1PO, FGA, D8S1179, and D6S1043 and a primer pair for at least one additional STR loci. In some embodiments, the multiplex STR assay contains primer pairs for STR loci D3S1358, D19S433, D2S1338, D18S51, D16S539, D21S11, D12S391, D5S818, D13S317, D7S820, CSF1PO, FGA, D8S1179, and D6S1043 and at least one additional primer pair, respectively, for an STR locus selected from the set of STR loci SE33, TH01, D1S1656, D10S1248, D2S441, Penta C, vWA, Penta D, D22S1045, Penta E, SE33, and D6S1043. In some embodiments, a total of 4, 5, 6, 7, 8, 9, 10, 11, 12, 13, 14, 15, 16, 17, 18, 19, 20, 21, 22, 23, 24, 25, 26, 27, 28, 30, 35, 40 or more fluorescent dyes are utilized to label primers (one member of each primer pair is labeled), and the dye-labeled fragments are detected based on laser excitation and detection. In some embodiments, amelogenin or another marker for sex identification may optionally be included in the multiplex.

In some embodiments, the multiplex STR assay contains primer pairs for STR loci D3S1358, D19S433, D2S1338, D18S51, D16S539, D10S1248, D2S441, D16S539, vWA, D21S11, D12S391, D5S818, D13S317, D7S820, CSF1PO, D22S1045, FGA, and D8S1179 with or without at least one additional primer pair, respectively, for an STR locus selected from the set of STR loci SE33, Penta C, Penta D, TPOX, Penta E, DYS391, and D6S1043. In some embodiments, a total of 4, 5, 6, 7, 8, 9, 10, 11, 12, 13, 14, 15, 16, 17, 18, 19, 20, 21, 22, 23, 24, 25, 26, 27, 28, 30, 35, 40 or more fluorescent dyes are utilized to label primers (one member of each primer pair is labeled), and the dye-labeled fragments are detected based on laser excitation and detection. In some embodiments, amelogenin or another marker for sex identification may optionally be included in the multiplex.

In some embodiments, the multiplex STR assay has a multiplex density of 3.0 or greater, 3.1 or greater, 3.2 or greater, 3.3 or greater, 3.4 or greater, 3.5 or greater, 3.6 or greater, 3.7 or greater, 3.8 or greater, 3.9 or greater, 4.0 or greater, 4.2 or greater, 4.4 or greater, 4.6 or greater, 4.8, or greater, 5.0 or greater, 5.5 or greater, 6.0 or greater, 6.5 or greater, 7.0 or greater, 7.5 or greater, 8.0 or greater, 8.5 or greater, 9.0 or greater, 9.5 or greater, or 10.0 or greater. In some embodiments, a total of 4, 5, 6, 7, 8, 9, 10, 11, 12, 13, 14, 15, 16, 17, 18, 19, 20, 21, 22, 23, 24, 25, 26, 27, 28, 30, 35, 40 or more fluorescent dyes are utilized to label primers (one member of each primer pair is labeled), and the dye-labeled fragments are detected based on laser excitation and detection. Increasing the number of fluorescent dyes allows a greater multiplex density.

In some embodiments, the multiplex STR assay has a STR Locus Size Range Sum of 1044 bases or greater, 1050 bases or greater, 1075 bases or greater, 1100 bases or greater, 1125 bases or greater, 1150 bases or greater, 1175 bases or greater, 1200 bases or greater, 1225 bases or greater, 1250 bases or greater, 1275 bases or greater, 1300 bases or greater, 1325 bases or greater, 1350 bases or greater, 1375 bases or greater, 1400 bases or greater, 1425 bases or greater, 1450 bases or greater, 1475 bases or greater, 1500 bases or greater, 1600 bases or greater, 1700 bases or greater, 1800 bases or greater, 1900 bases or greater, 2000 bases or greater, 2500 bases or greater, 3000 bases or greater, 4000 bases or greater, or 5000 bases or greater. In some embodiments, a total of 4, 5, 6, 7, 8, 9, 10, 11, 12, 13, 14, 15, 16, 17, 18, 19, 20, 21, 22, 23, 24, 25, 26, 27, 28, 30, 35, 40 or more fluorescent dyes are utilized to label primers (one member of each primer pair is labeled), and the dye-labeled fragments are detected based on laser excitation and detection. Increasing the number of fluorescent dyes allows a greater STR Locus Size Range Sum.

The use of six or more fluorescent labels (e.g., 6, 7, 8, 9, 10, 11, 12, 13, 14, 15, 16, 17, 18, 19, 20, or more labels) offers many advantages. For example, when working with degraded DNA samples, the likelihood of generating all the desired amplification products is increased with the use of small amplicons in the multiplex STR evaluation. The use of six, or more labeling dyes increases the chance for success with degraded DNA samples by allowing reduction of the average amplicon size of the loci by permitting additional loci to be designed in the smallest possible range larger than the artifacts of primers and primer dimers. In some embodiments, 6 or more loci are amplified in a multiplex set, wherein at least one primer of each primer pair is labeled, and wherein at least six different labels are used. In some embodiments, 12 or more loci are amplified in a multiplex set, wherein at least one primer of each primer pair is labeled, and wherein at least six different labels are used. In some embodiments, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 40, 45, 50, or more loci are amplified in a multiplex set, wherein at least one primer of each primer pair is labeled, and wherein at least six different labels are used. It is specifically envisioned that governments will approve additional loci over time and the use of a six of more colors in a multiplex set to allow more than 27 loci is envisioned. One of more loci may be replaced. For example, the FBI is currently considering downgrading the TPOX locus from its current required status to a recommended status for also sample profiles to be entered into the United States CODIS database.

This increase in colors and number of STR loci that can be interrogated will also reduce the incidence of adventitious matches (ENFSI document on DNA-database management 2010, and will add confidence in the execution of many other STR-based applications. For example, the role of DNA profiling has also expanded to include familial searching of databases (Bieber et al. Finding criminals through DNA of their relatives. Science. 2006; 312(5778):1315-6; Nothnagel et al. Potentials and limits of pairwise kinship analysis using autosomal short tandem repeat loci. Int J Legal Med. 2010; 124 (3):205-15) and kinship analysis is being employed in refugee, asylee, and immigration applications (Baker et al. Reuniting Families: An Online Database to Aid in the Identification of Undocumented Immigrant Remains*. J Forensic Sci. 2008; 53(1):50-3; Preston. US set to begin a vast expansion of DNA sampling; big effect on immigrants; law to cover most people detained or arrested by federal agents. The New York times. 2007:A1, A15).

Another advantage of the use of six or more labels is based on the fact that several countries have defined standard sets of STR loci for use in the creation of national databases employed to assist in identification of perpetrators of various crimes (Budowle et al. Population Data on the Thirteen CODIS Core Short Tandem Repeat Loci in African-Americans, US Caucasians, Hispanics, Bahamians, Jamaicans, and Trinidadians. J Forensic Sci. 1999; 44:1277-86; Butler. Genetics and genomics of core short tandem repeat loci used in human identity testing. J Forensic Sci. 2006 March; 51(2): 253-65; Gill et al. New multiplexes for Europe—Amendments and clarification of strategic development. Forensic Sci Int. 2006; 163(1-2):155-7). These standards sets vary from country to country. With time, the sizes of regional, national, and international databases have increased, as has the desire to share STR profile data across borders. Database search compatibility will benefit from increasing the number of STR loci that can be analyzed simultaneously. The use of six or more labels allows the creation of a new international STR standard that incorporates essentially all of the STR loci used in individual countries.

There are several categories of STR loci that can be incorporated into multiplexed STR assays. These include autosomal STRs (most of those discussed above), X STRs, Y STRs, and mini-STRs (lower molecular weight versions of autosomal, Y- and X-STRs). STR assays can consist of one type of STR locus or combinations of STR loci in a given assay (e.g. autosomal, X, and Y-STRs can be interrogated together).

In cases in which a direct line of male-to-male inheritance is to be evaluated, kinship analysis and investigation of geographic ancestry benefit significantly from the use Y chromosome STR markers. In some embodiments, 6 or more Y chromosome STR loci, (with 6, 8, 10, 12, 14, 15, 18, 21, 24, 27, 30 or more Y chromosome STR loci preferred for some applications) wherein at least one primer of each primer pair is labeled, and wherein at least six different labels are used, are amplified in a multiplex set. In some embodiments, 18 or more loci, wherein at least one primer of each primer pair is labeled, and wherein at least six different labels are used, are amplified in a multiplex set. In some embodiments, 18 or more loci with at least one selected from DYS19, DYS378I, DYS389II, DYS390, DYS391, DYS392, DYS393, DYS385a/b, DYS437, DYS438, DYS439, DYS472, DYS476, DYS480, DYS481, DYS485, DYS487, DYS488, DYS490, DYS491, DYS492, DYS494, DYS495, DYS497, DYS505, DYS508, DYS511, DYS522, DYS525, DYS530, DYS531, DYS533, DYS537, DYS540, DYS549, DYS554, DYS556, DYS565, DYS567, DYS568, DYS569, DYS570, DYS572, DYS573, DYS575, DYS576, DYS578, DYS579, DYS580, DYS583, DYS589, DYS590, DYS594, DYS617, DYS618, DYS636, DYS640, DYS641, or DYS643, wherein at least one primer of each primer pair is labeled, and wherein at least six different labels are used, are amplified in a multiplex set. In some embodiments, 24 or more loci with at least one selected from DYS19, DYS378I, DYS389II, DYS390, DYS391, DYS392, DYS393, DYS385a/b, DYS437, DYS438, DYS439, DYS472, DYS476, DYS480, DYS481, DYS485, DYS487, DYS488, DYS490, DYS491, DYS492, DYS494, DYS495, DYS497, DYS505, DYS508, DYS511, DYS522, DYS525, DYS530, DYS531, DYS533, DYS537, DYS540, DYS549, DYS554, DYS556, DYS565, DYS567, DYS568, DYS569, DYS570, DYS572, DYS573, DYS575, DYS576, DYS578, DYS579, DYS580, DYS583, DYS589, DYS590, DYS594, DYS617, DYS618, DYS636, DYS640, DYS641, or DYS643, wherein at least one primer of each primer pair is labeled, and wherein at least six different labels are used, are amplified in a multiplex set.

In some embodiments, 30 or more loci with at least one selected from DYS19, DYS378I, DYS389II, DYS390, DYS391, DYS392, DYS393, DYS385a/b, DYS437, DYS438, DYS439, DYS472, DYS476, DYS480, DYS481, DYS485, DYS487, DYS488, DYS490, DYS491, DYS492, DYS494, DYS495, DYS497, DYS505, DYS508, DYS511, DYS522, DYS525, DYS530, DYS531, DYS533, DYS537, DYS540, DYS549, DYS554, DYS556, DYS565, DYS567, DYS568, DYS569, DYS570, DYS572, DYS573, DYS575, DYS576, DYS578, DYS579, DYS580, DYS583, DYS589, DYS590, DYS594, DYS617, DYS618, DYS636, DYS640, DYS641, or DYS643, wherein at least one primer of each primer pair is labeled, and wherein at least six different labels are used, are amplified in a multiplex set.

In complex deficiency cases in kinship, forensics, and anthropology, X chromosome markers are particularly useful for analyses. The X-chromosome profile of males is passed on to offspring as a haplotype, making it a highly polymorphic combined system for familial identifications. In some embodiments, 6, 7, 8, 9, 10, 12, 14, 16, 18, 20, 25, 30 or more X chromosome STR loci, wherein at least one primer of each primer pair is labeled, and wherein at least six different labels are used, are amplified in a multiplex set. In some embodiments, 13 or more loci, with at least one selected from DXS6807, DXS9895, DXS10135, DXS8378, DXS9902, DXS10076, DXS10077, DXS10078, DXS7132, DXS10074, DXS981, DXS6800, DXS9898, DXS6801, DXS6809, DXS6789, DXS7424, DXS101, DXS6797, DXS7133, GATA172D05, HPRTB, DXS10101, DXS9908, DXS8377, DXS10134, DXS7423, DXS10011, DXS10102, DXS10103, DXS10104, DXS10105, DXS10106, or DXS10107 wherein at least one primer of each primer pair is labeled, and wherein at least six different labels are used, are amplified in a multiplex set.

In some embodiments, primer pairs for at least five of the 13 CODIS loci (i.e., CSF1PO, D3S1358, D5S818, D7S820, D8S1179, D13S317, D16S539, D18S51, D21S11, FGA, TH01, TPOX, vWA) and at least one Y-marker are incorporated into the multiplex. In yet another embodiment, primer pairs for at least five of the 13 CODIS loci, at least one Y-marker, and two or more markers from the group including D1S1656, D2S441, D2S1338, D6S1043, D10S1248, D12S391, D19S433, Penta B, Penta C, Penta D, Penta E, D22S1045, and SE33 are incorporated into the multiplex. In these embodiments, a total of 5, 6, 7, 8, 9, 10, 11, 12, or more fluorescent dyes are utilized to label primers (one label per primer pair), and amelogenin or another marker for sex identification may optionally be included in the multiplex (this optional marker is distinct from the at least one Y-marker mentioned above).

In some embodiments, primer pairs for at least five of the 13 CODIS loci (i.e., CSF1PO, D3S1358, D5S818, D7S820, D8S1179, D13S317, D16S539, D18S51, D21S11, FGA, TH01, TPOX, vWA) and at least one X-marker are incorporated into the multiplex. In yet another embodiment, primer pairs for at least five of the 13 CODIS loci, at least one X-marker, and two or more markers from the group including D1S1656, D2S441, D2S1338, D6S1043, D10S1248, D12S391, D19S433, Penta B, Penta C, Penta D, Penta E, D22S1045, and SE33 are incorporated into the multiplex. In these embodiments, a total of 5, 6, 7, 8, 9, 10, 11, 12, or more fluorescent dyes are utilized to label primers (one label per primer pair), and amelogenin or another marker for sex identification may optionally be included in the multiplex (this optional marker is distinct from the at least one X-marker mentioned above).

In some embodiments, either the forward or reverse primers or both of a primer pair are uniquely labeled (e.g., with a fluorescent dye). In some embodiments, the label is a fluorescent dye. In some embodiments, the fluorescently-labeled amplicons are detected using a laser (e.g. a Sapphire 488 nm laser). An advantage of using a laser is that the sensitivity and limit of detection of the assay is improved dramatically as compared to, for example, a plate reader.

In some embodiments, the nucleic acid products are amplified in less than about 180 minutes, less than 120 minutes, less than 90 minutes, less than 80 minutes, less than 70 minutes, less than 60 minutes, less than 55 minutes, less than 50 minutes, less than 45 minutes, than 40 minutes, less than 35 minutes, less than 30 minutes, less than 25 minutes, than 20 minutes, less than 18 minutes, less than 17 minutes, less than 16 minutes, less than 15 minutes, than 14 minutes, less than 13 minutes, less than 12 minutes, less than 11 minutes, less than 10 minutes, less than 9 minutes, less than 8 minutes, less than 7 minutes, less than 5 minutes, or in less than about 4 minutes.

For the methods described in any of the embodiments provided herein, the reaction chamber can be on a microfluidic biochip (see for example, Giese et al. (2009). "Fast multiplexed polymerase chain reaction for conventional and microfluidic short tandem repeat analysis." *J Forensic Sci* 54(6): 1287-96). Furthermore, the reaction chamber may be on a fully-integrated microfluidic biochip capable of performing a complex series of processing steps for one or more samples in parallel in the setting of a sample-in to results out system in which there is no requirement for operator manipulation. In some embodiments, the methods comprise electrophoretically separating and detecting the nucleic acid products. In some embodiments, the separation and/or detection of the nucleic acid products is conducted on the microfluidic biochip.

In any of the embodiments described herein, the sample can comprise about 1 pg to more than 10 μg of the one or more nucleic acid(s) (template(s)). In some embodiments, the sample comprises less than 1 ng of the one or more nucleic acid(s) (template(s)). In certain aspects, the heterozygous peak height ratio (PHR) of each of the nucleic acid products is between 0.6 and 1.0 for nucleic acid template levels ranging from 0.05 ng to 4.0 ng.

Further aspects of the invention are directed to kits for rapid multiplex amplification of polymorphic loci, comprising: (a) salt, buffer, dNTPs, and polymerase; (b) a set of STR primer pairs selected from those described above, each primer pair having a forward primer and a reverse primer and hybridizing to one of at least six loci in the one or more nucleic acids or mixture of nucleic acids, wherein either the forward or reverse primer, or both, of each primer pair is labeled with a fluorescent dye; (c) components for rapid multiplex amplification of STR loci (e.g. salts, buffers, magnesium, dNTPS, and polymerase), wherein components (a), (b), and (c) are placed within a single reaction container.

In any of the embodiments described herein, any DNA polymerase may be utilized. Examples include *Thermus aquaticus* (Taq), *Pyrccoccus furiosus* (Pfu), *Pyrococcus woesei* (Pwo), *Thermas flavus* (Tfl), *Themus thermophilus* (Tth), *Thermus litoris* (Tli) and *Thermotoga maritime* (Tma). These enzymes, modified versions of these enzymes, and combination of enzymes, are commercially available from vendors including Roche, Invitrogen, Qiagen, Strategene, and Applied Biosystems. Representative enzymes include PHUSION (New England Biolabs, Ipswich, Mass.), Hot MasterTaq™ (Eppendorf), PHUSION Mpx (Finnzymes), PyroStart (Fermentas), KOD (EMD Biosciences), Z-Taq (TAKARA), and CS3AC/LA (KlenTaq, University City, Mo.).

The teachings of the invention can be applied to any approach to nucleic acid amplification including but not limited to multiplex end-point PCR, real-time PCR, reverse transcription PCR, asymmetric PCR, nested PCR, LATE PCR, touchdown PCR, digital PCR, isothermal PCR, rolling circle amplification, strand displacement amplification, and multiple displacement amplification.

The teachings of the invention can be applied to the analysis of any multiplexed loci that are characterized by varying allele sizes at given loci. Multiplexed STR analyses can be applied to a wide variety of organisms, including non-human mammals, fish, birds, reptile, and amphibian species. In addition, the invention can be utilized for the identification and characterization of bacteria (including pathogens) by Multiple Loci Variable Number Tandem Repeats Analysis (MLVA) and Amplified Fragment Length Polymorphism (AFLP) Analysis. These approaches are similar to STR analysis and also can be applied broadly to strain-typing and characterization in plants, fungi, and animals. The teachings of the invention can be applied to the analysis of loci that are not polymorphic, or combinations of loci that are and are not polymorphic. Finally, the invention is directly applicable to the multiplexed analysis of Single Nucleotide Polymorphisms (SNPs).

BRIEF DESCRIPTION OF THE DRAWINGS

FIG. 12A denotes the presence of two artifacts (under arrows) prior to artifact elimination in the context of a six-dye 26-locus multiplex amplification product displayed in 5 colors following separation on the GeneBench FX instrument. As used throughout the specification and drawing "ATTO™ 488" refers to a dye in the ATTO™ line of dyes which are proprietary to Atto-Tec GmbH.

FIG. 12C denotes the absence of two artifacts (under arrows) following artifact elimination in the context of a six-dye 26-locus multiplex amplification product displayed in 5 colors following separation on the GeneBench FX instrument.

FIG. 15A displays a design employing 5 dyes to evaluate the CODIS 13 core STR loci.

FIG. 15B displays a design employing 6 dyes illustrating the smaller Multiplex Size Range required, and the larger Multiplex Density achieved to evaluate the CODIS 13 core STR loci.

FIG. 15C displays a design employing 8 dyes illustrating the smaller Multiplex Size required, and the larger Multiplex Density achieved to evaluate the CODIS 13 core STR loci.

The table included illustrates the numerical values of the Multiplex Size Range and Multiplex Density for the 5-dye, 6-dye, and 8-dye options.

Figure 16:
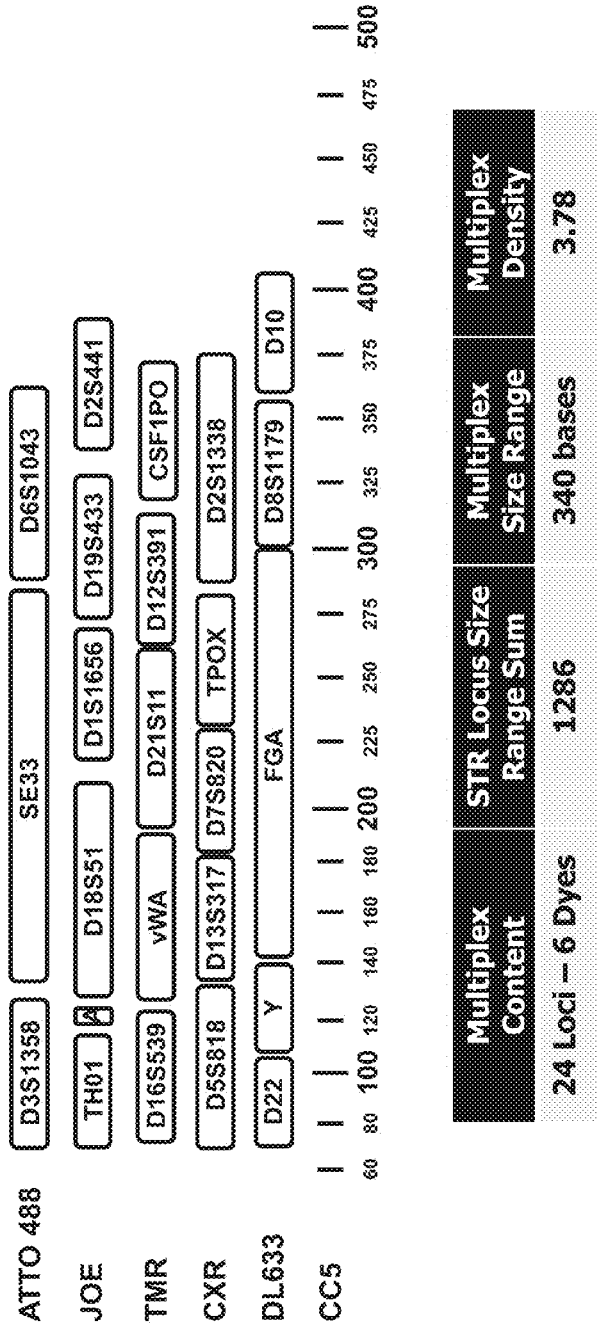
Figure 17:
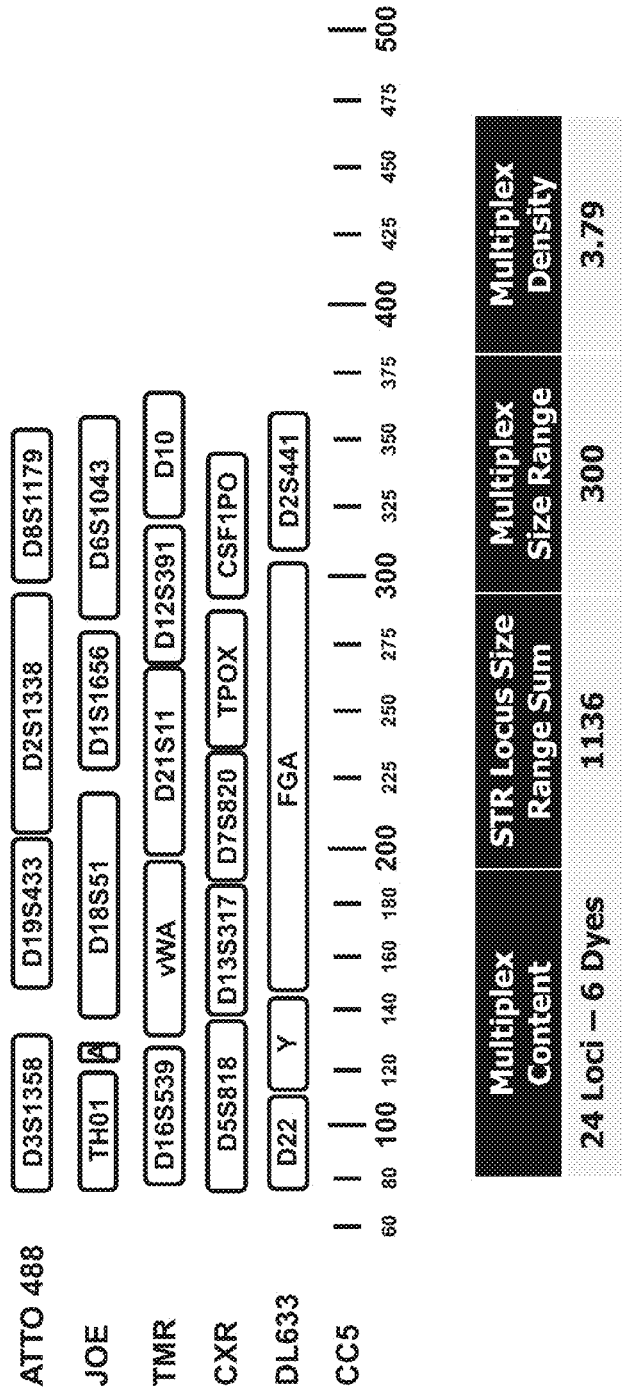
Figure 18:
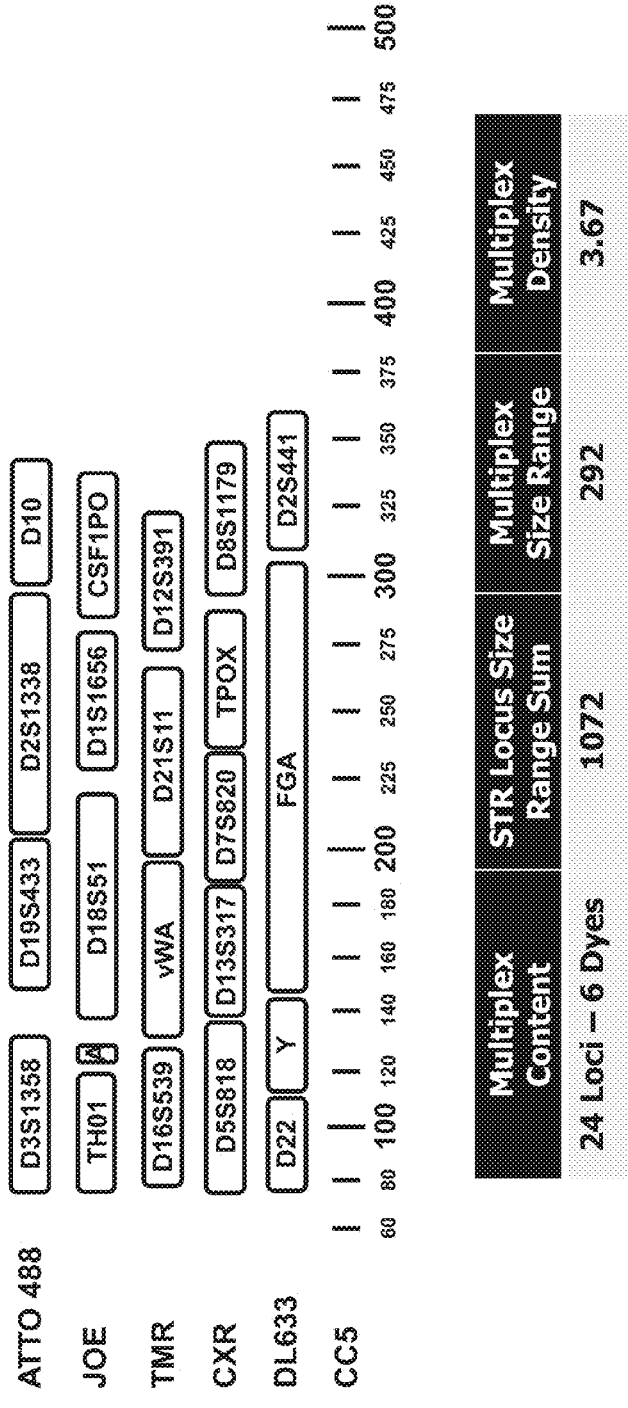
Figure 19:
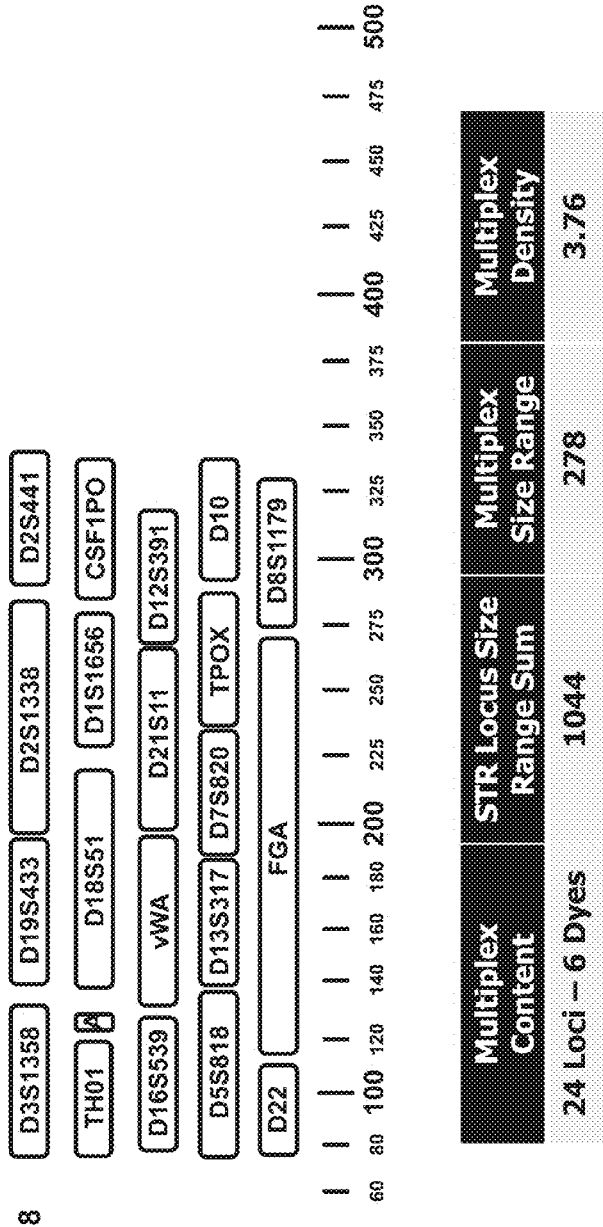

FIG. 16 displays a 24 locus amplification design.
FIG. 17 displays a 23 locus amplification design.
FIG. 18 displays a 22 locus amplification design.
FIG. 19 displays a 21 locus amplification design.

DETAILED DESCRIPTION OF THE INVENTION

Described herein are methods useful for genetic analysis. Some embodiments of the methods are designed to provide highly specific genetic profiles, for example short tandem repeat (STR) profiles, of one or more nucleic acid templates. Each profile provides a DNA "fingerprint" of multiple, polymorphic genomic loci within a given nucleic acid template, which can then be used in some embodiments to identify the individual (or information about the individual or blood relatives of the individual) from which the nucleic acid template was obtained.

It is an object of this invention to provide multiplexed STR assays that generate human identification information useful in a variety of applications. For example, forensic laboratories have recently identified increasing value in familial searching, i.e., searching for connections between the profile derived from a crime scene sample with profiles present in a state, national, or international database to aid an investigation by narrowing the list of potential suspects to family members of the individual whose profile is in the database. The assays of the invention provide substantially more confidence in familial searches and significantly diminish the number of adventitious matches obtained in searching databases of increasing size.

The greater discrimination power of the assays of the invention also strengthens use of DNA profiling in analysis of immigration and refugee applications. In these situations, U.S. State Department policy implementation related to rights of individuals related to a U.S. citizen or a specific refugee can be performed with greater confidence of correct results. While the 13 CODIS STR loci provide adequate assurance in testing parent-child relationships and sibling-sibling relationships, kinship analyses of more extended relationships such as grandparent-grandchild or aunt/uncle-nephew/niece lead to many results with limited confidence levels. Increasing the number of STR loci and/or selecting more polymorphic loci used for testing increases the strength of the likelihood ratios used in kinship analysis increasing confidence in the result and reduces risk of potential fraud. The assays of the invention also offer an advantage in evaluation of degraded DNA samples sometimes obtained from forensic samples.

Although STR analysis has become an evidentiary gold standard, the set of STR loci has not been standardized internationally. In the United States, the Federal Bureau of Investigation selected 13 STR loci and the amelogenin locus (for gender determination) for use in conjunction with the Combined DNA Index System (CODIS). The US set is often referred to as the "CODIS core loci" and consists of STR loci CSF1PO, FGA, THO1, TPOX, VWA, D3S1358, D5S818, D7S820, D8S1179, D13S317, D16S539, D18S51, and D21S11. In general, each STR locus is named for the chromosome on which it is found (e.g. D3S1358 is located on human chromosome 3) or for a nearby gene (e.g. CSF1PO is located within an intron of the gene encoding the human c-fms proto-oncogene receptor for Colony Stimulating Factor-1 receptor gene). The United Kingdom core loci are FGA, TH01, VWA, D2S1338, D3S1358, D8S1179, D16S539, D18S51, D19S433, D21S11, and amelogenin. The European Core loci are FGA, ThO1, VWA, D1S1656, D2S441, D3S1358, D8S1179, D10S1248, D12S391, D18S51, D21S11, D22S1045, and amelogenin. The Austrian government adds D2S1338, D16S539, and D19S433 to the European core loci, and the German government adds locus SE33. The locus D6S1043 is often utilized in China in combination with STR loci CSF1PO, FGA, vWA, D2S1338, D3S1358, D5S818, D7S820, D8S1179, D12S391, D13S317, D16S539, D18S51, D19S433, D21S11 and amelogenin. The Interpol Standard Set loci are FGA, TH01, VWA, D3S1358, D8S1179, D18S51, D21S11, and optionally amelogenin.

The invention provides STR assays that simultaneously interrogate all STR loci selected for inclusion in national databases around the world and subsets containing these loci. Such an international STR standard set will dramatically improve effective cooperation among nations to improve societal safety. A one skilled in the art will appreciate, when designing and constructing a multiplex STR assay, many factors must be balanced. These factors become more difficult to balance, particularly as the number of STR loci in the assay increases beyond 18. Factors that must be balanced include the prevention or removal of STR artifacts (e.g. iNTA, and products of unintended insteractions of two or more primers with sample nucleic acid), absolute and relative signal strength, reaction efficiency and time, STR locus overlap, STR amplicon resolution, STR Locus Size Range and the tolerable degree of overlap, STR locus heterozygosity, the number of fluorescent dye labels utilized in the reaction, Multiplex Size Range, and the specifications and performance of the instrument or instruments performing the reactions. These factors have prevented STR assays from moving above 18 formal loci in a single, simultaneous reaction with a Multiplex Density of greater than approximately 3.15 and an STR Locus Size Range Sum of 1022. Depending on the desired outcome, these tools and teachings may be applied to allow much larger numbers of formal loci to be incorporated into STR multiplexes, and much greater Multiplex Densities and STR Locus Size Range Sums to be achieved.

The terms "STR locus" and "STR loci," as used herein, mean a nucleotide sequence consisting of a repeating pattern of two or more nucleotides at a given locus of a target nucleic acid. The repeating pattern can range in length from about 2 to about 10 base pairs (bp), and is typically in the non-coding intron region. The repeating pattern may contain intervening sequences that do not correspond to the repeat unit, or may contain more than one repeating pattern.

The terms "STR allele" or "allele," as used herein, refer to a form of an STR locus found in the genome of an individual. A given STR locus may be heterozygous, meaning that the two alleles (one inherited from each biological parent) are of different lengths and base pair composition, or may be homozygous, meaning that both alleles are of identical length (and usually but not always base pair composition). Rarely, an individual may have three or more alleles for a given STR locus. Occasionally, an individual's alleles at a given STR locus may differ from his or her parents due to one or more mutations.

The term "allelic ladder," as used herein, refers to a set of DNAs of lengths corresponding to the common alleles that have been observed for each STR locus. Different commercial STR kits have different alleles in the allelic ladders representing each locus.

The term "STR locus size range" or "locus size range," as used herein, refers to the size range of common alleles observed in the population. Uncommon alleles may not have been observed given any particular number of DNA samples having been tested or observed in one or a few individuals of the tens of millions tested. As commercial kits have differing size ranges (companies tend to add rare alleles to their allelic ladders over time), it is important to define an STR locus size range for all STR loci of interest. Such a definition allows various STR assays to be compared to one another. Uncommon alleles may not have been available for inclusion in any particular allelic ladder or may not have been included for convenience. It is not necessary that an allelic ladder contain all known alleles as additional alleles can be identified by size comparison with existing allelic ladder components. The size difference between the largest and smallest alleles for each locus in a set of commercially available allelic ladders is used to define standard STR locus size ranges and is presented in Table 1. The STR locus size ranges included in the following comparisons were determined by comparison of the commercially published technical materials available on line for the Applied Biosystems® products AmpFISTR® Identifiler®, AmpFISTR® Identifiler Plus®, AmpFISTR® Identifiler Direct®, AmpF1STR® NGM Select™, AmpFISTR® Sinofiler™, and Promega® Corporation products PowerPlex® 16 HS, PowerPlex® ESX 17, and PowerPlex® 18D. For each locus, the largest and smallest allele among the combined set of commercially available allelic ladders described in the aforesaid technical materials was determined. Then the size difference, in bases, between the largest and smallest alleles was determined based on the number of repeats, and whether four- or five-base repeat length is present at the locus. One value, called the "Locus Standard Size Range" for that locus, was assigned for each locus. These individual values were used to determine the "multilocus size range sum" (i.e., the sum of all the standard size ranges for the individual loci contained within each multiplex).

The STR loci of Table 1 can be grouped into four categories: 1) loci that are officially endorsed by one or more countries: CSF1PO, FGA, THO1, TPOX, VWA, D1S1656, D2S441, D2S1338, D3S1358, D5S818, D7S820, D8S1179, D10S1248, D12S391, D13S317, D16S539, D18S51, D19S433, D21S11, D22S1045, SE33, and amelogenin; 2) a locus widely used in China: D6S1043; 3) a locus proposed for use in the US: DYS391; and 4) three loci used in commercial STR kits: Penta B, C, D, and E. Taken together, any STR locus contained within these four categories is termed a "Formal STR Locus." In general, loci currently in these categories have been subjected to rigorous validation and testing. Over time, new loci may be added to the categories above: 1) new loci that are officially endorsed by one or more countries; 2) a new locus widely used in one or more countries but not officially endorsed; 3) new loci proposed for use in the US; and 4) new loci found in commercial kits. For new loci that later become members of one of these categories, published limits of the largest and smallest alleles for the locus can be used to define the size range for each STR locus. For "Informal" STR loci that do not fall into one of these four categories, published limits of the largest and smallest alleles for the locus can be used to define the size range for each STR locus.

TABLE 1

| | CSF1PO | D1S1656 | D2S441 | D2S1338 | D3S1358 | D5S818 | D6S1043 | D7S820 | D8S1179 |
|---|---|---|---|---|---|---|---|---|---|
| Locus Standard Size Range | 36 | 47 | 36 | 72 | 44 | 36 | 64 | 36 | 48 |

| | D10S1248 | D12S391 | D13S317 | D16S539 | D18S51 | D19S433 | D21S11 | D22S1045 | FGA |
|---|---|---|---|---|---|---|---|---|---|
| Locus Standard Size Range | 44 | 52 | 32 | 48 | 80 | 52 | 56 | 52 | 146 |

| | Penta B | PentaC | Penta D | Penta E | SE33 | TH01 | TPOX | vWA | DYS391 |
|---|---|---|---|---|---|---|---|---|---|
| Locus Standard Size Range | 70 | 55 | 73 | 95 | 150 | 43 | 28 | 56 | 28 |

The term "Substantially Non-overlapping STR Assay," as used herein, refers to an STR multiplex assay in which the alleles of the STR Locus Size Range do not overlap any other STR Locus Size Range of a locus labeled with the same dye (or other detection method as applicable) except for alleles that are extremely rare and that are outside the STR Locus Size Range.

The "STR Locus Size Range Sum," as used herein, refers to the sum of the individual STR locus size ranges for the loci included in a multiplex STR set. For example, the 26-locus STR set of Example I has an STR Locus Size Range Sum of 1487 bases and the 16-locus STR set of the Identifiler loci (Life Technologies) has an STR Locus Size Range Sum of 809 bases.

The "Multiplex Size Range," as used herein, refers to the difference in size of the largest allele in any locus of a given STR multiplex and the smallest allele in any locus of the multiplex. These two loci and the multiplex size range are characteristic of a specific multiplex. To calculate the multiplex size range: 1) identify the STR locus in the multiplex that contains the smallest common allele; 2) determine the size of the smallest common allele in said locus (using the same approach as described for "STR locus size range"; 3) identify the STR locus in the multiplex that contains the largest standard allele; 4) determine the size of the largest standard allele in said locus (using the same approach as described for "STR locus size range"; 5) Calculate the difference between the two standard alleles. For example, the 26-locus STR set of Example I has a multilocus size range of 411 bases and the 16-locus STR set of the Identifiler set (Life Technologies) has a multiplex size range of 257 bases.

Several factors impact the multiplex size range used in a given assay. STR alleles can be characterized using a variety of approaches including electrophoresis and mass spectrometry. For electrophoretic separation, for example, the lower size limit may be influenced by size at which it becomes difficult to distinguish short amplicons from STR primers, primer dimers, or other amplification artifacts. The higher size limit may be influenced by the resolution of the system with a diminished ability to resolve large alleles differing by one or a few bases. Similarly, the larger the alleles are in a given assay, the greater the possibility that a degraded DNA sample will not have an average fragment length sufficient to permit amplification of said large alleles in abundance.

For MALDI-TOF (matrix-assisted laser desorption/ionization Time-of-flight) mass spectrometry, size of the STR fragments are based on pulsing a sample containing the fragments with a laser and measuring the time-of-flight to the detector in comparison to mass standards. The higher size limit may be influenced by the inability of the mass spectrophotometer to detect or resolve STR alleles. Note that MALDI-TOF generates a precise molecular weight of the STR fragments and therefore does not require an allelic ladder. To allow direct comparisons to electrophoresis-based methods, the STR Locus Size Range Sum, Multiplex Size Range, and Multiplex Density are calculated as described above. Due to the increased accuracy with mass spectrometry, STR alleles may be reliably typed without comparison to allelic ladders. An absolute mass is measured with mass spectrometry rather than a relative mobility measurement (in comparison to DNA sizing standards) as in an electrophoretic analysis. GeneTrace-designed genotyping software then correlates the observed peak mass back to a genotype based on expected allele masses obtained from a reference sequence, the PCR primer positions, and the repeat unit mass. Each sample can be processed and genotyped in approximately one second using a standard desktop personal computer.

The "multiplex density," as used herein is defined as the "STR locus size range sum" divided by the "multiplex size range". This value is a measure of the density of STR information that can be obtained from a given multiplex. A higher value indicates that the multiplex displays a greater range of alleles in the limited size range permitted for detection. For example, Table 2 displays the Total Number of STR Loci, Number of Formal STR Loci, Dye Number, Multiplex Size Range, Multiplex Size Range Sum, and Multiplex Density for several STR sets. The Table also includes Locus Standard Size Ranges and the underlying data that allowed these values to be determined. The STR sets of the invention have multiplex densities of at least 2 or greater, 2.25 or greater, 2.5 or greater, 2.75 or greater, 2.93, or greater, 3.00 or greater, 3.1 or greater, 3.2 or greater, 3.3 or greater, 3.4 or greater, 3.5 of greater, 3.6 or greater, 3.7 or greater, 3.8 or greater, 3.9 or greater, 4.0 or greater, 4.1 or greater, 4.2 or greater, 4.3 or greater, 4.4 or greater, 4.5 or greater, 5 or greater, 6 or greater, 7 or greate, 8 or greater, 9 or greater, or ten or greater.

TABLE 2

| | NUMBER OF DYES USED (INCLUDING SIZE MARKER) | TOTAL NUMBER OF STR LOCI | FORMAL STR LOCI | STR LOCUS SIZE RANGE SUM | MULTI-PLEX SIZE RANGE | MULTI-PLEX DENSITY | CSF1PO | D1S1656 | D2S441 |
|---|---|---|---|---|---|---|---|---|---|
| | | | | | | | 36 | 47 | 36 |
| HILL, BUTLER, AND VALLONE (2009) A 26plex autosomal STR assay to aid human identity testing J FORENSIC SCIENCES 54: 1008-1015 | | | | | | | | | |
| PowerPlex 16 HS | 5 | 26 | 3 | 792 | 325 | 2.44 | | | 36 |
| APPLIED BIOSYSTEMS, INC. MULTIPLEX PRODUCTS | | | | | | | | | |
| Identifiler | 5 | 15 | 15 | 809 | 257 | 3.15 | 36 | | |
| Identifiler Plus | 5 | 15 | 15 | 809 | 258 | 3.14 | 36 | | |
| Identifiler Direct | 5 | 15 | 15 | 809 | 258 | 3.14 | 36 | | |
| NGM SElect | 5 | 16 | 16 | 1022 | 368 | 2.78 | | 47 | 36 |
| AB Sinofiler | 5 | 14 | 14 | 798 | 257 | 3.11 | 36 | | |
| PROMEGA CORPORATION MULTIPLEX PRODUCTS | | | | | | | | | |
| PowerPlex 16 HS | 4 | 15 | 15 | 853 | 359 | 2.38 | 36 | | |
| PowerPlex ESX 17 | 5 | 16 | 16 | 1022 | 359 | 2.85 | | 47 | 36 |
| PowerPlex 18D | 5 | 17 | 17 | 981 | 359 | 2.73 | 36 | | |
| QIAGEN MULTIPLEX PRODUCTS | | | | | | | | | |
| Investigator IDplex | 5 | 16 | 16 | 813 | 344 | 2.36 | 36 | | |
| Investigator ESSplex SE | 5 | 16 | 16 | 1026 | 376 | 2.73 | | 47 | 36 |
| Investigator Argus X-12 | 5 | 12 | 0 | 647 | 285 | 2.27 | | | |
| Investigator Argus Y-12 QS | 4 | 11 | 0 | 296 | 196 | 1.51 | | | |
| BIOTYPE MULTIPLEX PRODUCTS | | | | | | | | | |
| Mentype Nonaplex I | 4 | 8 | 8 | 623 | 231 | 2.70 | | | |
| EXAMPLES OF THE INVENTION | | | | | | | | | |
| Example 1, FIG. 1 | 5 | 25 | 25 | 1487 | 411 | 3.62 | 36 | 47 | 36 |
| Example 2, FIG. 4 | 6 | 25 | 25 | 1487 | 411 | 3.62 | 36 | 47 | 36 |
| Example 3, FIG. 5 | 8 | 35 | 35 | 1907 | 411 | 4.64 | 36 | 47 | 36 |
| Example 4, FIG. 6 | 8 | 37 | 37 | 1976 | 411 | 4.81 | 36 | 47 | 36 |
| Example 5, FIG. 7 | 6 | 26 | 26 | 1509 | 387 | 3.90 | 36 | 47 | |
| Example 14, FIG. 15A | 5 | 13 | 13 | 689 | 235 | 2.93 | 36 | | |
| Example 14, FIG. 15B | 6 | 13 | 13 | 689 | 205 | 3.36 | 36 | | |
| Example 14, FIG. 15C | 8 | 13 | 13 | 689 | 160 | 4.31 | 36 | | |
| Example 15, FIG. 16 | 6 | 26 | 26 | 1286 | 340 | 3.78 | 36 | 47 | 36 |
| Example 16, FIG. 17 | 6 | 26 | 26 | 1136 | 300 | 3.79 | 36 | 47 | 36 |
| Example 17, FIG. 18 | 6 | 26 | 26 | 1072 | 292 | 3.67 | 36 | 47 | 36 |
| Example 18, FIG. 19 | 6 | 26 | 26 | 1044 | 278 | 3.76 | 36 | 47 | 36 |

| | D2S1338 | D3S1358 | D5S818 | D6S1043 | D7S820 | D8S1179 | D10S1248 | D12S391 | D13S317 | D16S539 | D18S51 |
|---|---|---|---|---|---|---|---|---|---|---|---|
| LOCUS STANDARD SIZE RANGES | | | | | | | | | | | |
| | 72 | 44 | 36 | 64 | 36 | 48 | 44 | 52 | 32 | 48 | 80 |
| HILL, BUTLER, AND VALLONE (2009) A 26plex autosomal STR assay to aid human identity testing J FORENSIC SCIENCES 54: 1008-1015 | | | | | | | | | | | |
| PowerPlex 16 HS | | | | | | | | | | 44 | |
| APPLIED BIOSYSTEMS, INC. MULTIPLEX PRODUCTS | | | | | | | | | | | |
| Identifiler | 72 | 44 | 36 | | 36 | 44 | | | 32 | 48 | 80 |
| Identifiler Plus | 72 | 44 | 36 | | 36 | 44 | | | 32 | 48 | 80 |
| Identifiler Direct | 72 | 44 | 36 | | 36 | 44 | | | 32 | 48 | 80 |
| NGM SElect | 72 | 44 | | | | 44 | 44 | 52 | | 48 | 80 |
| AB Sinofiler | 72 | 44 | 36 | 64 | 36 | 44 | | 52 | 32 | 48 | 80 |
| PROMEGA CORPORATION MULTIPLEX PRODUCTS | | | | | | | | | | | |
| PowerPlex 16 HS | | 44 | 36 | | 36 | 44 | | | 32 | 48 | 80 |
| PowerPlex ESX 17 | 72 | 44 | | | | 44 | 44 | 52 | | 48 | 80 |
| PowerPlex 18D | 72 | 44 | 36 | | 36 | 48 | | | 32 | 48 | 80 |

TABLE 2-continued

QIAGEN MULTIPLEX PRODUCTS

| | | | | | | | | | | |
|---|---|---|---|---|---|---|---|---|---|---|
| Investigator IDplex | 72 | 44 | 36 | | 36 | 48 | | | 32 | 48 | 80 |
| Investigator ESSplex SE | 72 | 44 | | | | 48 | 44 | 52 | | 48 | 80 |
| Investigator Argus X-12 | | | | | | | | | | | |
| Investigator Argus Y-12 QS | | | | | | | | | | | |

BIOTYPE MULTIPLEX PRODUCTS

| | | | | | | | | | | |
|---|---|---|---|---|---|---|---|---|---|---|
| Mentype Nonaplex I | | 44 | | | | 48 | | | | | 80 |

EXAMPLES OF THE INVENTION

Figure 1:
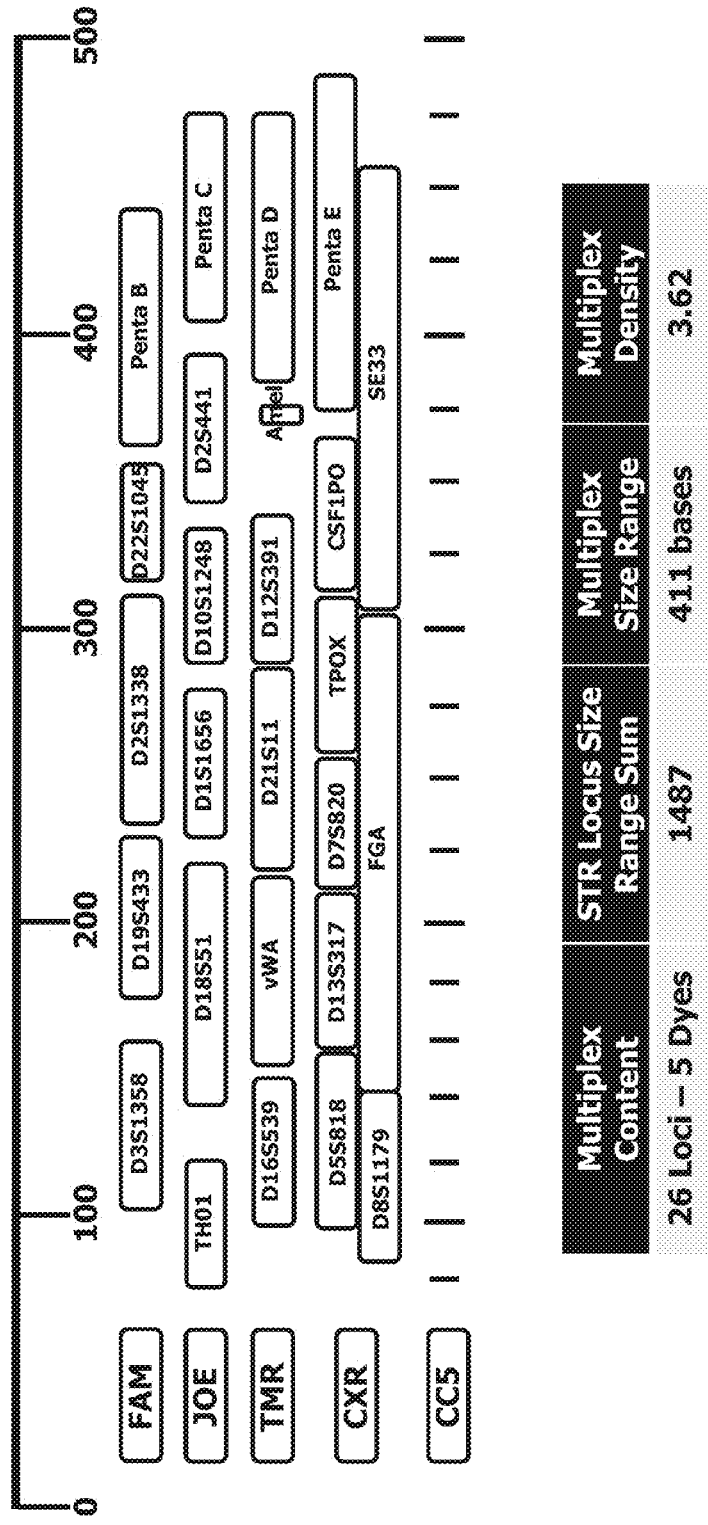
FIG. 1 Design of 5-color 26-locus, 25-STR formal locus. As used throughout the specification and drawing, FAM™, JOE™, and TMR (referring to TAMARA™) are trademarks of ThermoFisherScientific. CXR™ and CC5™ are trademarks of Promega Corporation. Additional trademarks of ThermoFisherScientific referred to herein include, JOE™, VIC®, HEX™, NED™, PET®, ROX™, TET™, LIZ™, DyLight®), HyLight™.
Figure 4:
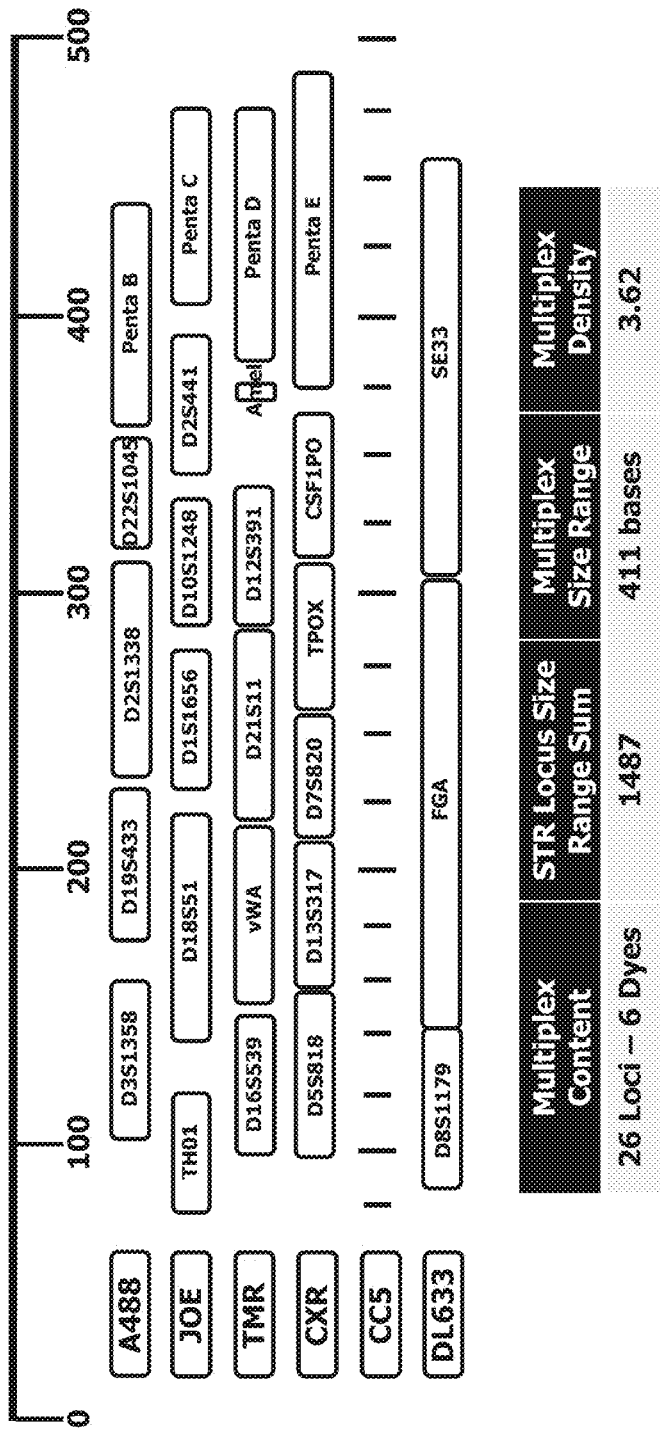
FIG. 4 illustrates a design of a 25-STR locus Substantially Non-overlapping STR Assay.
Figure 5:
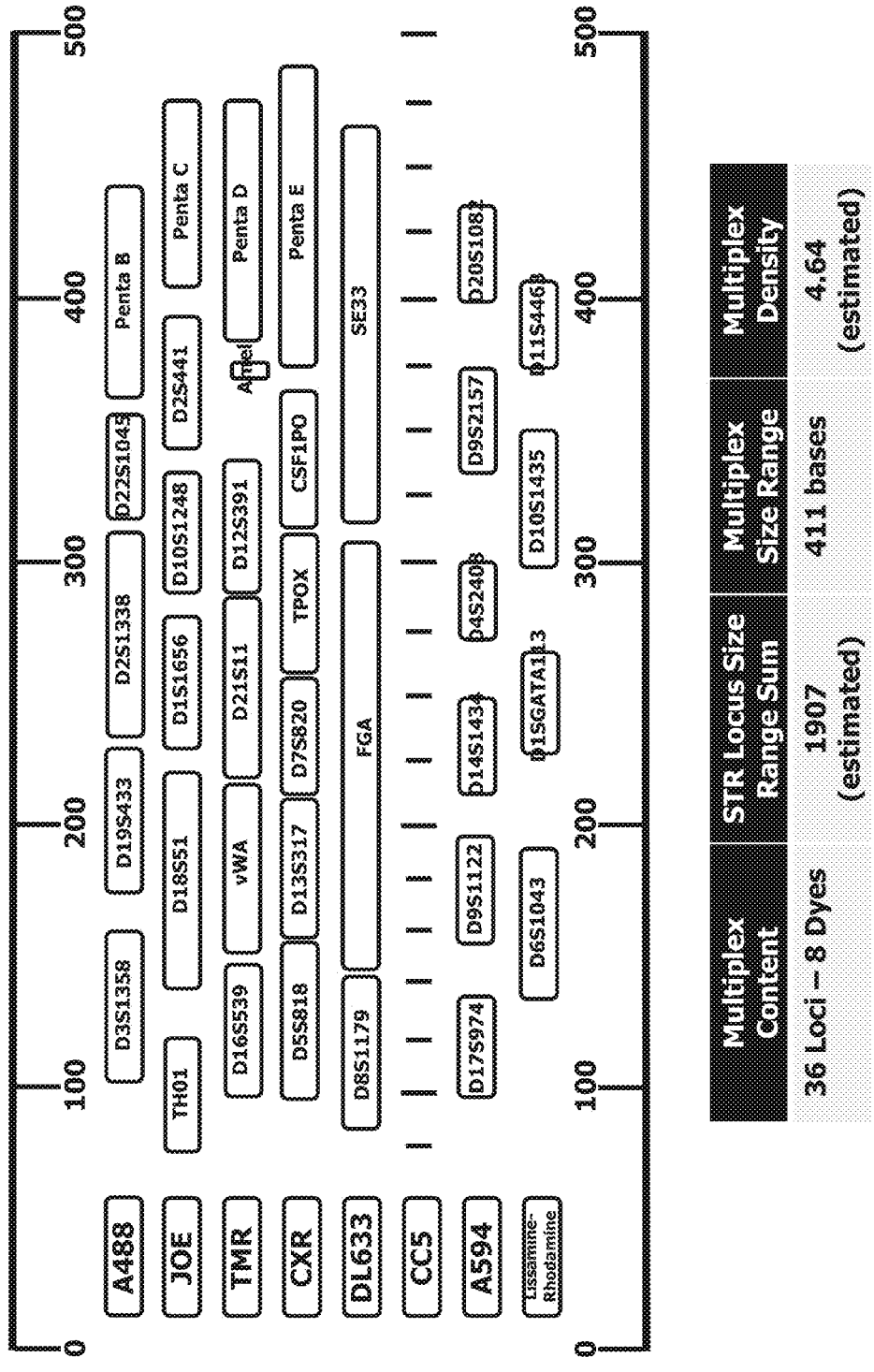
FIG. 5 displays the design employing 8 dyes to label products of amplified sets of loci. As used throughout the specification and drawing "A594" refers to ATTO™ 594. The ATTO™ line of dyes are proprietary to Atto-Tec GmbH.
Figure 6:
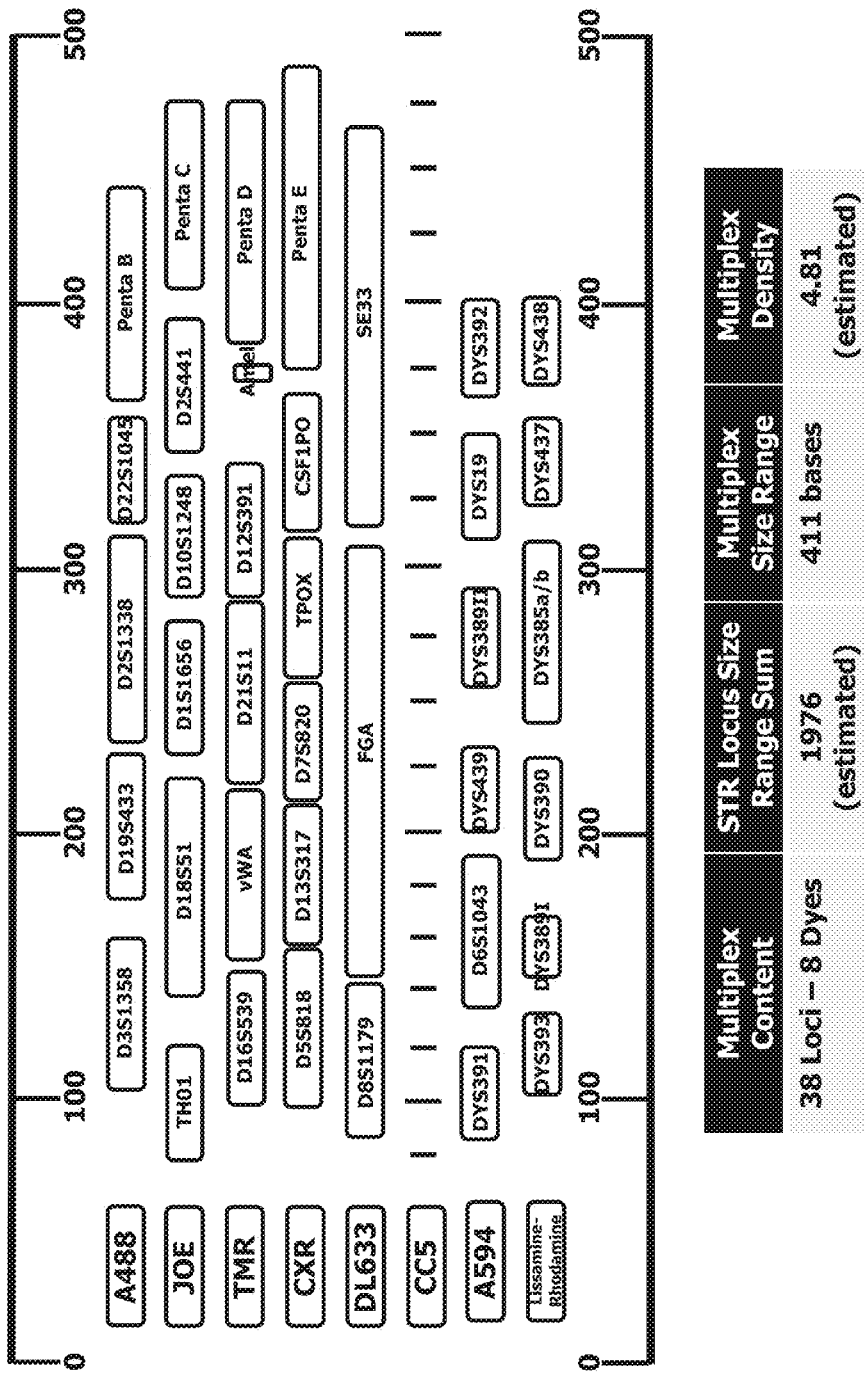
FIG. 6 displays the design employing 8 dyes to label products of amplified sets of autosomal STR and Y STR loci. As used herein "A594" refers to ATTO™ 594.
Figure 7:
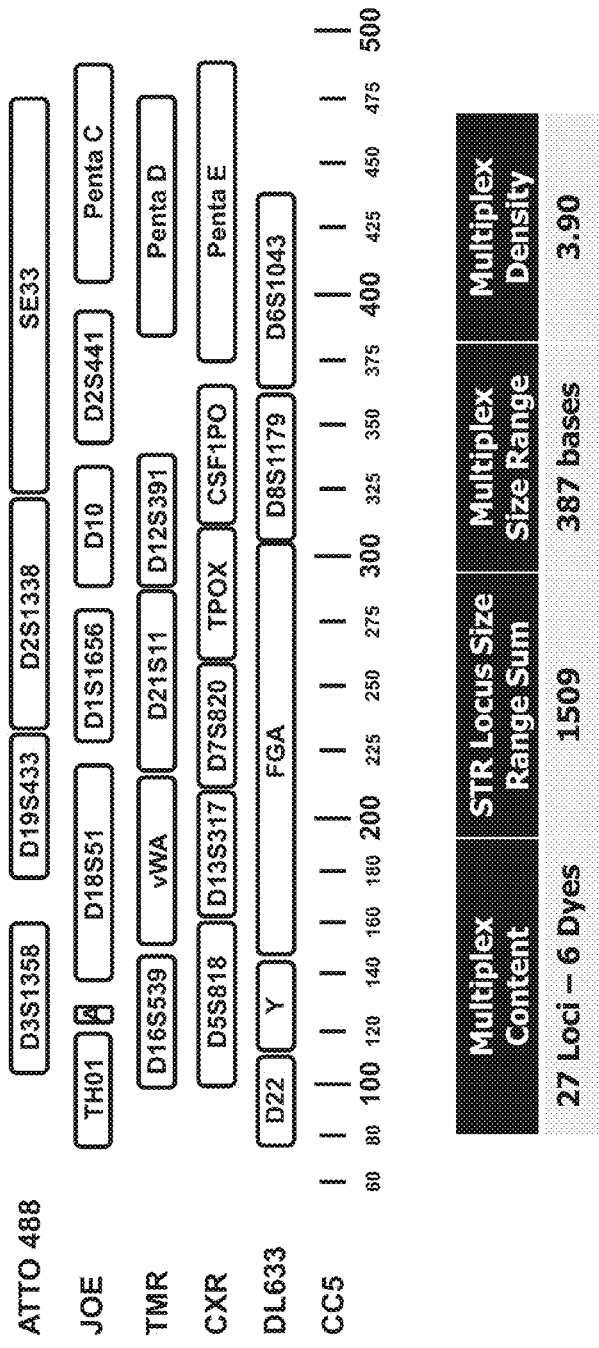
FIG. 7 illustrates the design permitting co-amplification of 26 STR loci and the amelogenin locus in a single reaction.

| | | | | | | | | | | |
|---|---|---|---|---|---|---|---|---|---|---|
| Example 1, FIG. 1 | 72 | 44 | 36 | | 36 | 48 | 44 | 52 | 32 | 48 | 80 |
| Example 2, FIG. 4 | 72 | 44 | 36 | | 36 | 48 | 44 | 52 | 32 | 48 | 80 |
| Example 3, FIG. 5 | 72 | 44 | 36 | | 36 | 48 | 44 | 52 | 32 | 48 | 80 |
| Example 4, FIG. 6 | 72 | 44 | 36 | | 36 | 48 | 44 | 52 | 32 | 48 | 80 |
| Example 5, FIG. 7 | 72 | 44 | 36 | 64 | 36 | 48 | 44 | 52 | 32 | 48 | 80 |
| Example 14, FIG. 15A | | 44 | 36 | | 36 | 48 | | | 32 | 48 | 80 |
| Example 14, FIG. 15B | | 44 | 36 | | 36 | 48 | | | 32 | 48 | 80 |
| Example 14, FIG. 15C | | 44 | 36 | | 36 | 48 | | | 32 | 48 | 80 |
| Example 15, FIG. 16 | 72 | 44 | 36 | 64 | 36 | 48 | 44 | 52 | 32 | 48 | 80 |
| Example 16, FIG. 17 | 72 | 44 | 36 | 64 | 36 | 48 | 44 | 52 | 32 | 48 | 80 |
| Example 17, FIG. 18 | 72 | 44 | 36 | | 36 | 48 | 44 | 52 | 32 | 48 | 80 |
| Example 18, FIG. 19 | 72 | 44 | 36 | | 36 | 48 | 44 | 52 | 32 | 48 | 80 |

| | D19S433 | D21S11 | D22S1045 | FGA | Penta B | PentaC | Penta D | Penta E | SE33 | TH01 | TPOX | vWA | DYS391 |
|---|---|---|---|---|---|---|---|---|---|---|---|---|---|
| LOCUS STANDARD SIZE RANGES | 52 | 56 | 52 | 146 | 70 | 55 | 73 | 95 | 150 | 43 | 28 | 56 | 28 |

HILL, BUTLER, AND VALLONE (2009) A 26plex autosomal STR assay
to aid human identity testing J FORENSIC SCIENCES 54: 1008-1015

| | | | | | | | | | | | | | |
|---|---|---|---|---|---|---|---|---|---|---|---|---|---|
| PowerPlex 16 HS | | | 52 | | | | | | | | | | |

APPLIED BIOSYSTEMS, INC. MULTIPLEX PRODUCTS

| | D19S433 | D21S11 | D22S1045 | FGA | Penta B | PentaC | Penta D | Penta E | SE33 | TH01 | TPOX | vWA | DYS391 |
|---|---|---|---|---|---|---|---|---|---|---|---|---|---|
| Identifiler | 52 | 56 | | 146 | | | | | | 43 | 28 | 56 | |
| Identifiler Plus | 52 | 56 | | 146 | | | | | | 43 | 28 | 56 | |
| Identifiler Direct | 52 | 56 | | 146 | | | | | | 43 | 28 | 56 | |
| NGM SElect | 52 | 56 | 52 | 146 | | | | | 150 | 43 | | 56 | |
| AB Sinofiler | 52 | 56 | | 146 | | | | | | 43 | | 56 | |

PROMEGA CORPORATION MULTIPLEX PRODUCTS

| | D19S433 | D21S11 | D22S1045 | FGA | Penta B | PentaC | Penta D | Penta E | SE33 | TH01 | TPOX | vWA | DYS391 |
|---|---|---|---|---|---|---|---|---|---|---|---|---|---|
| PowerPlex 16 HS | | 56 | | 146 | | | 73 | 95 | | 43 | 28 | 56 | |
| PowerPlex ESX 17 | 52 | 56 | 52 | 146 | | | | | 150 | 43 | | 56 | |
| PowerPlex 18D | 52 | 56 | | 146 | | | 73 | 95 | | 43 | 28 | 56 | |

QIAGEN MULTIPLEX PRODUCTS

| | D19S433 | D21S11 | D22S1045 | FGA | Penta B | PentaC | Penta D | Penta E | SE33 | TH01 | TPOX | vWA | DYS391 |
|---|---|---|---|---|---|---|---|---|---|---|---|---|---|
| Investigator IDplex | 52 | 56 | | 146 | | | | | | 43 | 28 | 56 | |
| Investigator ESSplex SE | 52 | 56 | 52 | 146 | | | | | 150 | 43 | | 56 | |
| Investigator Argus X-12 | | | | | | | | | | | | | |
| Investigator Argus Y-12 QS | | | | | | | | | | | | | |

BIOTYPE MULTIPLEX PRODUCTS

| | D19S433 | D21S11 | D22S1045 | FGA | Penta B | PentaC | Penta D | Penta E | SE33 | TH01 | TPOX | vWA | DYS391 |
|---|---|---|---|---|---|---|---|---|---|---|---|---|---|
| Mentype Nonaplex I | | 56 | | 146 | | | | | 150 | 43 | | 56 | |

EXAMPLES OF THE INVENTION

| | D19S433 | D21S11 | D22S1045 | FGA | Penta B | PentaC | Penta D | Penta E | SE33 | TH01 | TPOX | vWA | DYS391 |
|---|---|---|---|---|---|---|---|---|---|---|---|---|---|
| Example 1, FIG. 1 | 52 | 56 | 52 | 146 | 70 | 55 | 73 | 95 | 150 | 43 | 28 | 56 | |
| Example 2, FIG. 4 | 52 | 56 | 52 | 146 | 70 | 55 | 73 | 95 | 150 | 43 | 28 | 56 | |
| Example 3, FIG. 5 | 52 | 56 | 52 | 146 | 70 | 55 | 73 | 95 | 150 | 43 | 28 | 56 | |
| Example 4, FIG. 6 | 52 | 56 | 52 | 146 | 70 | 55 | 73 | 95 | 150 | 43 | 28 | 56 | |
| Example 5, FIG. 7 | 52 | 56 | 52 | 146 | | 55 | 73 | 95 | 150 | 43 | 28 | 56 | 28 |
| Example 14, FIG. 15A | | 56 | | 146 | | | | | | 43 | 28 | 56 | |
| Example 14, FIG. 15B | | 56 | | 146 | | | | | | 43 | 28 | 56 | |

TABLE 2-continued

| Example | | | | | | | | | |
|---|---|---|---|---|---|---|---|---|---|
| Example 14, FIG. 15C | | 56 | | 146 | | 43 | 28 | 56 | |
| Example 15, FIG. 16 | 52 | 56 | 52 | 146 | 150 | 43 | 28 | 56 | 28 |
| Example 16, FIG. 17 | 52 | 56 | 52 | 146 | | 43 | 28 | 56 | 28 |
| Example 17, FIG. 18 | 52 | 56 | 52 | 146 | | 43 | 28 | 56 | 28 |
| Example 18, FIG. 19 | 52 | 56 | 52 | 146 | | 43 | 28 | 56 | |

The terms "nucleic acid template" or "nucleic acid templates," as used herein, refer to a nucleic acid or nucleic acids that serve as starting material for the synthesis of an STR profile. Nucleic acid template(s) may be double stranded or single stranded. The templates can comprise DNA from one or more whole genomes of an individual, partial genomes of an individual, or previously amplified products from DNA of the individual and can comprise mixtures of whole and partial genomes from two or more individuals. The genomes to be analyzed may be derived from humans, from other mammalian species, or from mixtures.

The terms "locus" and "loci" (plural), as used herein, mean one or more specific positions within the whole or partial genomes of a given species, as defined herein.

The terms "highly polymorphic locus" or "highly polymorphic loci", as used herein, refer to a locus (loci, each of which) having a polymorphic information content of at least 0.5. Polymorphic information content (PIC) [Botstein D, White R L, Skolnick M, and Davis R W, 1980. Am J Hum Genet 32:314-331, the disclosure of which is incorporated herein], each of which is known to one of ordinary skill in the art. The following equation can be used to calculate the PIC of a particular locus:

$$PIC = 1 - \Sigma_{i=1}^{n} p_i^2 - 2|\Sigma_{i=1}^{n-1} \Sigma_{j=i+1}^{n} p_i^2 p_j^2|,$$

where $p_i$ is the frequency of the $i^{th}$ allele, and n is the number of alleles. In some embodiments, a highly polymorphic locus has a PIC value of about 0.5, or greater. In some embodiments, a highly polymorphic locus has a PIC value of about 0.5 to about 0.7. In some embodiments, the methods described herein are used to amplify two or more highly polymorphic loci, while in other embodiments, the methods are used to amplify a mixture of polymorphic (PIC<0.4) and highly polymorphic (PIC≥0.5) loci.

The methods in some embodiments described herein provide rapid, substantially simultaneous polymerase chain reaction (PCR) amplification of six or more polymorphic loci, some of which may be highly polymorphic, in a nucleic acid sample, all of which will be detected by laser induced fluorescence. In some embodiments, up to 35 or more polymorphic loci are amplified. Some of the loci in the multiplexes of the invention may not be highly polymorphic. For example, a locus for a physical trait, a disease, a locus related to geoethnicity, or a locus included for its common use might be present with minimal polymorphism. In the multiplexes of the example, the amelogenin locus is not highly polymorphic. The term "substantially simultaneous," as used herein, refers to an immediate or nearly immediate succession in time.

Methods described provide for rapid amplification of the STR loci. In some embodiments, the methods described herein provide for rapid PCR amplification polymorphic loci from a sample comprised of at least 0.006 ng of human genomic DNA in about 45 minutes or less, or about 20 minutes or less. In other embodiments, multiple polymorphic loci are amplified in about 100 minutes or less. In yet other embodiments, multiple polymorphic loci are amplified in about 80 minutes or less, about 70 minutes or less, about 60 minutes or less, about 50 minutes or less, about 40 minutes or less, about 30 minutes or less, or about 20 minutes or less. In still other embodiments, multiple STR loci are amplified in about 1 minute to about 10 minutes.

In some embodiments, multiple polymorphic loci can be amplified starting from at least one copy of the target nucleic acid loci. For example, a sample (or nucleic acid template) to be analyzed can comprise less than 10,000 copies, less than 1000 copies, less than 400 copies, less than 200 copies, less than 100 copies, less than 50 copies, less than 30 copies, less than 10 copies, less than 6 copies, or at least 1 copy of a target nucleic acid prior to the multiplex amplification reaction. In addition, less than a single genome equivalent of DNA can be utilized for amplification if one of the target nucleic acid loci is present in one copy in the genome, or a target nucleic acid locus is present in more than one copy in the genome. In some embodiments, at least two loci, and up to approximately 250 loci can be simultaneously amplified within each target nucleic acid in a sample according to some embodiments of the methods described herein. In some embodiments, approximately 26 or 27 polymorphic (or highly polymorphic) loci are simultaneously amplified. In other embodiments, at least two loci and up to approximately 250 loci can be simultaneously amplified from one or multiple target nucleic acids, each obtained from different sources or the same source.

The target nucleic acids utilized herein can be any nucleic acid, for example, human nucleic acids, bacterial nucleic acids, or viral nucleic acids. The target nucleic acid sample can be, for example, a nucleic acid sample from one or more cells, tissues, or bodily fluids such as blood, urine, semen, lymphatic fluid, cerebrospinal fluid, or amniotic fluid, or other biological samples, such as tissue culture cells, buccal swabs, mouthwashes, stool, tissues slices, biopsy aspiration, and archeological samples such as bone or mummified tissue. Target nucleic acids can be, for example, DNA, RNA, or the DNA product of RNA subjected to reverse transcription. Target samples can be derived from any source including, but not limited to, eukaryotes, plants, animals, vertebrates, fish, mammals, humans, non-humans, bacteria, microbes, viruses, biological sources, serum, plasma, blood, urine, semen, lymphatic fluid, cerebrospinal fluid, amniotic fluid, biopsies, needle aspiration biopsies, cancers, tumors, tissues, cells, cell lysates, crude cell lysates, tissue lysates, tissue culture cells, buccal swabs, mouthwashes, stool, mummified tissue, forensic sources, autopsies, archeological sources, infections, nosocomial infections, production sources, drug preparations, biological molecule productions, protein preparations, lipid preparations, carbohydrate preparations, inanimate objects, air, soil, sap, metal, fossils, excavated materials, and/or other terrestrial or extra-terrestrial materials and sources. The sample may also contain mixtures of material from one source or different sources. For example, nucleic acids of an infecting bacterium or virus can be amplified along with human nucleic acids when nucleic acids from such infected cells or tissues are amplified using the disclosed methods. Types of useful target samples include eukaryotic samples, plant samples, animal samples, vertebrate samples, fish samples, mammalian samples, human samples, non-human samples, bacterial samples, microbial samples, viral samples, biological samples, serum samples, plasma samples, blood samples, urine samples, semen samples, lymphatic fluid samples, cerebrospinal fluid samples, amniotic fluid samples, biopsy samples, needle aspiration biopsy samples, cancer samples, tumor samples, tissue samples, cell samples, cell lysate samples, crude cell lysate samples, tissue lysate samples, tissue culture cell samples, buccal swab samples, mouthwash samples, stool samples, mummified tissue samples, autopsy samples, archeological samples, infection samples, nosocomial infection samples, production samples, drug preparation samples, biological molecule production samples, protein preparation samples, lipid preparation samples, carbohydrate preparation samples, inanimate object samples, air samples, soil samples, sap samples, metal samples, fossil samples, excavated material samples, and/or other terrestrial or extra-terrestrial samples. Types of forensics samples include blood, dried blood, bloodstains, buccal swabs, fingerprints, touch samples (e.g., epithelial cells left on the lip of a drinking glass, the inner rim of a baseball cap, or cigarette butts), laser-dissected cells, chewing gum, gastric contents, saliva, nail scrapings, soil, sexual assault samples including sperm and vaginal epithelial cells, hair, bone, skin, and solid tissue. Types of environmental samples include unfiltered and filtered air and water, soil, swab samples from surfaces, envelopes, and powders.

For example, in some embodiments, the methods described herein can provide amplified nucleic acid samples whose analysis yields data suitable for forensic interpretation, and in particular, data that satisfies forensic interpretation guidelines. Such guidelines include signal strength, inter-loci peak height balance, heterozygous peak height ratio (PHR), incomplete non-template nucleotide addition (iNTA), and stutter (Scientific Working Group on DNA Analysis Methods, Short Tandem Repeat (STR) Interpretation Guidelines. Forensic Science Communications, 2000, 2(3)).

As used herein the term "nucleic acid" is intended to encompass single- and double-stranded DNA and RNA, as well as any and all forms of alternative nucleic acid containing modified bases, sugars, and backbones. The term "nucleic acid" thus will be understood to include, but not be limited to, single- or double-stranded DNA or RNA (and forms thereof that can be partially single-stranded or partially double-stranded), cDNA, aptamers, peptide nucleic acids ("PNA"), 2'-5' DNA (a synthetic material with a shortened backbone that has a base-spacing that matches the A conformation of DNA; 2'-5' DNA will not normally hybridize with DNA in the B form, but it will hybridize readily with RNA), and locked nucleic acids ("LNA"). Nucleic acid analogues include known analogues of natural nucleotides that have similar or improved binding, hybridization of base-pairing properties. "Analogous" forms of purines and pyrimidines are well known in the art, and include, but are not limited to aziridinylcytosine, 4-acetylcytosine, 5-fluorouracil, 5-bromouracil, 5-carboxymethylaminomethyl-2-thiouracil, 5-carboxymethylaminomethyluracil, inosine, $N^6$-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, $N^6$-methyladenine, 7-methylguanine, 5-methylaminomethyluracil, 5-methoxyaminomethyl-2-thiouracil, beta-D-mannosylqueosine, 5-methoxyuracil, 2-methylthio-$N^6$-isopentenyladenine, uracil-5-oxyacetic acid methylester, pseudouracil, queosine, 2-thiocytosine, 5-methyl-2-thiouracil, 2-thiouracil, 4-thiouracil, 5-methyluracil, uracil-5-oxyacetic acid, and 2,6-diaminopurine. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs), methylphosphonate linkages or alternating methylphosphonate and phosphodiester linkages (Strauss-Soukup, 1997, Biochemistry 36:8692-8698), and benzylphosphonate linkages, as discussed in U.S. Pat. No. 6,664,057; see also OLIGONUCLEOTIDES AND ANALOGUES, A PRACTICAL APPROACH, edited by F. Eckstein, IRL Press at Oxford University Press (1991); Antisense Strategies, Annals of the New York Academy of Sciences, Volume 600, Eds. Baserga and Denhardt (NYAS 1992); Milligan, 1993, J. Med. Chem. 36:1923-1937; Antisense Research and Applications (1993, CRC Press). The nucleic acids herein can be extracted from cells or synthetically prepared according to any means known to those skilled in the art; for example, the nucleic acids can be chemically synthesized or transcribed or reverse transcribed from cDNA or mRNA, among other sources.

In certain aspects, described herein are methods for substantially simultaneously amplifying multiple nucleic acid loci in one or more target nucleic acids via rapid polymerase chain reaction (PCR). In some embodiments, such methods comprise (a) contacting in one solution a sample of one more nucleic acid templates obtained from one or more sources with at least six different primer pairs, each pair hybridizing to one of at least six loci in the one or more nucleic acid templates, wherein at least one primer of the primer pair is labeled, and wherein at least six different labels are used; (b) amplifying by polymerase chain reaction (PCR) in one reaction chamber at least six polymorphic loci in the one or more nucleic acids to produce at least six nucleic acid products. A sample can have one or more nucleic acids obtained (isolated or derived) from a single individual or from more than one individual. The one or more nucleic acids can also be obtained from multiple sources, for example, from two or more individuals, or from two or more different tissue samples (e.g., organs, cell types) from the same individual. The reaction chamber can have one sample of one or more nucleic acids, or more than one sample of one or more nucleic acids. For example, the methods described herein can be used to run multiple substantially simultaneous analyses (amplifications) on the same nucleic acid sample or on multiple nucleic acid samples.

Primers for PCR amplification are oligonucleotide sequences that are specifically designed to hybridize to loci of the target DNA. These primers serve as starting points for polymerase extensions. To facilitate analysis of amplified (nucleic acid) fragments, labeled primers can also be used in PCR reactions. Labeled primers are oligonucleotide sequences that are coupled (or conjugated) to a detectable moiety; non-limiting examples thereof include fluorescent dyes, radioactive labels, and identifiable metals, nucleic acid sequences, and proteins. When PCR is carried out with fluorescently labeled primers, amplicons (nucleic acid amplification products) with a fluorescent label are generated. In some embodiments, at least six, at least 7, or at least 8 or more fluorescent dyes are used to in a single amplification reaction (in one reaction chamber). One or more dyes may be used to generate a control sequence such as a sizing standard or an allelic ladder.

Primer sets can be any known to those skilled in the art for the amplification of multiple individual loci within a target nucleic acid, as described above. For example, primers useful in amplification of one or more loci in a human nucleic acid sample are described in U.S. Pat. No. 5,582,989; U.S. Pat. No. 5,843,660; U.S. Pat. No. 6,221,598; U.S. Pat. No. 6,479,235; U.S. Pat. No. 6,531,282; and U.S. Pat. No. 7,008,771; and US Patent Application Publication Nos. 2003/0180724; 2003/0186272; and 2004/0137504, each of which are hereby incorporated by reference.

Further, primers useful in amplification of one or more loci in a viral nucleic acid sample are described in, for example, U.S. Pat. No. 7,312,036; U.S. Pat. No. 6,958,210; U.S. Pat. No. 6,849,407; U.S. Pat. No. 6,790,952, and U.S. Pat. No. 6,472,155, each of which are hereby incorporated by reference.

Examples of primers useful in amplification of one or more loci in a bacterial nucleic acid sample are described in U.S. Pat. No. 7,326,779; U.S. Pat. No. 7,205,111; U.S. Pat. No. 7,074,599; U.S. Pat. No. 7,074,598; U.S. Pat. No. 6,664,080; and U.S. Pat. No. 5,994,066, each of which are hereby incorporated by reference.

Salts and buffers include those familiar to those skilled in the art, including those comprising $MgCl_2$, and Tris-HCl and KCl, respectfully. Buffers may contain additives such as surfactants, dimethyl sulfoxide (DMSO), glycerol, bovine serum albumin (BSA) and polyethylene glycol (PEG), as well as others familiar to those skilled in the art. Nucleotides are generally deoxyribonucleoside triphosphates, such as deoxyadenosine triphosphate (dATP), deoxycytidine triphophate (dCTP), deoxyguanosine triphosphate (dGTP) and deoxythymidine triphosphate (dTTP) are also added to the reaction chamber in adequate amount for amplification of the target nucleic acid.

The solutions can be optionally heated to and held at a first temperature for a first period of time suitable for hot-start activation of the nucleic acid polymerases. Generally, the first period of time is less than about 90 seconds. The first temperature can be about 90-98° C. Polymerases with hot start mechanisms that can be activated in 60 seconds or less include those utilizing antibody mediated hot-start and aptamer mediated hot start mechanisms. Alternatively, hot-start polymerases need not be utilized in the methods described herein.

Subsequently, the temperature of the reaction solutions may be sequentially cycled between a denaturing state, an annealing state, and an extension state for a predetermined number of cycles. In some embodiments, the one or a plurality of reaction solutions are cooled from the denaturing state to the annealing state at a first cooling rate of about 1 to about 150° C./sec, or about 1 to about 100° C./sec; or about 1 to about 80° C./sec; or about 1 to about 60° C./sec; or about 1 to about 40° C./sec; or about 1 to about 30° C./sec; or about 1 to about 20° C./sec; about 4 to about 150° C./sec, or about 4 to about 100° C./sec; or about 4 to about 80° C./sec; or about 4 to about 60° C./sec; or about 4 to about 40° C./sec; or about 4 to about 30° C./sec; or about 4 to about 20° C./sec; or about 10 to about 150° C./sec; or about 10 to about 100° C./sec; or about 10 to about 80° C./sec; or about 10 to about 60° C./sec; of about 10 to about 40° C./sec; or about 10 to about 30° C./sec; or about 10 to about 20° C./sec. The one or a plurality of reaction solutions may be heated from the annealing state to the extension state at a first heating rate of about 1 to about 150° C./sec, or about 1 to about 100° C./sec; or about 1 to about 80° C./sec; or about 1 to about 60° C./sec; or about 1 to about 40° C./sec; about 1 to about 30° C./sec; about 1 to about 20° C./sec; 4 to about 150° C./sec, or about 4 to about 100° C./sec; or about 4 to about 80° C./sec; or about 4 to about 60° C./sec; or about 4 to about 40° C./sec; about 4 to about 30° C./sec; about 4 to about 20° C./sec; or about 10 to about 150° C./sec; or about 10 to about 100° C./sec; or about 10 to about 80° C./sec; or about 10 to about 60° C./sec; of about 10 to about 40° C./sec; or about 10 to about 30° C./sec; or about 10 to about 20° C./sec; and/or the one or a plurality of reaction solutions are heated from the extension state to the denaturing state at a second heating rate of about 1 to about 150° C./sec, or about 1 to about 100° C./sec; or about 1 to about 80° C./sec; or about 1 to about 60° C./sec; or about 1 to about 40° C./sec; about 1 to about 30° C./sec; about 1 to about 20° C./sec; about 4 to about 150° C./sec, or about 4 to about 100° C./sec; or about 4 to about 80° C./sec; or about 4 to about 60° C./sec; or about 4 to about 40° C./sec; about 4 to about 30° C./sec; about 4 to about 20° C./sec; or about 10 to about 150° C./sec; or about 10 to about 100° C./sec; or about 10 to about 80° C./sec; or about 10 to about 60° C./sec; of about 10 to about 40° C./sec; or about 10 to about 30° C./sec; or about 10 to about 20° C./sec. Finally, the reaction solutions are held at a final state to provide one or a plurality of amplified nucleic acid products.

The annealing temperature and time can influence the specificity and efficiency of primer binding to a particular locus within a target nucleic acid and may be important for multiplex PCR reactions. The correct binding of a complete set of primer pairs during the annealing step can allow production of multiplex amplification of a plurality of loci, for example, one or a plurality of full STR profiles with acceptable PHR and inter-locus signal strength balance. For a given primer pair, annealing states can range in some embodiments from about 50° C. to 70° C. and times from less than 1 to greater than 30 seconds. The actual times and temperatures are enzyme, primer, and target dependent.

Extension temperature and time may impact the allele product yield and are understood to be an inherent property of the enzyme being employed. For a given enzyme, extension states can range in some embodiments from about 45° C. to 80° C. and times from about less than 1 to greater than 30 seconds. The actual times and temperatures are enzyme, primer, and target dependent. For continuing a predetermined number of cycles, the reaction solution may be heated from the extension state to the denaturing state at a third rate of about 1 to about 150° C./sec, or about 1 to about 100° C./sec; or about 1 to about 80° C./sec; or about 1 to about 60° C./sec; or about 1 to about 40° C./sec; or about 1 to about 30° C./sec; or about 1 to about 20° C./sec; 4 to about 150° C./sec, or about 4 to about 100° C./sec; or about 4 to about 80° C./sec; or about 4 to about 60° C./sec; or about 4 to about 40° C./sec; or about 4 to about 30° C./sec; or about 4 to about 20° C./sec; or about 10 to about 150° C./sec; or about 10 to about 100° C./sec; or about 10 to about 80° C./sec; or about 10 to about 60° C./sec; of about 10 to about 40° C./sec; or about 10 to about 30° C./sec; or about 10 to about 20° C./sec. In some embodiments, the predetermined number of cycles is chosen to be about 10 to about 50 cycles, although fewer or more cycles may be used as necessary.

For STR reactions, final extension times can be reduced significantly until incomplete NTA begins to increase. For a given enzyme, final extension temperatures can in some embodiments range from about 60 to 75° C. and times from about 0 to 5400 seconds. The actual times and temperatures are enzyme, primer, and target dependent.

In addition to the 3-step thermal cycling approach set forth above, this methods and compositions of the invention are also amenable to 2-step thermal cycling approaches. In this approach in some embodiments, the reaction solutions are sequentially cycled between a denaturing state, and an annealing/extension state for a predetermined number of cycles. This approach may utilize primers designed to anneal at the extension temperature, allowing the annealing and extension steps to share the same temperature. The reduced number of temperature transitions may result in a further reduction in the cycle time.

In some embodiments, multiple amplified nucleic acid products are obtained in about 5 to about 20 minutes. In certain other embodiments, multiple amplified nucleic acid products are obtained in about 5 to 10 minutes, about 1 to 5 minutes, or less than 5 minutes. In some embodiments, each amplified nucleic acid product can be generated starting from less than about 10 ng of a target nucleic acid. In some embodiments, amplified nucleic acid products are generated starting from less than about 5 ng or less than about 2 ng of nucleic acid, or less than about 1 ng of nucleic acid, or less than about 0.5 ng of nucleic acid, or less than about 0.2 ng of nucleic acid, or less than about 0.1 ng of nucleic acid, or less than about 0.05 ng of nucleic acid, or less than about 0.006 ng of nucleic acid.

In other embodiments, such as the identification of biological weapons agents in clinical or environmental samples or the diagnosis of bacterial, viral, or fungal infections in humans, plants, and animals, amplified nucleic acid products can be generated starting from at least one copy of a target nucleic acid. For example, a sample to be analyzed can comprise less than 1000 copies (e.g., 1-1000 copies), less than 400 copies, less than 200 copies, less than 100 copies, less than 50 copies, less than 30 copies, less than 10 copies or 1 copy of a target nucleic acid prior to the multiplex amplification reaction.

In any of the preceding methods, the thermal cycling can be performed for a predetermined number of cycles to achieve sufficient amplification of the loci in the target nucleic acid as can be readily determined by one skilled in the art. For example, the predetermined number of cycles may range between about 10 and about 50 cycles, and in some embodiments between about 20 and 50 cycles. Further, in at least some embodiments of the preceding methods, at least 2 loci of one or a plurality of nucleic acids can be substantially simultaneously amplified. Depending on the desired application, greater than four, 5 to 10, 10 to 20, 20 to 30 or about 10 to 250 loci may be simultaneously amplified. For example, for amplification of STR loci, 10-20 loci can be amplified.

Many commercially available polymerases can be adapted for use in fast PCR applications using the methods described here. In some embodiments, the nucleic acid polymerase has an extension rate of at least 100 bases/sec. A large number of polymerases available for PCR amplification including *Thermus aquaticus* (Taq), *Pyrccoccus furiosus* (Pfu), *Pyrococcus woesei* (Pwo), *Thermas flavus* (Tfl), *Themus thermophilus* (Tth), *Thermus litoris* (Tli) and *Thermotoga maritime* (Tma). These enzymes, modified version of these enzymes, and combination of enzymes, are commercially available from vendors including Roche®, Invitrogen®, Qiagen®, Strategene®), and Applied Biosystems®. Representative enzymes include PHUSION® (New England Biolabs, Ipswich, Mass.), Hot MasterTaq™ (Eppendorf), PHUSION® Mpx (Finnzymes), PyroStart™ (Fermentas), KOD™ (EMD Biosciences), Z-Taq™ (TAKARA), and CS3AC/LA (KlenTaq, University City, Mo.). A widely used enzyme for PCR amplification for STR typing is the Taq DNA polymerase.

A large number of dyes (greater than 100) are available for application in fluorescent excitation and detection. The broad range of available dyes allows selection of dye sets that have emission wavelengths that are spread across the detection range and thus have minimal overlap between emission maxima. Dyes are available that are chemically modified for covalent attachment to oligonucleotides and primers include those from the fluorescein, rhodamine, AlexaFluor, Bodipy, Coumarin, Cascade Dyes, and Cyanine dye families. Fluorescent dyes can be commercially obtained from a number of commercial suppliers including Invitrogen/Molecular Probes (Carlsbad, Calif.), Anaspec (Freemont, Calif.), GE Healthcare (Piscataway, N.J.), and Pierce/Thermo Fisher (Waltham, Mass.), Such dyes can be obtained as chemically modified derivatives (e.g. amidites, N-hydroxy succinimide esters, succinimidyl esters, isothiocyanates) for attachment to the oligonucleotide. A number of companies offer synthesis of such fluorescently labeled oligonucleotides and chemically modified oligonucleotides (e.g. Invitrogen, Carlsbad, Calif., Operon Biotechnologies, Huntsville, Ala.; IDT, Coralville, Iowa; Gene Link, Hawthorne, N.Y.; AnaSpec Inc., Freemont, Calif.; BioSynthesis, Lewisville, Tex.,).

Chemically activated (modified) fluorescent dyes can be attached to the oligonucleotide probe/primer either during synthesis of oligonucleotides (amidite chemistry, PhAm chemistry) or post-synthetically (dyes modified with NHS ester, succinimidyl ester or isothiocyanate). While the first method (incorporation of phosphoamidite linked dye groups into the growing oligo chain) is more convenient, post-synthetic coupling of activated dyes (e.g., as NHS esters) to oligonucleotides that contain 5' amino linker groups is well established. The amino group thereby reacts with the activated dye forming a covalent bond that is stable during PCR, hybridization, and other manipulations. Examples of phosphoamidite linked dyes are FAM™, JOE™, and some Cy dyes.

Fluorescent dyes have peak excitation wavelengths that are typically 20 to 50 nm blue-shifted from their peak emission wavelength (Stokes shift). As a result, use of dyes over a wide range of emission wavelengths may require the use of multiple excitation sources, with excitation wavelengths to achieve efficient excitation of the dyes over the emission wavelength range. For example, FAM is excited very efficiently at 488 nm using a conventional blue Argon laser (excitation maximum at 488 nm) while Cy5.5 is very inefficiently excited by the same laser (Cy5.5 excitation maximum is at 673 nm). One method to excite such red shifted dyes efficiently is by fluorescent energy transfer, enabling efficient single laser excitation of for example FAM and Cy5.5. This is achieved by attaching a dye that is efficiently excited by the chosen light source (the absorber) in close proximity to the dye that is not efficiently excited by the same light source but emits at red shifted wavelengths (the emitter). Placement of the absorber in close proximity with an emitter allows the absorbed energy to be transferred from the absorber to the emitter, allowing for more efficient excitation of the long wavelength dyes. The optimal spatial distance of the absorber and the emitter is called the Förster distance and is experimentally determined by placing suitable spacer moieties between absorber and emitter dye. Such moieties may be simple carbon spacers (e.g. C3, C6, C18 linkers), oligonucleotide spacers, or modified nucleotides to that the two dyes can be chemically linked to maintain the optimal distance. Optimal spacing of the absorber and emitter dyes will result in excitation of the absorber, transfer of the energy to the emitter and fluorescent emission of the emitter dye only. If dyes are spaced too far apart, the fluorescent energy transfer is inefficient and the absorber may emit at its fluorescent maximum wavelength. In contrast, if absorber and emitter are too closely spaced, fluorescent quenching (no fluorescence/emission) may be observed.

Finally, dyes may alter the electrophoretic mobility of amplified fragments. In general, this is not an important issue unless the altered mobility causes an overlap with amplicons from a different locus. In the relatively uncommon events in which such altered mobility does cause overlap, primer design to eliminate the overlap is required (e.g. by the addition of bases to the 5' terminus of the labeled primer of the locus generating larger amplicons of the overlapping loci).

Several parameters known to those of skill in the art may be used to optimize the PCR amplification methods described herein. The criteria for optimization of the protocols include the generation of full profiles, signal strength, dynamic range, inter-locus signal strength balance, PHR, incomplete NTA, stutter, and total cycle time (Hill, C R, Butler, J M, Vallone, P M. A 26plex Autosomal STR Assay to Aid Human Identity Testing. J Forensic Sci 54:1008-1015. 2009. Brownstein, M J, Carpten, J D, Smith, J R. Modulation of Non-Template Nucleotide Addition by Taq DNA Polymerase: Primer Modifications that Facilitate Genotyping. BioTechniques 30:1004-1010. 1996. SWGDAM Interpretation Guidelines for Autosomal STR Typing by Forensic DNA Testing Laboratories. 2010. http://www.fbi.gov/about-us/lab/codis/swgdam-interpretation-guidelines).

In some embodiments, the total cycling time for at least 10, 20, or 30 multiplex PCR cycles can range from about 1 minute to about 90 minutes. In some embodiments, total cycling time for at least 10, 20, or 30 multiplex PCR cycles ranges from about 1 minute to about 90 minutes; or from about 1 minute to about 85 minutes; or from about 1 minute to about 80 minutes; or from about 1 minute to about 75 minutes; or from about 1 minute to about 70 minutes; or from about 1 minute to about 65 minutes; or from about 1 minute to about 60 minutes; or from about 1 minute to about 55 minutes; or from about 1 minute to about 50 minutes; or from about 1 minute to about 45 minutes; or from about 1 minute to about 40 minutes; or from about 1 minute to about 35 minutes; or from about 1 minute to about 30 minutes; or from about 1 minute to about 25 minutes; or from about 1 minute to about 20 minutes; or from about 1 minute to about 15 minutes; or from about 1 minute to about 10 minutes or from about 1 minute to about 5 minutes. In other embodiments, the total cycling time for at least 10, 20, or 30 multiplex PCR cycles is less than about 90 minutes. In yet other embodiments, the total cycling time for at least 10, 20, or 30 multiplex PCR cycles is less than about 89, 85, 80, 75, 70, 65, 60, 55, 50, 45, 40, 35, 30, 25, 20, 15, 10, 5, 4, 3, 2, or 1 minute.

It is contemplated that the methods described herein can be carried out using conventional PCR thermal cyclers such as the GeneAmp® PCR System 9700 (Applied Biosystems, Foster City, Calif.). Each reaction chamber may be contained within a thin-walled reaction tubes. Thin-walled reaction tubes preferably have a wall thickness of less than about 200 µm. Preferably, thin-walled reaction tubes preferably have a wall thickness of less than about 100 µm.

It is also contemplated that the PCR amplification methods herein are performed using microfluidic biochips, for example, those described in application Ser. No. 12/080,746 entitled "Methods for Rapid Multiplexed Amplification of Target Nucleic Acids," and application. Ser. No. 13/044,485 entitled "Unitary Biochips," both of which have been incorporated by reference herein. Each reaction chamber may be contained within a biochip (e.g., microfluidic biochip).

Biochips may be used in some embodiments to perform methods of the invention. Certain biochip designs may achieve the fundamental goal of the field of microfluidics: the integration of some or in some embodiments all steps in a complex process, from the insertion of a sample to the generation of a result, performed in a single instrument without operator intervention. The biochips in some embodiments can be fully integrated and capable of performing complex sample in to results out analyses including cell lysis, DNA purification, multiplex amplification, and electrophoretic separation and detection to generate short tandem repeat (STR) profiles from forensic samples; cell lysis, DNA purification, multiplexed amplification, Sanger sequencing, ultrafiltration, and electrophoretic separation and detection to generate DNA sequence from clinical samples; nucleic acid purification, reverse transcription, multiplexed amplification, Sanger sequencing, ultrafiltration, and electrophoretic separation and detection to generate DNA sequence from biothreat samples, and nucleic acid purification, library construction, and single molecule sequencing to generate genomic DNA sequences from human, bacterial, and viral clinical and research samples.

In some embodiments, sample manipulations are performed in biochips, including combinations of nucleic acid extraction; cell lysis; cell separation; differential cell lysis; differential filtration; total nucleic acid purification; DNA purification; RNA purification; mRNA purification; protein purification; pre-nucleic acid amplification cleanup; nucleic acid amplification (e.g. both singleplex and multiplex endpoint PCR, Real-time PCR, reverse transcription PCR, asymmetric PCR, nested PCR, LATE PCR, touchdown PCR, digital PCR, rolling circle amplification, strand displacement amplification, and multiple displacement amplification); Y-STR amplification; mini-STR amplification; single nucleotide polymorphism analysis; VNTR analysis; RFLP analysis; post-nucleic acid amplification cleanup; pre-nucleic acid sequencing cleanup; nucleic acid sequencing (e.g. Sanger sequencing, pyrosequencing, and single molecule sequencing); post-nucleic acid sequencing cleanup; reverse transcription; pre-reverse transcription cleanup; post-reverse transcription cleanup; nucleic acid ligation; SNP analysis; nucleic acid hybridization; electrophoretic separation and detection; immunoassays; binding assays; protein assays; enzymatic assays; mass spectroscopy; and nucleic acid and protein quantification.

In some embodiments, biochips allow nucleic acids and other biological components from unprocessed biological samples to be purified, manipulated, and analyzed. Unprocessed biological samples are those that are collected by an individual and then inserted into the sample receiving chamber of the biochip with no intermediate processing steps (although the sample collection device may be labeled and/or stored prior to processing). The operator need only collect or otherwise obtain the sample, insert the sample into the apparatus, insert the apparatus into the instrument (not necessary if the apparatus was previously placed in the instrument), and press a start button. No processing, manipulation, or modification of the sample is required prior to insertion in the apparatus—the operator does not have to cut a swab, open a blood tube, collect a tissues or biologic fluid, transfer a sample to another holder, or expose the sample to a reagent or a condition (e.g. heat, cold, vibration). Accordingly, the operator need not have extensive training in the biological sciences or laboratory techniques. Optionally, biochips can accept processed biological samples (e.g. a cell lysate for subsequent purification), but such applications may require an operator with technical training.

In practice, biological samples are collected using a myriad of collection devices, all of which can be used with the methods described herein. The collection devices will generally be commercially available but can also be specifically designed and manufactured for a given application. For clinical samples, a variety of commercial swab types are available including nasal, nasopharyngeal, buccal, oral fluid, stool, tonsil, vaginal, cervical, and wound swabs. The dimensions and materials of the sample collection devices vary, and the devices may contain specialized handles, caps, scores to facilitate and direct breakage, and collection matrices. Blood samples are collected in a wide variety of commercially available tubes of varying volumes, some of which contain additives (including anticoagulants such as heparin, citrate, and EDTA), a vacuum to facilitate sample entry, a stopper to facilitate needle insertion, and coverings to protect the operator from exposure to the sample. Tissue and bodily fluids (e.g. sputum, purulent material, aspirates) are also collected in tubes, generally distinct from blood tubes. These clinical sample collection devices are generally sent to sophisticated hospital or commercial clinical laboratories for testing (although certain testing such as the evaluation of throat/tonsillar swabs for rapid streptococcal tests can be performed at the point of care). Environmental samples may be present as filters or filter cartridges (e.g. from air breathers, aerosols or water filtration devices), swabs, powders, or fluids.

A common collection technique for forensic evidence is performed using a swab. Swabs are commercially available from Bode (Lorton, Va.), Puritan (Guilford, Me.), Fitzco (Spring Park, Minn.), Boca (Coral Springs, Fla.), Copan (Murrieta, Calif.) and Starplex (Etobicoke, ON, Canada). Swabbing can also be performed using gauze-like materials, disposable brushes, or commercially available biological sampling kits. Forensic samples may contain blood, semen, epithelial cells, urine, saliva, stool, various tissues, and bone. Biological evidence from an individual that is present in person is often collected using buccal swabs. A widely used commercial buccal swab is the SecurSwab (The Bode Technology Group, Lorton, Va.). Buccal samples are collected by instructing the subject or operator to place the swab into the mouth on the inner cheek surface and to move the swab up and down one or more times.

In some embodiments, biochips are used in the methods described herein to perform complex processes on multiple samples in parallel. In some embodiments, multiple samples are processed using the identical set of manipulations or each sample (or subset of samples) to be processed using a tailored set of manipulations. In some embodiments, several independent analyses are performed on a given sample. For example, a forensic sample can analyzed by isolating DNA and then performing STR analysis, SNP analysis, and mitochondrial sequencing on the purified material. Similarly, a clinical sample can be analyzed by purifying nucleic acids and proteins and performing PCR, reverse-transcription PCR, DNA sequencing, and immunoassays, allowing (for example) a given sample to be interrogated for a large number of pathogens and cellular processes simultaneously on a single biochip.

A series of software and firmware may be provided for biochip operation and data analysis. The instrument hardware is controlled by software and firmware that dictate component function and perform instrument self-testing. An automated script controls all interactions of the instrument with the biochip, including the application of all scripted process steps. Analytical software performs both the processing of raw data (e.g. color correction of an electropherogram) and analysis if the results of the assay (e.g. fragment sizing, STR allele calling, DNA sequence analysis). The instrument may contain a graphical user interface that allows the user to initiate the process and inform the user of process status. Finally, the system may store relevant analytical comparators (e.g. STR profiles from individuals of interest or DNA sequence of pathogens), or the system may port out results for external database matching and further analyses.

The Examples that follow are illustrative of specific embodiments of the invention, and various uses thereof. They set forth for explanatory purposes only, and are not to be taken as limiting the invention.

EXAMPLES

Example 1

Fluorescent Detection of Simultaneous Multiplex Amplification of STR Loci D3S1358, D19S433, D2S1338, D22S1045, Penta B, TH01, D18S51, D1S1656, D10S1248, D2S441, Penta C, D16S539, vWFA31, D21S11, D12S391, Penta D, D5S818, D13S317, D7S820, TPOX, CSF1PO, Penta E, D8S1179, FGA, and SE33 and the Amelogenin Locus in a 5-color Amplification and Separation and Detection System.

The first step in this multiplex design required locus selection. Several criteria were used to choose from the hundreds of thousands of available polymorphic loci but a primary discriminating factor was the degree of polymorphism of each locus. Loci with more alleles that display more similar frequencies display higher heterozygosity $$\left( H = 1 - \sum_{i}^{alleles} p_i^2 \right)$$

(Weir, B S. Genetic Data Analysis II, Chapter 4, p. 141. Sinaeur Associates Inc, Publishers 1996) and higher polymorphic information content $$\left( PIC = 1 - \sum_{i=1}^{n} p_i^2 - \sum_{i=1}^{n} \sum_{j=i+1}^{n} 2 p_i^2 p_j^2, \right.$$

Botstein, D, White, R L, Skolnick, M, Davis, R W. Construction of a genetic Linkage Map in Manu Using Restriction Fragment Length Polymorphisms, Am J Hum Genet 32:314-331, 1980). This trait offers significant advantage in matching DNA sample sources to one another. High polymorphic information content of individual loci is particularly important in paternity and kinship analyses that include related individuals as the genome can accommodate only a finite number of unlinked loci preferred for these analyses. Hence, in general, highly polymorphic loci with many alleles were selected unless other factors impacted selection.

Another important factor was inclusion of loci utilized for law enforcement purposes in the United States and around the world. Not all countries use the same set of STR loci for identification. The fact that different nations use different sets of loci reduces the utility of searching one country's database with a profile collected in another. By developing a primer set that includes all the United Stated standard STR loci as well as all loci routinely utilized in jurisdictions around the world, it will be much more informative to search databases and identify individuals. This approach offers an additional advantage for use in immigration testing and in testing for samples related to international crime as the multiplex contains suitable loci for searching databases from around the world.

A multiplex containing 25 STR loci plus the amelogenin locus was designed as indicated in Table 3. This multiplex includes all 13 STR loci accepted in the United States CODIS database (Table 3, United States CODIS column) and those recommended for standardization in European countries [Schneider, P M. Expansion of the European Standard Set of DNA Database Loci—The Current Situation. Profiles in DNA, Promega Corporation, March 2009], by the European DNA Profiling (EDNAP) Group and the European Network of Forensic Science Institutes (ENFSI) (Table 3, Europe EDNAP/ENFSI column). Three different loci are included in the Austrian national database set, and one different locus, SE33, for the German database. Finally, pentanucleotide loci valued for the increased separation observed between amplified alleles are also included.

Table 3. Locus Selection

TABLE 3

Locus Selection

| | CODIS Core 13 STR Loci | European EDNAP/ENFSI Standard STR Set | Austrian German | 26-locus Example of the Invention |
|---|---|---|---|---|
| 1 | | amelogenin | | amelogenin |
| 2 | CSF1PO | | | CSF1PO |
| 3 | | D1S1656 | | D1S1656 |
| 4 | | D2S441 | | D2S441 |
| 5 | | | D2S1338 (Austrian) | D2S1338 |
| 6 | D3S1358 | D3S1358 | | D3S1358 |
| 7 | D5S818 | | | D5S818 |
| 8 | D7S820 | | | D7S820 |
| 9 | D8S1179 | D8S1179 | | D8S1179 |
| 10 | | D10S1248 | | D10S1248 |
| 11 | | D12S391 | | D12S391 |
| 12 | D13S317 | | | D13S317 |
| 13 | D16S539 | | D16S539 (Austrian) | D16S539 |
| 14 | D18S51 | D18S51 | | D18S51 |
| 15 | | | D19S433 (Austrian) | D19S433 |
| 16 | D21S11 | D21S11 | | D21S11 |
| 17 | | D22S1045 | | D22S1045 (not required) |
| 18 | FGA | FGA | | FGA |
| 19 | | | SE33 (German) | SE33 (not required) |
| 20 | TH01 | TH01 | | TH01 |
| 21 | TPOX | | | TPOX (not required) |
| 22 | vWA | vWA | | vWA |
| 23 | | | | Penta B |
| 24 | | | | Penta C |
| 25 | | | | Penta D |
| 26 | | | | Penta E |

The placement of STR loci within a multiplex is based on several considerations, including the range of fragments that can detected in the separation system, the resolution of the separation system (which may vary based on the molecular weight of the two fragments to be discriminated), and, in the case of electrophoretic separation, the number of fluorescent dyes that can be detected during separation. The 25 STR/amelogenin multiplex places four and five base repeat loci with relatively few and rare microvariant alleles (i.e., alleles that do not differ from the others by an integral number of repeat lengths) in the larger amplicon positions. This approach offers the advantage of optimizing analysis of alleles in the higher molecular weight range (for a given separation platform and a given separation time) by placing these alleles in a region that typically has the lowest resolution. The placement of additional four and five base repeat loci with relatively few and rare microvariant alleles in the high molecular weight range, while placing the highly polymorphic locus containing three base repeats (i.e., D22S1045) and loci displaying more frequent microvariant loci at the lower molecular weight range is an important aspect of this multiplex design. The same design trait permits more rapid separation of alleles across the full spectrum of included loci as alleles with 5-base separation in the high molecular weight range separate more readily than the more commonly employed four or three bases STR repeats. This approach permitted improved use of the high molecular weight regions of the multiplex design, permitting the inclusion of more loci with highly polymorphic characteristics labeled with each dye, and ultimately permitted inclusion of more of these loci in the multiplex. The 25 STR loci and the amelogenin locus were labeled with a total of 4 colors (a fifth color was used to label the size marker) and placed across a total molecular weight range from 74 bases to 485 bases. We also positioned the least commonly used loci in the positions of larger amplicon locations to limit information loss in the event that degraded samples eliminated some high molecular weight information.

FIG. 1 illustrates the design permitting co-amplification of 26 loci in a single reaction. The first panel indicates loci labeled in FAM including those for the loci D3S1358, D19S433, D2S1338, D22S1045, Penta B, the second panel displays loci labeled in JOE including those for the loci TH01, D18S51, D1S1656, D10S1248, D2S441, Penta C, the third panel displays loci labeled in carboxy-tetramethyl-rhodamine (TMR) including those for the loci D16S539, vWFA31, D21S11, D12S391, amelogenin, Penta D, the fourth and fifth panels display loci labeled with 5,6-carboxyrhodamine 6G (CXR) for the loci D5S818, D13S317, D7S820, TPOX, CSF1PO, Penta E, D8S1179, FGA, and SE33. The sixth panel displays CC5-labeled fragments that constitute the size marker included for analysis.

Construction of multiplex STR sets may require elimination of artifacts generated by unplanned primer interactions in the mix. For example, the labeled primer of one locus may work in concert with the unlabeled primer of another locus to amplify an unintended sequence during the polymerase chain reaction. This can occur with the genomic target DNA, but is made more likely as the concentrations of the designed amplicons increase during the reaction; this increase provides a higher concentration of template for an inadvertent amplification event to occur (generating the artifactual product). Once created, such artifacts provide perfect matches with the offending pair of primers and amplify efficiently in subsequent rounds of amplification.

To resolve such artifacts, it is helpful to identify which two primers in the multiplex generate the specific artifact(s) in question. This is achieved by systematically eliminating individual primers or groups of primers from the mix until two specific primers are identified whose presence and absence correspond with presence and absence of the artifact(s), respectively. Once the causal primers are identified, the artifacts can be eliminated in a variety of ways. These include (1) using less of one of the primer pairs that contains an offending primer, (2) changing the sequence of one or both offending primers either by addition of bases to the 3' terminus or by complete redesign to a new binding site, (3) changing the labeled primer to be unlabeled and unlabeled primer to be labeled in the primer pair (thus making the artifact(s) undetectable), or (4) modifying the ratio of labeled to unlabeled primer in one or both pairs to diminish generation of the unintended product. Empirical analysis is used to determine the most effective means for achieving artifact reduction with each artifact or set of artifacts.

Locus-to-locus balance is also an important attribute for creation of forensically useful multiplex sets. In this regard, initial primer design includes design of primers that are similar to one another in their respective melting temperatures. The annealing temperature utilized in the amplification process is set lower than this melting temperature to ensure all primer targets are predominantly in the duplex state with complimentary primers rather than in the denatured state. Even so, the relative efficiency of amplification per cycle may differ from one locus to another generating a final multiplex amplification product with greater representation of some loci than others. One way to overcome this imbalance is to increase the concentration of some primers while lowering the concentration of others to compensate for some of the other factors affecting the amplification process. There are limitations to this approach as it is never possible to improve the amplification efficiency to more than a 2-fold increase per round of amplification.

The primer sequences for each of the 26 STR loci were combined into a single solution that included the primer sequences listed in Table 4.

TABLE 4

| Example 1 Locus | Sequence (5' to 3') |
|---|---|
| AMEL | CCCTGGGCTCTGTAAAGAA (SEQ ID NO. 1) |
| AMEL | ATCAGAGCTTAAACTGGGAAGCTG (SEQ ID NO. 2) |
| CSF1PO | CCGGAGGTAAAGGTGTCTTAAAGT (SEQ ID NO. 3) |
| CSF1PO | ATTTCCTGTGTCAGACCCTGTT (SEQ ID NO. 4) |
| D1S1656 | GCGCCTGGTCTTTGTTTAT (SEQ ID NO. 5) |
| D1S1656 | AGAAAATCCCCATATAAGTTCAAGC (SEQ ID NO. 6) |
| D2S1338 | CAAAACCCTGAAAATGGCAATT (SEQ ID NO. 7) |
| D2S1338 | AGTGTTCATGCCTACATCCC (SEQ ID NO. 8) |
| D2S441 | CTTCCTCCAGGGTATTAATGGG (SEQ ID NO. 9) |
| D2S441 | ACATCACAAAAATCTTCACTCTCC (SEQ ID NO. 10) |
| D3S1358 | CCCCACTGCAGTCCAATC (SEQ ID NO. 11) |
| D3S1358 | AATCAACAGAGGCTTGCATG (SEQ ID NO. 12) |
| D5S818 | GGTGATTTTCCTCTTTGGTATCC (SEQ ID NO. 13) |
| D5S818 | AGTTTACAACATTTGTATCTTTATCTGTATC (SEQ ID NO. 14) |
| D7S820 | ATGTTGGTCAGGCTGACTATG (SEQ ID NO. 15) |
| D7S820 | GATTCCACATTTATCCTCATTGAC (SEQ ID NO. 16) |
| D8S1179 | GTATTTCATGTGTACATTCGTATCTATC (SEQ ID NO. 17) |
| D8S1179 | GCCTTAATTTATTTACCTATCCTGTAG (SEQ ID NO. 18) |
| D10S1248 | AAAGCAAACCTGAGCATTAGC (SEQ ID NO. 19) |
| D10S1248 | GTGAGAAACCATACTTTTTCCCT (SEQ ID NO. 20) |
| D12S391 | CTGGTGAAGGAAGAAAAGAGAAT (SEQ ID NO. 21) |
| D12S391 | TTGGCTTTTAGACCTGGACTGA (SEQ ID NO. 22) |

TABLE 4-continued

| Example 1 Locus | Sequence (5' to 3') |
|---|---|
| D13S317 | ATTACAGAAGTCTGGGATGTGGAGGA (SEQ ID NO. 23) |
| D13S317 | GGCAGCCCAAAAAGACAGA (SEQ ID NO. 24) |
| D16S539 | TCAATACAGACAGACAGACAGGTGGAT (SEQ ID NO. 25) |
| D16S539 | GTTTGTGTGTGCATCTGTAAGCATGTATC (SEQ ID NO. 26) |
| D18S51 | CACTTCACTCTGAGTGACAAAT (SEQ ID NO. 27) |
| D18S51 | TCTGGTGTGTGGAGATGTCTTACAATA (SEQ ID NO. 28) |
| D19S433 | GCAAAAAGCTATAATTGTACCACT (SEQ ID NO. 29) |
| D19S433 | AGTTCTTTAGCAGTGATTTCTGATATT (SEQ ID NO. 30) |
| D21S11 | ATATGTGAGTCAATTCCCCAAG (SEQ ID NO. 31) |
| D21S11 | TGTATTAGTCAATGTTCTCCAGAGAC (SEQ ID NO. 32) |
| D22S1045 | ATCGTTGGAATTCCCCAAACTG (SEQ ID NO. 33) |
| D22S1045 | GTGACCTCAGGCAAGTCCCTA (SEQ ID NO. 34) |
| FGA | CCATAGGTTTTGAACTCACAGATTAA (SEQ ID NO. 35) |
| FGA | GCCAGCAAAAAAGAAAGGAAGA (SEQ ID NO. 36) |
| Penta B | CTTGAAGCTGGGAGACGGAAAGT (SEQ ID NO. 37) |
| Penta B | AGCTCTCTTACTTTGGGTGGGC (SEQ ID NO. 38) |
| Penta C | CTTGCAGGAGACAGGGTTTATA (SEQ ID NO. 39) |
| Penta C | CGCCACTGCTACAAGAGAG (SEQ ID NO. 40) |
| Penta D | GTGAGGCTGAAGTAGGATCAC (SEQ ID NO. 41) |
| Penta D | GACACAAGTCCTTTTTTAGATATGTG (SEQ ID NO. 42) |
| Penta E | GGGCGACTGAGCAAGACTCA (SEQ ID NO. 43) |
| Penta E | GACATTTCTTATTTTCTCATATTGGTGG (SEQ ID NO. 44) |
| SE33 | TCTGTAATTCCAGCTCCTAGG (SEQ ID NO. 45) |
| SE33 | AGGTTTATATATATTTCTACAACATCTCC (SEQ ID NO. 46) |
| TH01 | GGCCTGTTCCTCCCTTATTTCC (SEQ ID NO. 47) |
| TH01 | GAGTGCAGGTCACAGGGAAC (SEQ ID NO. 48) |
| TPOX | GCACAGAACAGGCACTTAGG (SEQ ID NO. 49) |
| TPOX | CCCCAACGCTCAAACGTGAGGTTG (SEQ ID NO. 50) |
| vWA | TCCAAGTTGACTTGGCTGAG (SEQ ID NO. 51) |
| vWA | CAGATGATAAATACATAGGATGGATG (SEQ ID NO. 52) |

Figure 2A:
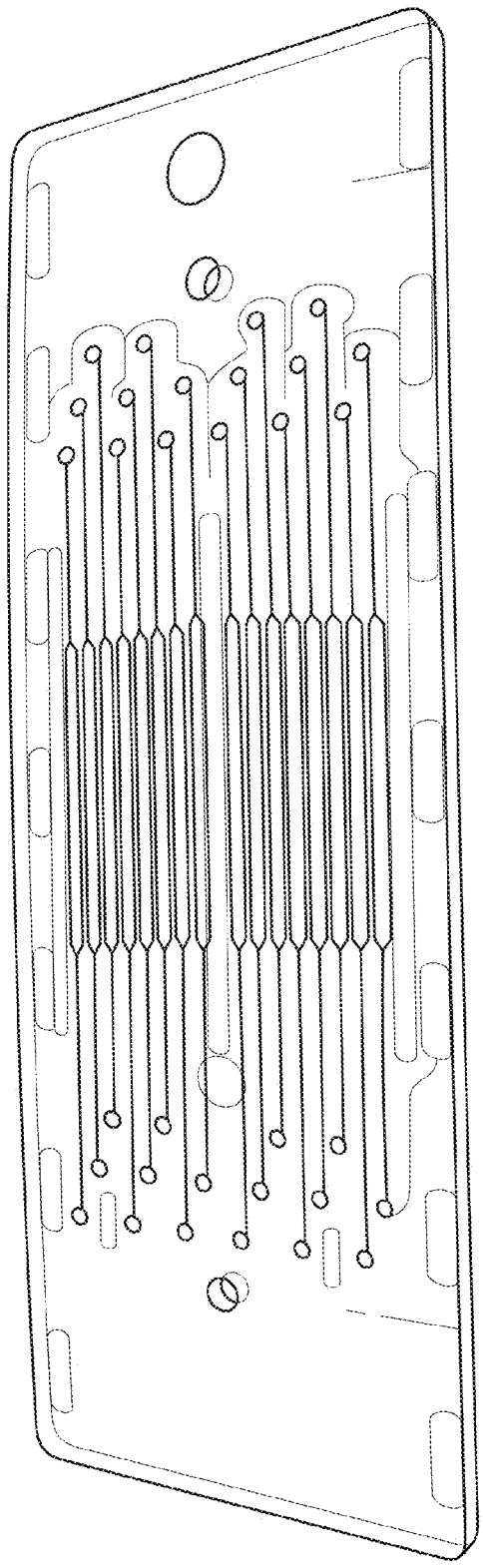
FIG. 2A is a photograph of a microfluidic biochip that performs PCR.
Figure 2B:
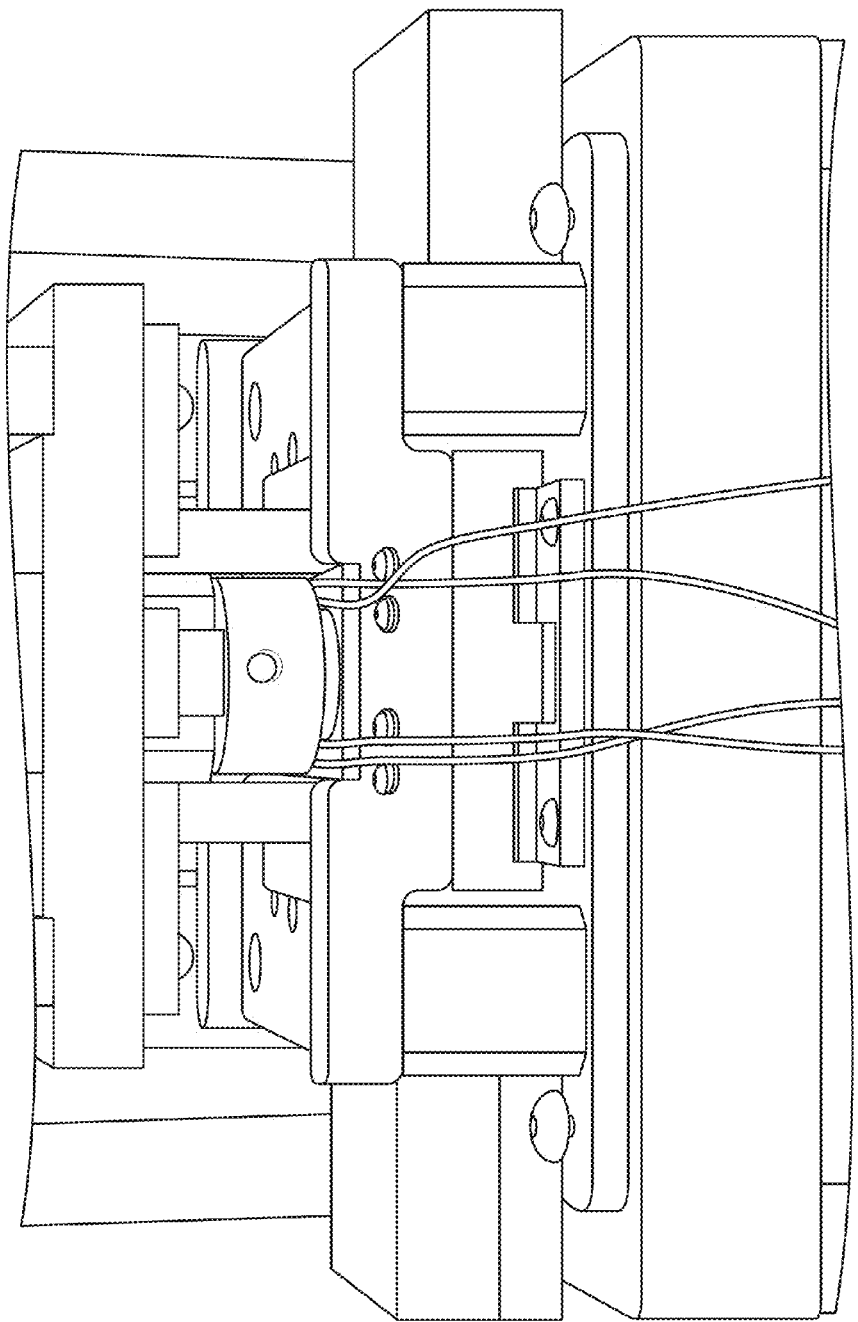
FIG. 2B is a photograph of a rapid thermal cycler that accepts the biochip of FIG. 2A.

Using this 26-plex 25-STR solution, a human genomic DNA template (strain 9947) was amplified simultaneously at the individual loci D3S1358, D19S433, D2S1338, D22S1045, Penta B, TH01, D18S51, D1S1656, D10S1248, D2S441, Penta C, D16S539, vWFA31, D21S11, D12S391, amelogenin, Penta D, D5S818, D13S317, D7S820, TPOX, CSF1PO, Penta E, D8S1179, FGA, and SE33 in a single reaction vessel. The PCR amplification was performed in 7 µl reactions in a microfluidic biochip. The PCR biochip (FIG. 2A) was injection molded in a slide format and successfully tested for rapid multiplexed PCR using the rapid thermal cycler of FIG. 2B. This biochip is 25 mm×75 mm×1.1 mm thick. The system allows multiplexed amplification on STR fragments from a single genome equivalent of human DNA (6 pg of DNA, essentially a single-copy limit of detection). Reactions were performed essentially as described in Giese, H., et al. (2009). "Fast multiplexed polymerase chain reaction for conventional and microfluidic short tandem repeat analysis." *J Forensic Sci* 54(6): 1287-96. A thirty-one cycle protocol was applied to cycle the reaction within the thermal cycling chambers to generate labeled amplicons. The cycling conditions were as follows: Hotstart 93° C.×20 seconds followed by 31 cycles of (93° C.×4 seconds, 56° C.×15 seconds, and 70° C.×7 seconds) followed by a final extension of 70° C.×90 seconds. See also, application Ser. No. 12/080,746 entitled "Methods for Rapid Multiplexed Amplification of Target Nucleic Acids," and application Ser. No. 13/044,485 entitled "Unitary Biochips," both of which have been incorporated by reference herein. Amplified products were separated and detected using NetBio's Genebench-FX. as described in Example 6 below.

Figure 3:
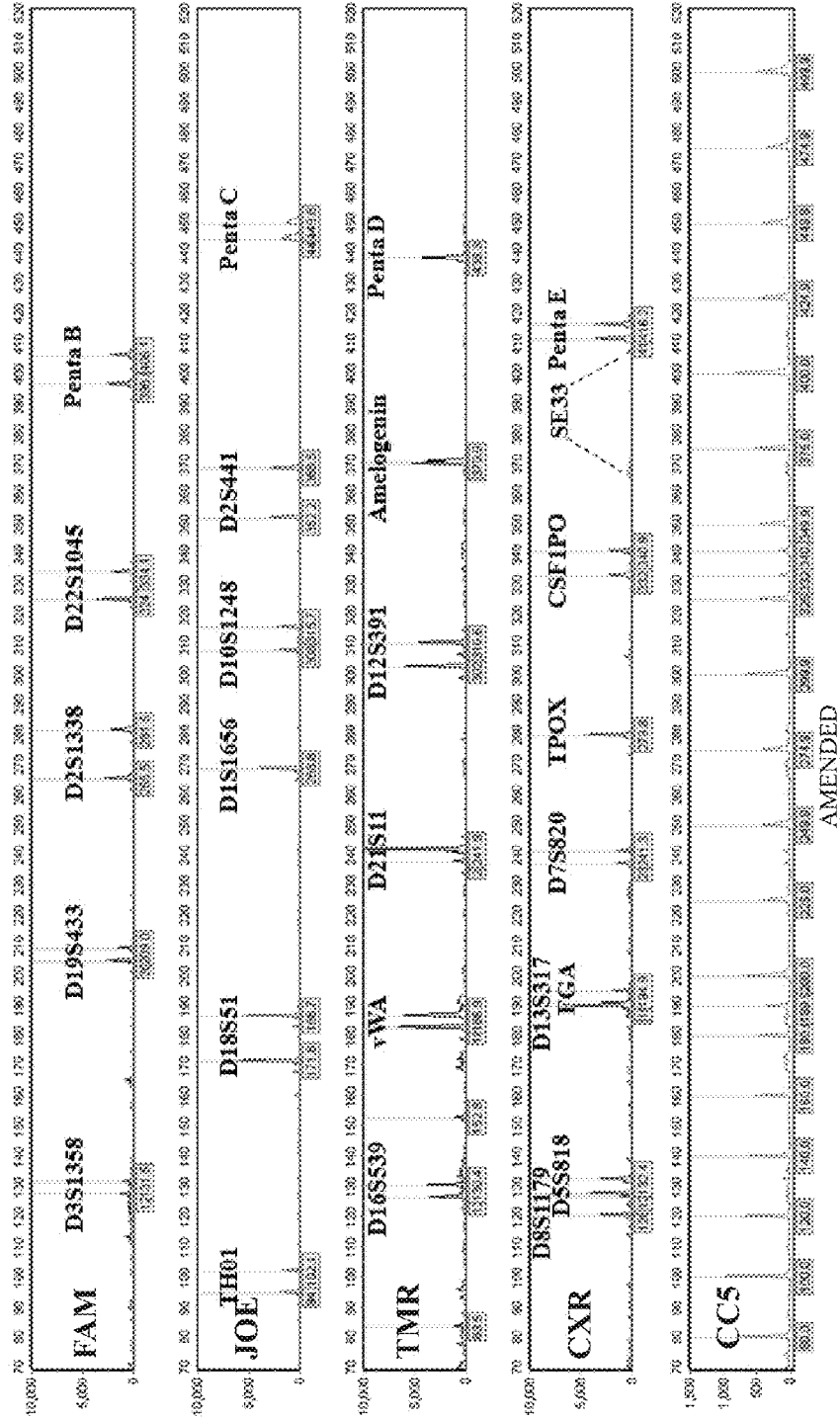
FIG. 3 is a color corrected scan of amplified products for each locus on a 26-locus, 25 STR formal locus multiplex reaction.

FIG. 3 shows a color-corrected scan of the amplified products for each locus of the resulting 26-plex reaction. The 26-locus primer set was used to amplify fragments for each locus separated and detected with the NetBio GeneBench FX™ instrument. The first panel displays peaks labeled in FAM including those for the loci D3S1358, D19S433, D2S1338, D22S1045, Penta B, the second panel displays peaks labeled in JOE including those for the loci TH01, D18S51, D1S1656, D10S1248, D2S441, Penta C, the third panel displays peaks labeled in carboxy-tetramethylrhodamine (TMR) including those for the loci D16S539, vWFA31, D21S11, D12S391, amelogenin, Penta D, the fourth and fifth panels display peaks labeled with 5,6-carboxyrhodamine 6G (CXR) for the loci D5S818, D13S317, D7S820, TPOX, CSF1PO, Penta E, D8S1179, FGA, and SE33. The sixth panel displays CC5-labeled fragments that constitute the size markers.

Example 1 demonstrated that effective co-amplification was achieved with 25 distinct STR loci plus the amelogenin locus, and these products were separated and detected. This showed that the primer sequences employed were sufficiently well-designed and balanced to generate amplification products for each of the 26 loci with fragments distinct from the local background noise observed in the amplified material. Because the amplified material was a known standard DNA from human strain 9947, the expected fragments were known and confirmed. However, the limitation to five dyes would make interpretation with some samples difficult because the CXR-labeled D8S1179, FGA, and SE33 allele ranges each overlap significantly with one or more of the other six CXR-labeled loci. This limitation is overcome in Example 2 that employs six fluorescent dyes to permit full separation of the alleles of each locus into a unique size range within each individual dye.

Example 2

25-STR Locus Multiplex

Example 2 displays the co-amplification of 25 distinct human STR loci plus the amelogenin locus, and the separation and detection of the co-amplified products into distinct allele size ranges without overlap of neighboring alleles labeled with the same dye. This locus set includes the complete 13 CODIS loci, 8 addition European, Austrian, and German standard or proposed standard loci, four Penta loci, and amelogenin to allow sex identification. This approach permits a unification of forensic typing methods and the sharing of more useful data between the United States and many nations and organizations throughout the world. The multiplex can be used to analyze DNA samples, then support searching in databases in Europe, the United States, and throughout the world, supporting law enforcement, anti-terrorism, and homeland security efforts in all of these venues.

Fluorescent Detection of Simultaneous Multiplex Amplification of Loci amelogenin, D3S1358, D19S433, D2S1338, D22S1045, Penta B, TH01, D18S51, D1S1656, D10S1248, D2S441, Penta C, D16S539, vWFA31, D21S11, D12S391, Penta D, D5S818, D13S317, D7S820, TPOX, CSF1PO, Penta E, D8S1179, FGA, and SE33 in a 6-color Amplification and Separation and Detection System. This multiplex design example is comprised of the primers that co-amplify the same loci as described in Example 1. It differs in that the loci D8S1179, FGA, and SE33 are amplified with primers pairs containing a primer labeled with a sixth dye for these three loci instead of a ROX-labeled primer as in Example 1. The sixth dye is DyLight 633, although a number of other dyes can be utilized if desired. In addition to this sixth dye, the other dyes in this multiplex are FAM, JOE, TMR, CXR, and CC5.

FIG. 4 illustrates an advantage of the approach taken in development of the multiplex systems of the invention. The dyes used to label the specific loci in each row are listed in the left column (A488 represents ATTO488 dye). The approximate allele sizes for each locus can be determined from the scale shown at the top of the figure. Placement of several highly polymorphic loci, each displaying many alleles in a population of individuals, in a multiplex is highly desirable. However, loss of resolution in the higher molecular weight ranges of DNA fragments during separation creates an upper limit on the workable amplicon size range, thus limiting how many loci labeled with each fluorescent dye can be distinctly separated and analyzed. Increasing the number of dyes is one way to overcome this limitation (an alternate approach is to increase the effective MW range separated by the electrophoresis system). The inclusion of a sixth fluorescent dye conjugated to specific primers for the D8S1179, FGA, and SE33 loci permits the co-amplification and separate visualization to occur without generating amplicons of overlapping alleles, i.e., production of an allele of one locus appearing in the size range of the alleles of another locus with primers labeled in the same dye.

In other words, this 25-locus assay is a Substantially Non-overlapping STR Assay. The value of Substantially Non-overlapping assays is that they essentially eliminate the possibility of confusion arising from overlapping alleles from neighboring loci labeled in the same fashion. Only rare alleles falling outside the STR Locus Size Ranges can cause such confusion. The design of our 27plex assay of Example 5 has 4 such rare overlapping alleles, the 16plex ABI Identifiler assay has at least 6 rare overlapping alleles, and the Powerplex 16plex assay has 8 such rare overlapping alleles. Most of these rare alleles have been reported in the literature based on one or a few occurrences. As such, designing the multiplexes such that they allow large numbers of STR loci to be evaluating while maintaining them as Substantially Non-overlapping assays is a major advantage of the present invention.

With the exception of the assay of Example I, all of the STR assays presented in the Examples are Substantially Non-overlapping. Thus, fragments representing alleles are confidently separated for visualization and analysis either by size or color or both. This is possible because substantial population data in many populations are available for the loci included in the multiplex. Without employing these data, it is either necessary to separate allele ranges substantially from one another permitting fewer highly polymorphic loci displayed in each or color, or when placing them close together, running the risk of substantial overlap of the allele size ranges of neighboring loci of the same color.

In this Example, a DNA template (strain 9947) is amplified simultaneously at the individual loci D3S1358, D19S433, D2S1338, D22S1045, Penta B loci labeled with FAM, the loci TH01, D18S51, D1S1656, D10S1248, D2S441, and Penta C labeled with JOE, the loci D16S539, vWFA31, D21S11, D12S391, amelogenin, and Penta D labeled with TMR, the loci D5S818, D13S317, D7S820, TPOX, CSF1PO, and Penta E are labeled with CXR, and the loci D8S1179, FGA and SE33 are labeled with the a sixth dye in a single reaction vessel. The PCR amplification is performed as described in Example 1. Amplified products are mixed with CC5-labeled size marker, then separated and detected using NetBio's Genebench-FX™ as described in Example 1.

Example 3

35-STR Locus Multiplex Design

Fluorescent Detection of Simultaneous Multiplex Amplification of Loci D3S1358, D19S433, D2S1338, D22S1045, Penta B, TH01, D18S51, D1S1656, D10S1248, D2S441, Penta C, D16S539, vWFA31, D21S11, D12S391, amelogenin, Penta D, D5S818, D13S317, D7S820, TPOX, CSF1PO, Penta E, D8S1179, FGA, SE33, D17S974, D9S1122, D14S1434, D4S2408, D9S2157, D20S1082, D6S1043, D1SGATA113, D10S1435, and D11S4463 in an 8-color Amplification and Separation and Detection System. This 35-plex design includes the 25 STR loci and the amelogenin locus of Examples 1 and 2 plus 9 additional STR loci.

FIG. 5 displays the design employing 8 dyes to label products of amplified sets of loci (see, application. Ser. No. 12/080,746 entitled "Methods for Rapid Multiplexed Amplification of Target Nucleic Acids" incorporated by reference herein). Loci D3S1358, D19S433, D2S1338, D22S1045, and Penta B are labeled with dye 1, TH01, D18S51, D1S1656, D10S1248, D2S441, and Penta C are labeled with dye 2, D16S539, vWFA31, D21S11, D12S391, amelogenin, and Penta D are labeled with dye 3, D5S818, D13S317, D7S820, TPOX, CSF1PO, and Penta E are labeled with dye 4, D8S1179, FGA, and SE33 are labeled with dye 6, D17S974, D9S1122, D14S1434, D4S2408, D9S2157, and D20S1082 are labeled with dye 7, and D6S1043, D1SGATA113, D10S1435, and D11S4463 are labeled with dye 8. The size standard is labeled with dye 5.

The D6S1043 locus is physically close to the SE33 locus on chromosome 6 and therefore may be genetically linked with it. The D6S1043 locus included in this multiplex system is in use in China. The D17S974, D9S1122, D14S1434, D4S2408, D9S2157, D20S1082, D1SGATA113, D10S1435, and D11S4463 loci have been reported by Hill et al. (2009, ibid). These loci are all located a substantial physical (chromosomal) distance from all other loci included in the multiplex set, making genetic linkage with other loci in the multiplex unlikely.

The inclusion of 34 STR loci plus the amelogenin locus in the multiplex system adds significant complexity versus previously developed STR multiplex sets. At least 70 primers are included in the mix resulting in simultaneous co-amplification without deleterious consequences of artifact generation. Eight separate dye labels are incorporated such that fewer loci are amplified with each, thus permitting the high molecular weight amplicons to be limited in size. This, in turn, allows more rapid and accurate separation of the amplified products.

Example 4

Fluorescent Detection of Simultaneous Multiplex Amplification of Loci D3S1358, D19S433, D2S1338, D22S1045, Penta B, TH01, D18S51, D1S1656, D10S1248, D2S441, Penta C, D16S539, vWFA31, D21S11, D12S391, amelogenin, Penta D, D5S818, D13S317, D7S820, TPOX, CSF1PO, Penta E, D8S1179, FGA, SE33, DYS391, D6S1043, DYS439, DYS389II, DYS19, DYS392, DYS393, DYS389I, DYS390, DYS385a, DYS385b, DYS437, and DYS438 In an 8-color amplification, separation and detection system.

This 38-plex design includes the 25 STR loci and the amelogenin locus of Examples 1 and 2, the D6S1043 locus of Example 3, and 11 additional Y chromosome STR loci.

The Y chromosome loci are effective in determining kinship relationships when male to male inheritance is being investigated. The combined autosomal STR and Y STR multiplex provides extra utility in this multi-dimensional analysis. These Y STR loci can be used to establish avuncular relationships, grandfather to grandson relationships, male cousins related through a male-to-male lineage, and male half-sibling relationships from the same father, among other relationships. Y STRs have been used to established kinship over periods of several generations. They are especially helpful in two-person analyses when intervening male relatives are missing from the analysis (e.g., uncle and nephew with no sample from the brother of the uncle who is the father of the nephew). They also provide added value in that they may be used for determination of geographic ancestry of the paternal line. Thus, these loci are extremely useful in investigative analyses and kinship determination.

This example incorporates the use of eight dyes to label products of amplified sets of loci. This provides the ability to separate and detect discretely the amplified products generated with each dye label.

FIG. 6 displays the design employing 8 dyes to label products of amplified sets of loci. Loci D3S1358, D19S433, D2S1338, D22S1045, and Penta B are labeled with dye 1, TH01, D18S51, D1S1656, D10S1248, D2S441, and Penta C are labeled with dye 2, D16S539, vWFA31, D21S11, D12S391, amelogenin, and Penta D are labeled with dye 3, D5S818, D13S317, D7S820, TPOX, CSF1PO, and Penta E are labeled with dye 4, D8S1179, FGA, and SE33 are labeled with dye 6, DYS391, D6S1043, DYS439, DYS389II, DYS19, and DYS392 are labeled with dye 7, and DYS393, DYS389I, DYS390, DYS385, DYS437, and DYS438 are labeled with dye 8. The size standard is labeled with dye 5.

The inclusion of 38 STR loci plus the amelogenin locus in the multiplex system adds significant complexity versus previously developed STR multiplex sets. At least 76 primers are included in the mix resulting in simultaneously co-amplification without deleterious consequences of artifact generation. Eight separate dye labels are incorporated such that fewer loci are amplified with each, thus permitting the high molecular weight amplicons to be limited in size. This, in turn, allows more rapid and accurate separation of the amplified products.

Example 5

Locus Selection and Multiplex Design

STR loci were selected for inclusion in a 27-locus multiplex assay based primarily on their accepted use in US and European databases. These loci are listed in Table 5 and include the 13 CODIS core STR loci (Budowle et al. Population Data on the Thirteen CODIS Core Short Tandem Repeat Loci in African-Americans, US Caucasians, Hispanics, Bahamians, Jamaicans, and Trinidadians. J Forensic Sci. 1999; 44:1277-86), the European standard 12 STR loci (7 of which overlap with the CODIS loci), the amelogenin locus, the D2S1138 and D19S433 loci used in the Austrian database and the SE33 locus used in the German database (Parson et al. Efficient DNA database laboratory strategy for high throughput STR typing of reference samples. Forensic Sci Int. 2001; 122(1):1-6; Schneider. Expansion of the European Standard Set of DNA Database Loci—the Current Situation. Profiles in DNA. 2009; 12(1):6-7. In addition, the Penta D, Penta E, and DYS391 loci were included, which were recently proposed for inclusion in an expanded CODIS core STR set (Hares. Expanding the CODIS core loci in the United States. Forensic Sci Int Genet. 2012; 6(1):e52-4), the D6S1043 locus commonly used in China, and an additional pentanucleotide locus, Penta C, for its large repeat length were also included.

Creating a multiplex design to permit co-amplification of 27 loci required iterative primer design and testing. Amplified products were less than 500 bases because forensic sample extracts sometimes contain DNA samples no larger than this length. Minimum and maximum amplicon length requirements for each locus were determined from review of the NIST STRbase data and the NCBI DNA sequences available for each locus (National Center for Biotechnology Information Homepage. In several cases, the amplicon ranges were substantially expanded in this multiplex compared to the ranges represented by the commercially available allelic ladders as new alleles have been discovered following introduction of commercial kits. Despite the inclusion of eleven additional loci in the multiplex described in this example and the enlargement of the designated amplicon ranges of individual loci, the 27-plex assay has only four cases of potential overlap of alleles across adjacent loci, and these would only occur with very rare alleles. This compares favorably to the Identifiler Kit, with six pairs of neighboring loci with potential overlap, and the Powerplex 16 System with eight—both kits have much lower STR Locus Size Range Sums and Multiplex Densities with more locus-to-locus overlap as compared to the 27 locus assay.

To accommodate the large number of loci and the enlarged amplicon size ranges for the selected loci, six fluorescent dyes were used to label the PCR primers. The multiplex design is displayed in schematic format in FIG. 7. FIG. 7 shows the 27-locus multiplex design. The approximate size ranges of amplified products representing alleles for all 27 loci are displayed above the size marker. Each size marker fragment is shown with its corresponding base size. The fluorescent dye used to label each amplicon is indicated to the left of each respective locus name. The following locus abbreviations are employed: A=amelogenin, D10=D10S1248, D22=D22S1045, Y=DYS391

TABLE 5

| | CODIS Core 13 STR Loci | European EDNAP/ENFSI Standard STR Set | Austrian German | CODIS Expanded Set | 27-locus Example of the Invention |
|---|---|---|---|---|---|
| 1 | | amelogenin | | amelogenin | amelogenin |
| 2 | CSF1PO | | | CSF1PO | CSF1PO |
| 3 | | D1S1656 | | D1S1656 | D1S1656 |
| 4 | | D2S441 | | D2S441 | D2S441 |
| 5 | | | D2S1338 (Austrian) | D2S1338 | D2S1338 |
| 6 | D3S1358 | D3S1358 | | D3S1358 | D3S1358 |
| 7 | D5S818 | | | D5S818 | D5S818 |
| 8 | D7S820 | | | D7S820 | D7S820 |
| 9 | | D8S1179 | | D8S1179 | D8S1179 |
| 10 | | D10S1248 | | D10S1248 | D10S1248 |
| 11 | | D12S391 | | D12S391 | D12S391 |
| 12 | D13S317 | | | D13S317 | D13S317 |
| 13 | D16S539 | | D16S539 (Austrian) | D16S539 | D16S539 |
| 14 | D18S51 | D18S51 | | D18S51 | D18S51 |
| 15 | | | D19S433 (Austrian) | D19S433 | D19S433 |
| 16 | D21S11 | D21S11 | | D21S11 | D21S11 |
| 17 | | D22S1045 | | D22S1045 (not required) | D22S1045 (not required) |
| 18 | FGA | FGA | | FGA | FGA |
| 19 | | | SE33 (German) | SE33 (not required) | SE33 (not required) |
| 20 | TH01 | TH01 | | TH01 | TH01 |
| 21 | TPOX | | | TPOX (not required) | TPOX (not required) |
| 22 | vWA | vWA | | vWA | vWA |
| 23 | | | | DYS391 | DYS391 |
| 24 | | | | | D6S1043 |
| 25 | | | | | Penta C |
| 26 | | | | | Penta D |
| 27 | | | | | Penta E |

Example 6

Five, Six, and Eight Color Optical Detection and Electrophoresis Instrumentation The amplified products of Example 1 were separated and detected using NetBio's Genebench-FX™. This instrument was developed and optimized for STR analysis, DNA sequencing, and SNP typing and has been ruggedized for laboratory and field-forward utilization It is described in Giese et al. (2009). "Fast multiplexed polymerase chain reaction for conventional and microfluidic short tandem repeat analysis." J Forensic Sci 54(6): 1287-96, as well as in application Ser. No. 11/132,712 entitled "Ruggedized Apparatus for Analysis of Nucleic Acids and Proteins," application Ser. No. 12/080,745 entitled "Plastic Microfluidic Separation and Detection Platforms," application Ser. No. 12/080,751 entitled "Integrated Nucleic Acid Analysis," and application. Ser. No. 13/044,485 entitled "Unitary Biochips," all of which have been incorporated by reference herein. To 2.7 µL of each amplified product, 9.87 µL formamide and 1.02 µL of CC5-ILS (internal lane standard, Promega Corporation, catalog #DG1521) were added. Samples were loaded into the separation biochip and electrophoretically moved into the separation channels by applying a 350 V/cm electric field for 90 sec. This was followed by the application of a 150 V/cm electric field along the separation channel to separate the DNA fragments. All separations were carried out at 50° C.

The dyes attached to the separated products were excited with a solid state (488 nm) laser and the fluorescence was wavelength separated by dichroic and bandpass filters, and detected by a set of five photomultiplier tubes. The resulting profiles were subjected to data processing and color separation software to display fragments represented in their individual dyes.

The Genebench FX instrument is ruggedized for field forward applications, has low power consumption, and is CE marked under the Low Voltage Directive 73/23/EEC. To perform separation and detection, the microfluidic biochip is placed in the biochip chamber of the instrument. The biochip chamber provides coupling of the high voltage, excitation and detection, and thermal subsystems to the biochip. High voltage is applied to the biochip through a set of electrode boards. Contact between the instrument and biochip is achieved by pogo pin connections on the cover of the chip chamber. The high voltage subsystem allows up to 10 KV to be applied to the separation channels, and, optionally, up to 1.5 KV to be applied to the sample loading channels. The samples can also be loaded into the separation channels using pneumatic pressure. A pre-programmed script allows automated operation by controlling the switching configuration, voltage levels, and timing of the power supplies. A set of resistive foil heaters is mounted to a heater plate within the biochip chamber to provide accurate and consistent heating of the biochip.

The optical system consisting of a laser, detectors, and optical train provides laser excitation and fluorescent detection of dye labeled DNA molecules that travel electrophoretically along the separation channel to the excitation and detection window of the biochip. Optical excitation is accomplished by a 200 mW, 488 nm laser (Coherent, Santa Clara, Calif.). Multicolor detection is accomplished by a set of dichroic mirrors, bandpass filters (Omega Optical, Brattleboro, Vt.), and 5 photomultiplier tubes (PMTs) (Hamamatsu, Bridgewater, N.J.). A set of lenses, a galvanometer, and a 10× objective couples the biochip to the laser and detectors. Detection is accomplished using a step-stare approach in which the galvanometer is positioned to excite the first channel and to collect fluorescence from this channel for a fixed integration time. The galvanometer is then positioned to excited and collect fluorescence from the adjacent channel, and this process is repeated until all channels in the biochip are interrogated. In addition to single- or multi-color quantitation, this optical configuration is capable of performing 4-color DNA sequence analysis, 1-5 color SNP analysis, and 4- and 5-color multiplexed DNA fragment sizing assays.

The amplified products of 6- and 8-color reactions were separated on an instrument based on modifications of the Genebench FX optical train. This approach is described in U.S. Pat. No. 8,018,593 entitled "Integrated Nucleic Acid Analysis." The modified instrument is based on the development of a detection system consisting of a spectrograph with a dispersion grating and linear array detector to replace the dichroic mirrors, bandpass filters, and discrete photomultiplier tube detectors of the Genebench FX instrument.

Figure 8A:
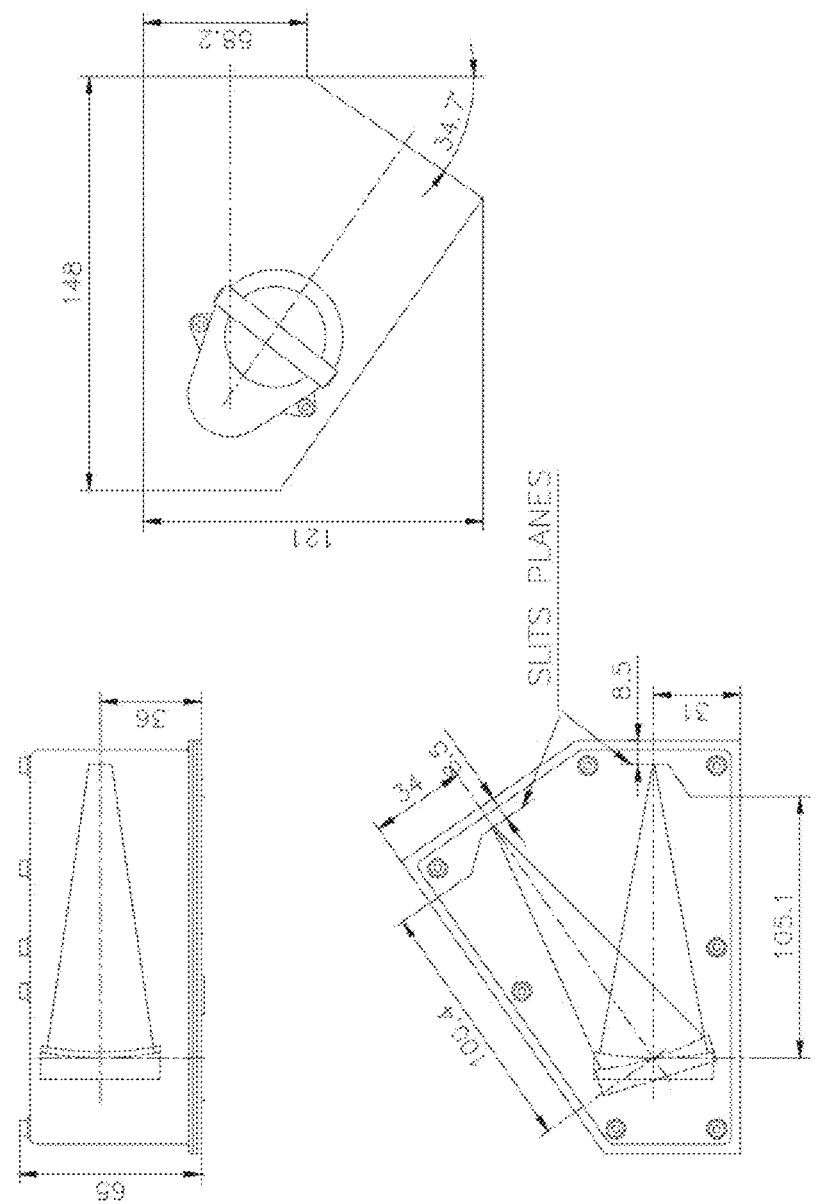
FIG. 8A illustrates drawings of the spectrograph of the invention.

A spectrograph (FIG. 8A) with the following specifications was selected:

Aberration corrected concave holographic grating. This grating design allows for a spectrograph with a single optical element.

Fixed grating mount. The grating is rigidly mounted within the spectrograph and locked in place. Adjustment of grating orientation for wavelength calibration is performed by releasing a locking screw on the grating mount and rotating the grating. Rigidly mounting the grating increases the ruggedness of the spectrograph.

Focal length. A 100 mm focal length spectrograph is selected to meet both the resolution requirements (1 to 5 nm) while maintaining a minimal footprint.

Pinhole. A 1.0 mm pinhole at the entrance to the spectrograph allows for maximal light collection and background light reduction.

Output window. An output window of 32 mm×10 mm allows the wavelength separated light to be imaged to a linear array detector.

Detector mounting. Four threaded screw holes are located about the output window of the spectrograph for mounting a linear array detector.

Figure 8B:
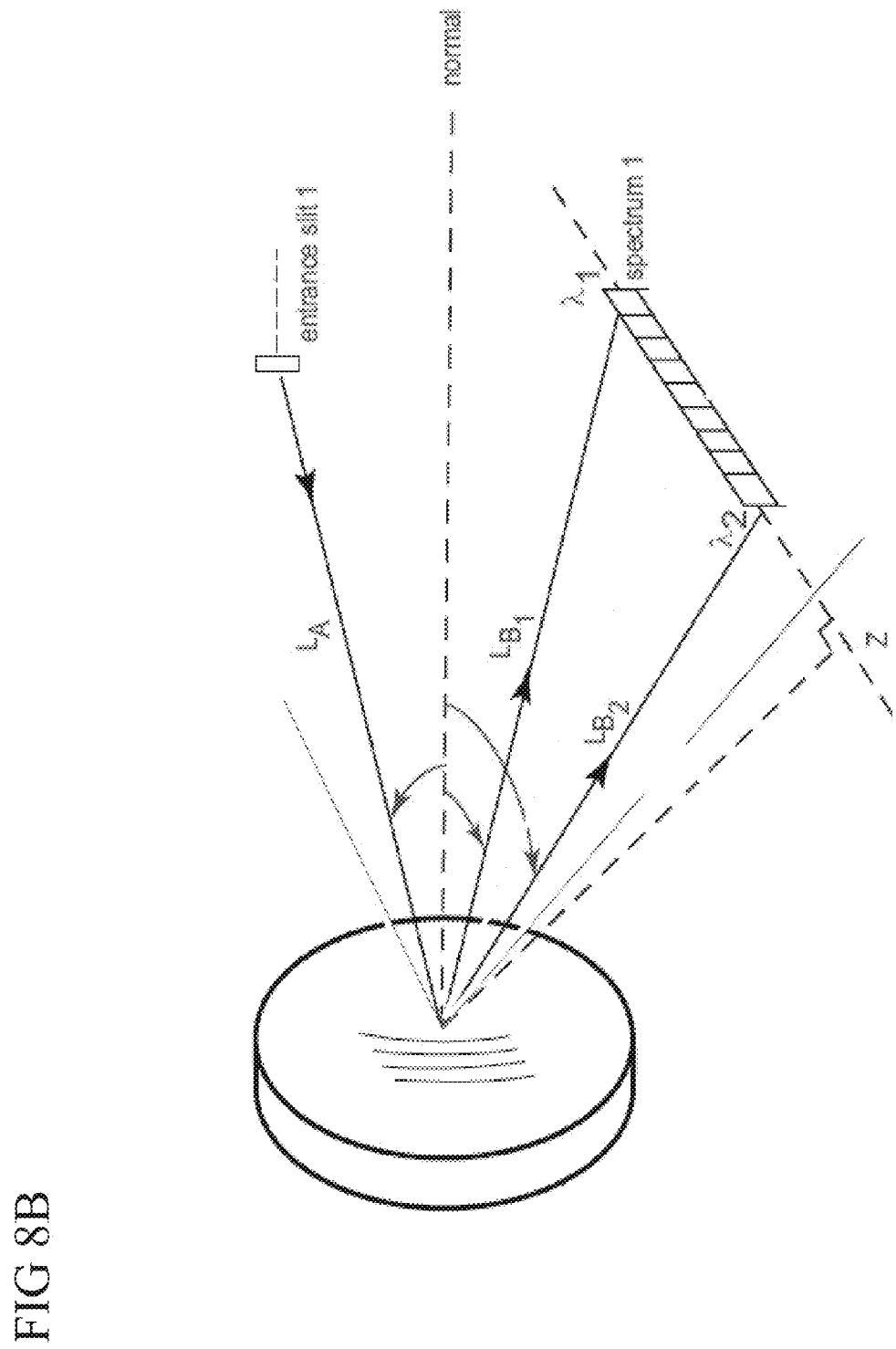
FIG. 8B depicts an aberration-corrected concave holographic grating selected for use with the spectrograph.

An aberration-corrected concave holographic grating was selected for use with the spectrograph. The grating specifications are:

Flat field at image plane. These gratings collimate and refocus light from the entrance slit onto a plane surface for direct imaging onto linear array detectors (FIG. 8B).

Size. A 42.4×42.4 mm grating allows a maximal collection of light.

Groove density. A 1200 grooves/mm grating allows the wavelength range and resolution requirements to be met.

Blaze wavelength. A blaze angle of 450 nm is selected to achieve a peak grating efficiency that is centered about the visible range.

Dispersion. A 7 nm/mm dispersion, defined by the groove density, is achieved. This allows a wavelength range of 224 nm to be imaged across the 32 mm image plane at the output.

Wavelength range—A wavelength range of 350 to 850 nm allows separation of the emission spectra of visible dyes (ranging from 520 to 700 nm), and detection of the laser emission (488 and 514 nm) for wavelength calibration.

Figure 8C:
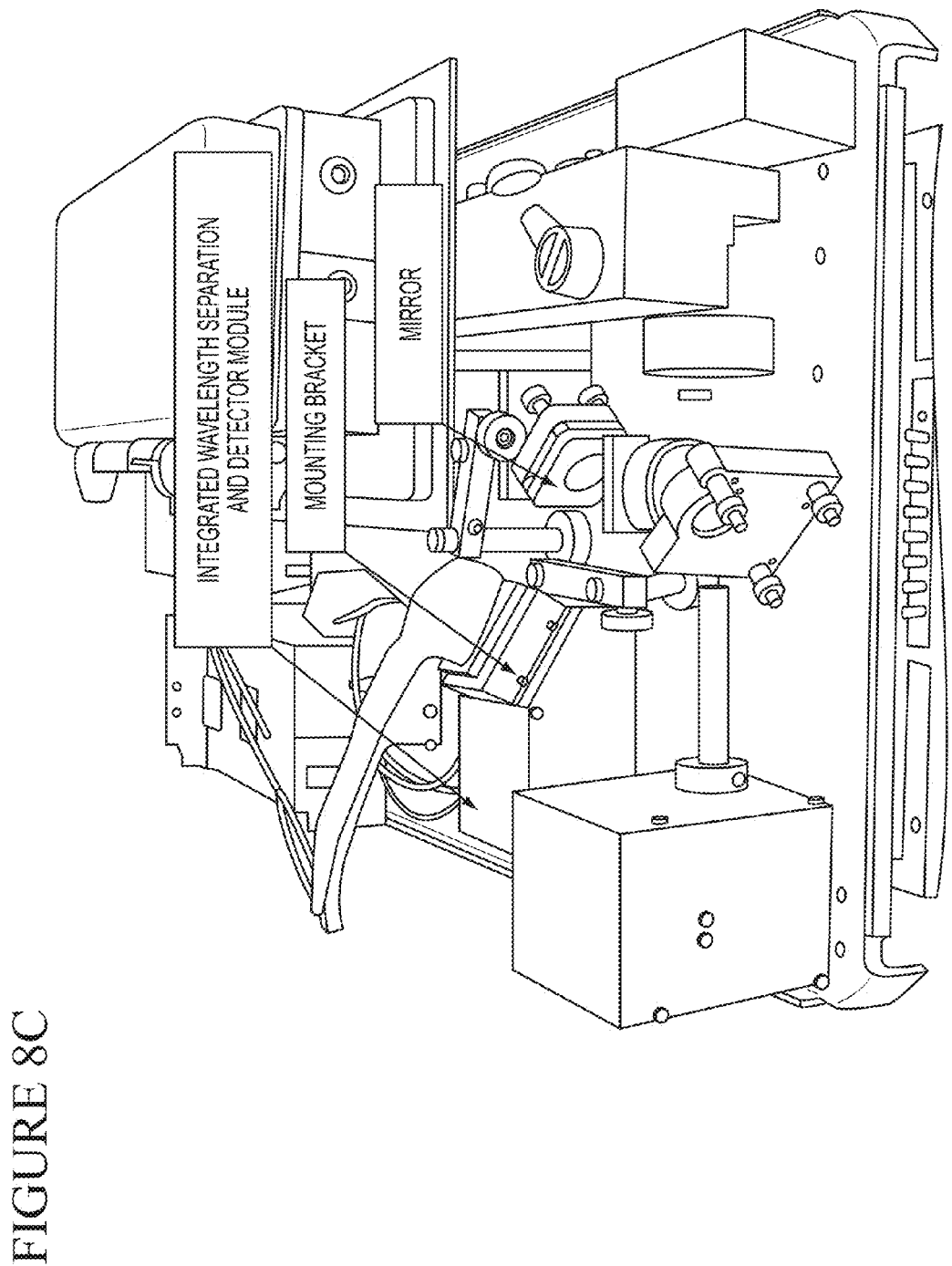
FIG. 8C shows a mirror allowing the instrument to be readily configured for operation with the integrated wavelength module or the existing filter and discrete PMTs.
Figure 8D:
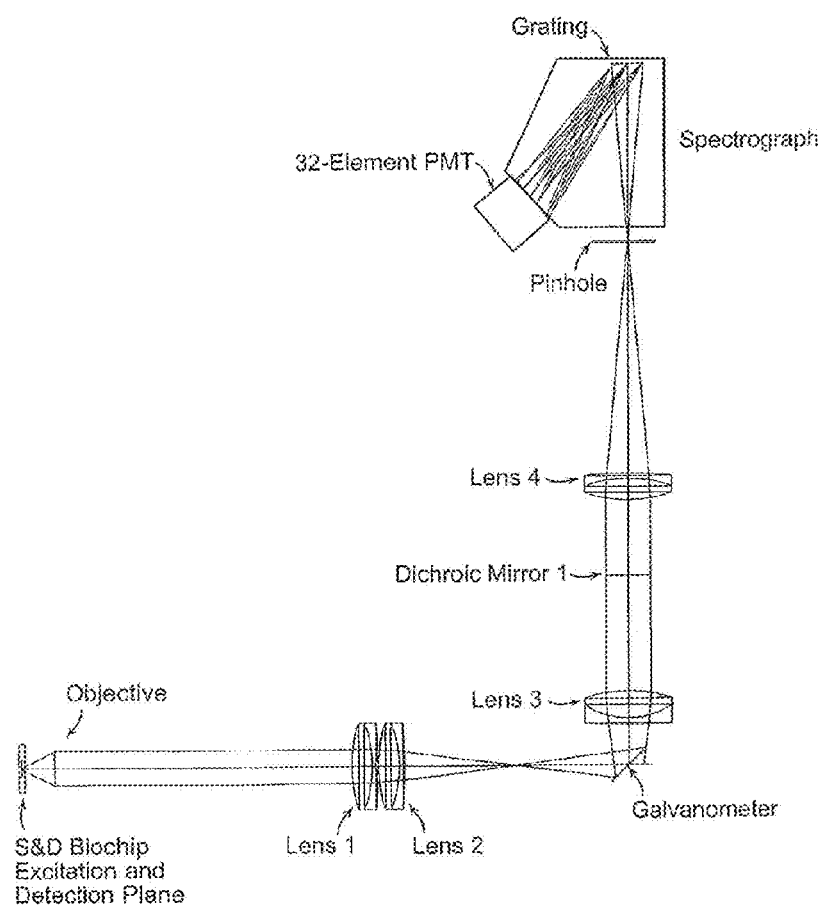
FIG. 8D shows the beam path of the 6- and 8-color instruments.

The optical baseplate of Genebench FX was modified to accommodate the integrated wavelength separation and detection module. A mounting bracket was designed and fabricated to mount the integrated detection module to the baseplate. The integrated detection module is position on the baseplate such that the location of the input port preserves the detection path length of Genebench. A mirror on a custom designed and fabricated mount is installed on the baseplate. The mirror allows the instrument to be readily configured for operation with the integrated wavelength module or the existing filter and discrete PMTs (FIG. 8C). These modifications of the optical train result in the beampath shown in FIG. 8D.

In some embodiments, a total of 9, 10, 11, 12, 13, 14, 15, 16, 17, 18, 19, 20, 21, 22, 23, 24, 25, 26, 27, 28, 30, 35, 40 or more fluorescent dyes are utilized to label primers. Various configurations and combinations of spectrographs, grating, detectors and lasers can be applied to generate and collect fluorescence from these numbers of fluorescent dyes. The specification of the grating parameters allows wavelength range and the center wavelength defines the wavelength range and central wavelength. A maximal number of dyes can be detected by expanding the wavelength range of the grating. Compressing the wavelength range allows for higher wavelength resolution. Shifting of the wavelength range to lower wavelengths will allow for detection of ultraviolet dyes, while a shift of the wavelength range to longer wavelengths allows for detection of near infrared and infrared dyes. The ability to adjust both the center wavelength and wavelength range with the grating allows for the detection of UV, visible, near infrared and infrared dyes. Multiple spectrograph, grating and detector modules can be implemented in tandem to achieve wide wavelength ranges and high wavelength resolution detection to accommodate the detection of a high number of dyes. In this configuration the incoming fluorescence is split with a dichroic mirror and each portion of this light is then incident on one of the spectrograph, grating and detector modules. The appropriate selection of a linear detector module, including PMT, avalanche photodiodes, CCD allows for efficient detection of fluorescence.

In general, shorter wavelength laser excitation is more efficient in generating fluorescence from UV and visible dyes, while longer wavelength excitation is more efficient for generating fluorescence from near infrared and infrared dyes. To be able to simultaneously detect from a large number of dyes, multiple laser excitation wavelengths, from multiple laser sources may be used in tandem. In taking advantage of wide wavelength ranges and ranges of wavelength outside of the visible, an optical system matched with a wide range of dyes such as Cy7 and Cy7.5 (773 and 808 nm respectively) and infrared dyes with maximum wavelengths of 800 to 900 nm enables a large set of fluorescent dyes to be utilized to label primers.

Example 7

Dye Selection

In selecting fluorescent dyes for 6-dye multiplex development, a working 5-dye set was built and new dye candidates were evaluated for compatibility with this collection. The upper portion of Table 6 lists the 5-dye set of FAM, JOE, TMR, CXR, and CC5 along with the excitation and emission wavelength maxima for each dye.

TABLE 6

Examples of fluorescent dyes for inclusion in multiplex sets.

| Fluorescent Dyes | $Exc_{max}$* (nm) | $Em_{max}$** (nm) |
|---|---|---|
| FAM ™ | 495 | 522 |
| JOE ™ | 528 | 554 |
| TAMARA ™ | 546 | 574 |
| CXR ™ | 580 | 605 |
| CC5 ™ | 645 | 669 |
| 5-FAM ™ | 493 | 522 |
| Fluorescein | 495 | 522 |
| Atto ™ 488 | 501 | 523 |
| R110 | 501 | 525 |
| TET ™ | 522 | 538 |
| R6G | 529 | 549 |
| VIC ® | | 552 |
| HEX ™ | 535 | 553 |
| TAMRA ™ ([F]dNTP) | 555 | 572 |
| NED ™ | 553 | 573 |
| NED ™ | 553 | 575 |
| TAMRA ™ ([F]dNTP) | 560 | 583 |
| Lissamine-rhodamine | 572 | 590 |
| PET ® | | 591 |
| ROX ™ | 587 | 607 |
| DyLight ™ 594 | 592 | 616 |
| HiLyte Fluor ™ 594 | 593 | 616 |
| SID | | 620 |
| Atto ™ 594 | 601 | 627 |
| Atto ™ 610 | 615 | 634 |
| Atto ™ 620 | 619 | 643 |
| Atto ™ Rho14 | 625 | 646 |
| DyLight ® 633 | 623 | 647 |
| LIZ ® | | 655 |
| Cy5.5 | 673 | 692 |
| HiLyte ™ Fluor 680 | 680 | 699 |
| WellRed ™ D3 | 685 | 706 |
| Cy 7 | 750 | 773 |
| Cy 7.5 | 788 | 808 |

*$Exc_{max}$: excitation wavelength maximum in nanometers.
**$Em_{max}$: emission wavelength maximum in nanometers.

Figure 9:
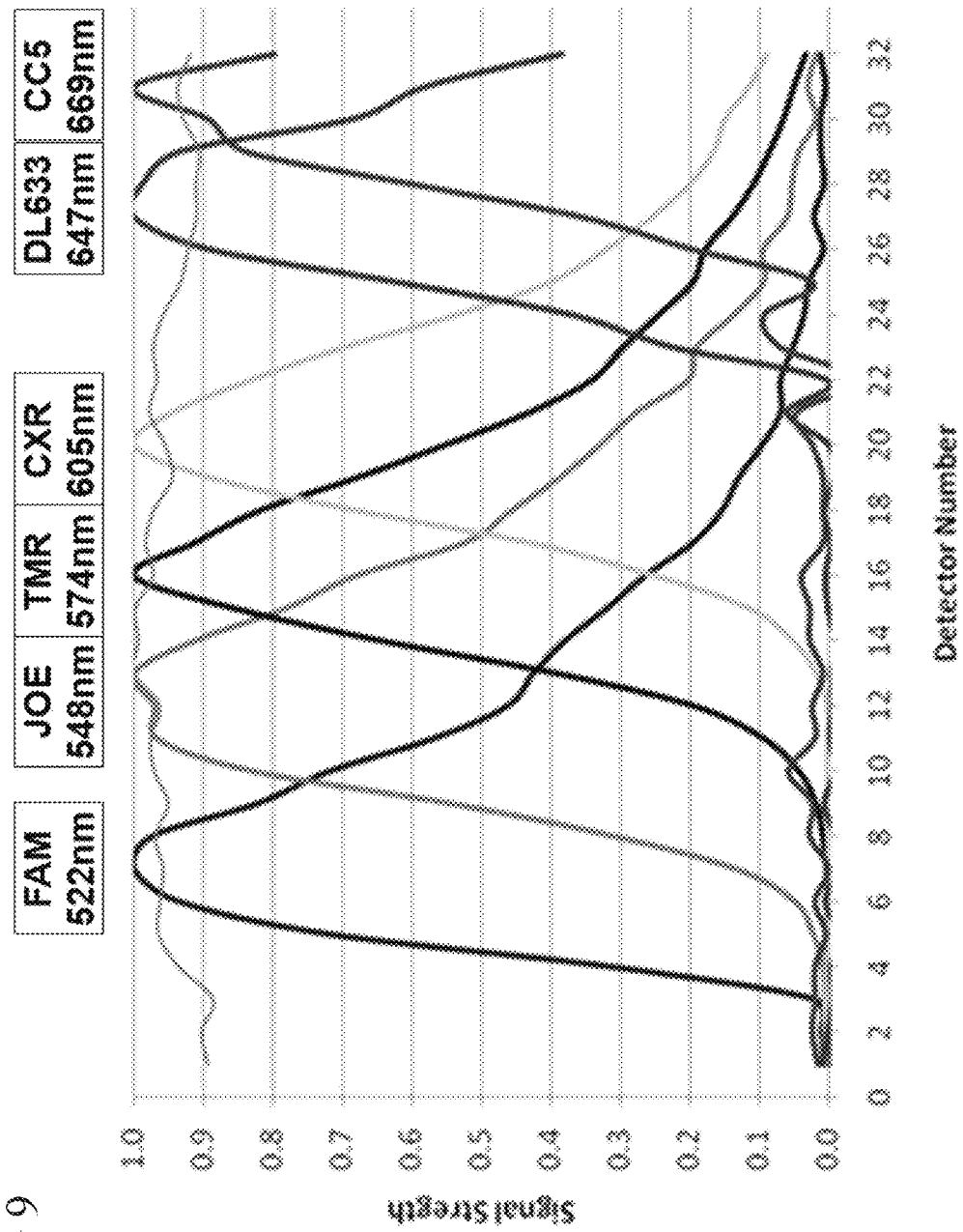
FIG. 9 illustrates emission spectra diagrams for the core 5-dye set and the DyLight 633 (DL633) dye. Detector channels are written across the bottom of the figure. Relative signal strength is shown on the Y-axis. The numbers in each boxed area represent the maximum emission wavelength (nm) for each respective dye.

FIG. 9 displays the emission spectra observed with each of the five core dyes plus DyLight 633. With these six dyes, it was possible to detect each dye distinctly with four or more spectrograph channel separation between each neighboring pair of dyes. This amount of separation permitted us to create a color correction matrix that resulted in complete separation of all six colors. As the ATTO 488-labeled product generated a stronger output emission than the FAM-labeled version of the same product, and both dyes emit at similar wavelengths, the FAM dye was replaced with the ATTO 488 dye in the multiplex set.

Example 8

Eight-Color Dye Detection and Separation

Figure 10:
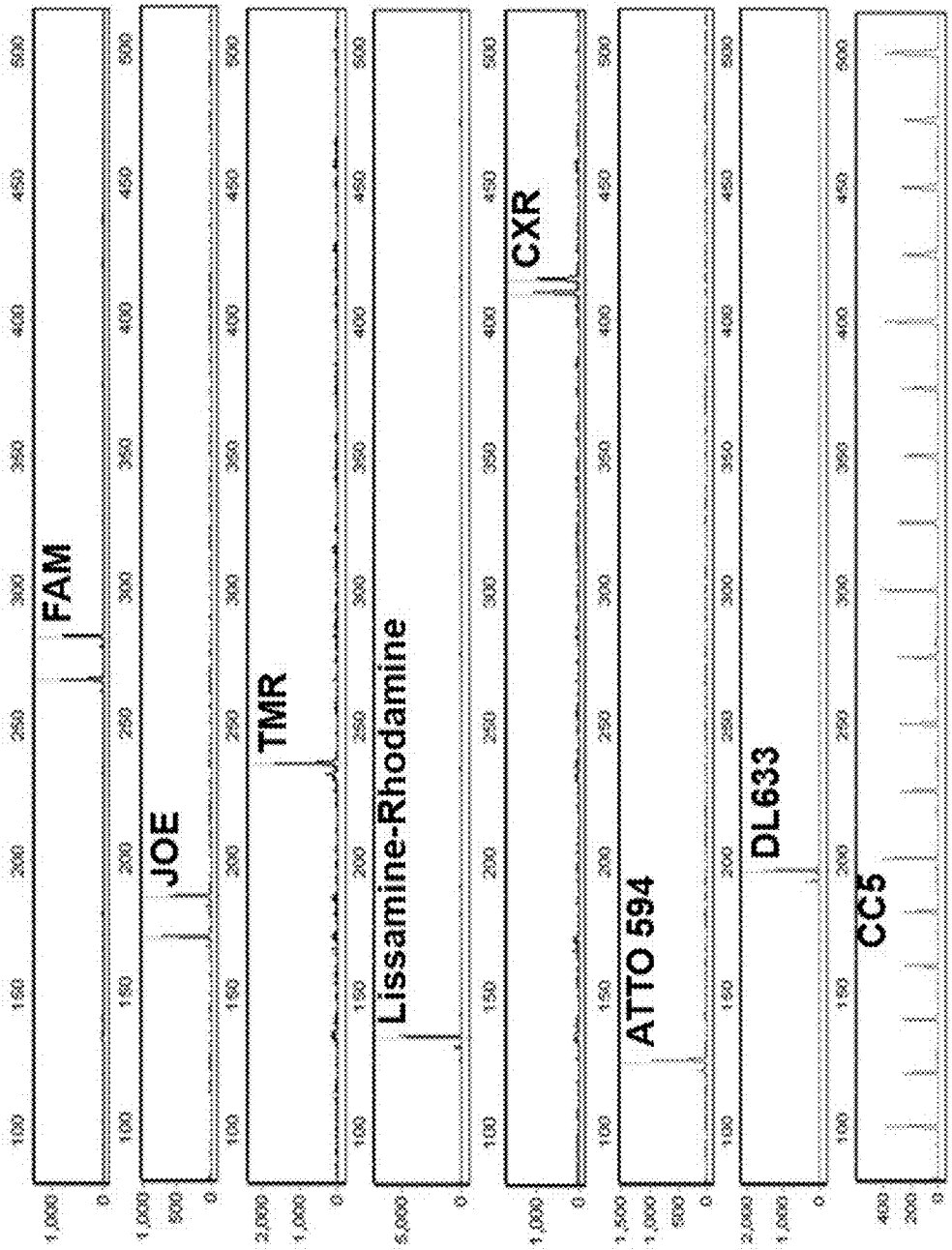
FIG. 10 illustrates baseline-subtracted and color-corrected electropherogram of 8-color separation of amplified products. Amplified products were separated and detected on the 8-color instrument of Example 6. The amplified fragments are indicated by the dye used to label them in each panel. As used throughout the specification and drawing "ATTO™ 594" refers to a dye in the ATTO™ line of dyes which are proprietary to Atto-Tec GmbH.

The utility of the modified optical system to detect simultaneously STR products labeled with 8 fluorescent dyes was evaluated. The eight selected dyes were those discussed in Example 7 plus the lissamine-rhodamine dye with an emission wavelength maximum of 590 nm and the ATTO 594 dye with an emission wavelength maximum of 627 nm. To test this format, distinctly sized amplification products were created for each of eight separate primer pairs with each primer pair consisting of one unlabeled and one labeled primer with the label being selected from one of eight different fluorescent dyes, respectively. Following development and application of a color correction matrix to resolve overlapping spectral signals, clean signals were obtained for each of the dyes employed (FIG. 10).

Example 9

Monoplex and Miniplex Testing

Multiplex construction occurred in a number of stages and generally followed a strategy of building several core sets of loci from monoplexes, then building upon those sets as described in our previous work (Krenke et al. Validation of a 16-locus fluorescent multiplex system. J Forensic Sci. 2002; 47(4):773-85; Lins et al. Development and population study of an eight-locus short tandem repeat (STR) multiplex system. J Forensic Sci. 1998; 43(6):1168-80; Lins et al. Multiplex Sets for the Amplification of Polymorphic Short Tandem Repeat Loci—Silver Stain and Fluorescence Detection. BioTechniques. 1996; 20(5):882-9. First, primer pairs for monoplex amplification of each individual locus were designed as described in Materials and Methods. Monoplex performance was tested using 0.5 µM forward and 0.5 µM reverse primers with one primer of each pair labeled with a fluorescent dye selected from the dye set of FAM, JOE, CXR, and ROX.

Groups of primer pairs that generated strong amplification products without creating significant artifacts (except for the typical stutter and incomplete non-template addition (iNTA) exhibited by STR loci) were combined to test small sets of primer pairs for four to six loci simultaneously (i.e., miniplex(es)) (data not shown). In most cases, no unanticipated amplified genome sequences (i.e. artifacts) were created by co-amplification. Some sets displayed artifacts and such results required primer redesign and renewed monoplex testing. The analysis of the amplification products of individual pair-wise combinations of primers revealed which primers were involved in generation of the artifacts. Redesigned primers that passed the monoplex evaluation were retested in the small multiplex format to identify stronger candidate combinations for use in the full multiplex at a later stage. Failed attempts at any stage of this development, including combinations generating artifact fragments, required redesign at the monoplex locus stage with testing at both the monoplex and multiplex stages.

Example 10

Artifact Diminution or Removal: iNTA

STR locus amplification often displays stutter artifacts. These artifacts are generally, but not always, one repeat length shorter than the authentic alleles (Klintschar et al. Polymerase slippage in relation to the uniformity of tetrameric repeat stretches. Forensic Sci Int. 2003; 135(2):163-6; Shinde et al. Taq DNA polymerase slippage mutation rates measured by PCR and quasi—likelihood analysis: (CA/GT) n and (A/T) n microsatellites. Nucleic Acids Res. 2003; 31(3):974-80). The loci selected for national and international databases, and thus for this work, are known to have amounts of stutter that can be distinguished from true alleles in DNA profiling of single source samples under standard copy number evaluations.

Incomplete nontemplate nucleotide addition following completion of template-dependent polymerization is a second artifact commonly observed in STR amplification products (Clark Novel non-templated nucleotide addition reactions catalyzed by prokaryotic and eukaryotic DNA polymerases. Nucleic Acids Res. 1988 Oct. 25; 16(20):9677-86; H. DNA Polymerase-catalyzed addition of nontemplated extra nucleotides to the 3' of a DNA fragment. DNA and Cell Biology. 1993; 12(8):763-70; Magnuson et al. Substrate nucleotide-determined non-templated addition of adenine by Taq DNA polymerase: implications for PCR-based genotyping and cloning. BioTechniques. 1996 October; 21(4):700-9). This artifact is observed as a second fragment one base smaller than the authentic allele. Its presence generally lowers the peak height of the true allele and may create confusion by the appearance of two fragments representing one allele. When initial primer design did not accomplish full template addition, the DNA sequence 5% GTTTCTT-3' recommended by Brownstein (Brownstein et al. Modulation of non-templated nucleotide addition by Taq DNA polymerase: primer modifications that facilitate genotyping. BioTechniques. 1996 June; 20(6):1004-6, 8-10) was added to the 5' terminus of the unlabeled primer in a primer pair to stimulate more complete non-templated addition. In several cases, the addition of just a 5'-terminal-G was tested to accomplish the same effect. An alternate approach in some cases was to reverse the labeled and unlabeled primers in the primer pair to create an alternative 5' terminus of the unlabeled primer. An example of iNTA reduction is displayed in FIG. 11.

Figure 11A:
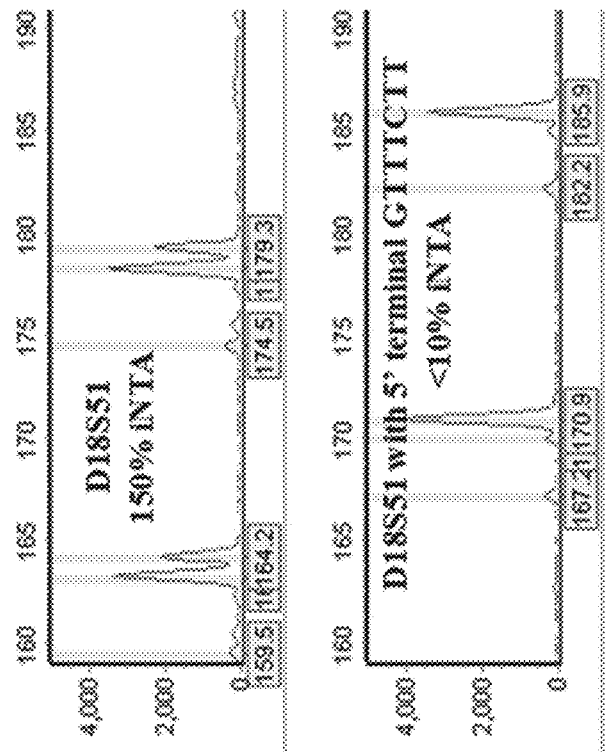
FIG. 11A illustrates the effect of GTTTCTT tail addition to the 5' terminus of the unlabeled primer to reduce iNTA.
Figure 11B:
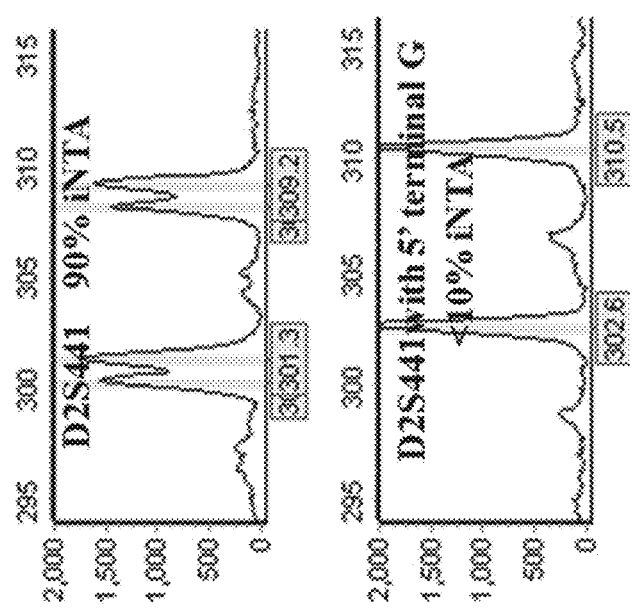
FIG. 11B illustrates the effect of G-tail addition to the 5'-terminus of the unlabeled primer to reduce iNTA.
Figure 11C:
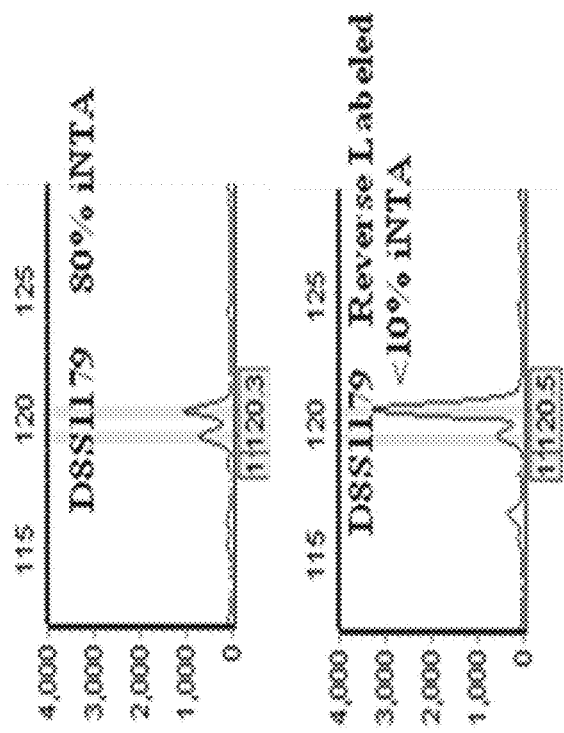
FIG. 11C illustrates the effect of exchanging the dye label from one primer to the other of the D8S1179 primer pair.

FIG. 11A illustrates the GTTTCTT tail addition to reduce iNTA. Upper panel displays D18S51 primer pair amplification product without addition of 5'-GTTTCTT-3' sequence tail to the 5'-terminus of the unlabeled primer. The lower panel shows the product using the modified primer pair. This change reduced the iNTA from approximately 150% in the upper panel to less than 10% in the lower panel. It also increased the fragment length. FIG. 11B illustrates G-tail addition to the 5' terminus of the unlabeled primer to reduce iNTA. Upper panel displays D2S441 primer pair amplification product without addition of 5'-G-3' sequence tail to the 5'-terminus of the unlabeled primer. The lower panel shows the product using the modified primer pair. This change reduced the iNTA from approximately 90% in the upper panel to less than 10% in the lower panel. It also increased the fragment length. FIG. 11C illustrates the product of reversing the labeled primer in the primer pair to reduce iNTA. Upper panel displays D8S1179 primer pair amplification products with the original ROX dye labeling scheme. The lower panel shows the product using the opposite primer in the primer pair as ROX-labeled. This change reduced the visible iNTA from approximately 80% in the upper panel to less than 10% in the lower panel. It does not alter apparent fragment length, but such alterations in apparent fragment can occur depending on sequence variation in the amplified product.

STR artifacts including but not limited to iNTA, stutter, and amplicons due to unintended interaction of primers with nucleic acids are related to primer sequences but also to PCR reaction conditions. Enzyme, buffer, and cycle times and temperatures (and instrument-driven temperature ramp rates) can have significant effects on artifact creation and diminution. Relative signal strength of individual amplicons can also be affected by these factors. Accordingly, in developing STR multiplexes, it is important to consider optimizing primers based on a given set of amplification conditions. For example, an optimal multiplex for a 90 minute PCR reaction may well require modification for similar performance in a 20 minute PCR reaction.

Example 11

Removal of Artifacts from Multiplex Amplification Products

Amplification artifacts arise from the unintended interaction of two primers, at least one labeled, with genomic sequences that, for at least one of the primers involved, are not the intended hybridization target in the primer design. Such artifacts can be removed by first identifying the primer involved in artifact generation. This can be achieved by removing one primer or primer pair at a time from the full multiplex to associate the removal of specific primers with the removal of specific artifacts. Once candidate primers for artifact generation are identified, the two candidate primers can be used to amplify samples in the absence of other primers to confirm their role in artifact generation. Re-design of one or both primers, followed by re-testing, often removes the artifact(s) while retaining amplification of all multiplex loci. Efforts to rebalance the representation of multiple loci in a multiplex are often necessary following inclusion of the redesigned primers into the multiplex primer set.

Figure 12B:
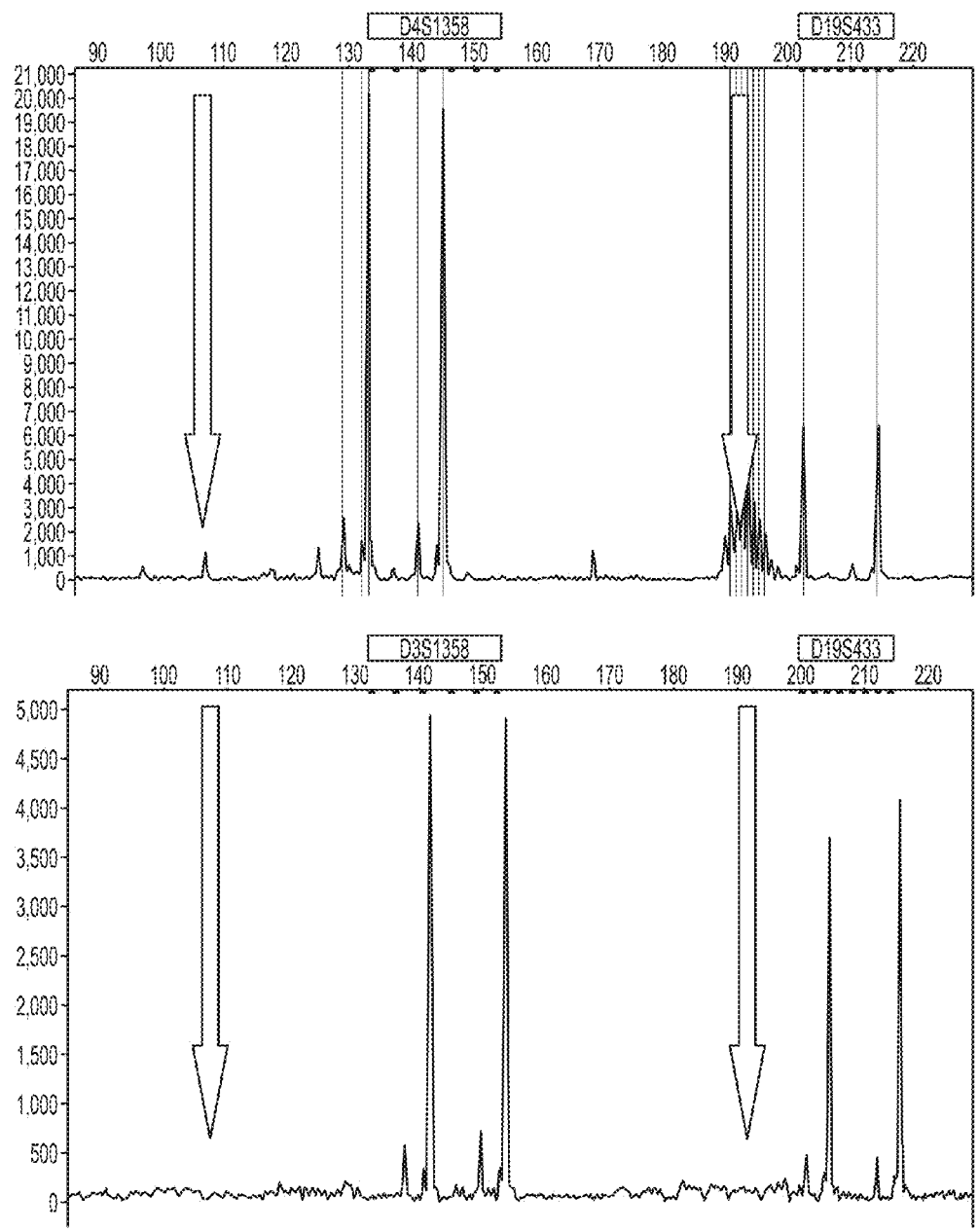
FIG. 12B denotes and enlarged view of the presence of two artifacts (under arrows in left panel) prior to artifact elimination and their absence following artifact elimination (under arrows in right panel) in a six-dye 26-locus multiplex amplification product displayed in 5 colors following separation on the GeneBench FX instrument.

FIGS. 12A, 12B, and 12C display detection of a 6-color amplification product with the 5-color GeneBench FX detection instrument. The DL633-labeled sample amplification fragments and the CC5-labeled size fragments are detected in the same PMT channel. FIG. 12A illustrates two cases of artifact generation. Note the relatively weak fragment labeled with ATTO488 and located at 107 bases (B107) and the series of ATTO488-labeled fragments around the position of 193 bases (B193). In the left panel of FIG. 12B these same artifacts are illustrated in enlarged fashion. The right panel of FIG. 12B displays amplification following replacement of two individual primers with primers of modified sequences. FIG. 12C illustrates the sample amplification product balance retention following primer replacement.

Example 12

Dye Selection to Improve Amplification Product Intensity

Several different methods can be used to attempt to increase amplification product intensity from an individual locus in the context of multiplex amplification. For examples, primer redesign to bind a new genomic sequence or to provide a more stable hybridization can be employed. Alternately, an increase or decrease in primer concentration of the primer for a locus can change product intensity relative to other loci. Sometimes modification of the primer concentration of primers for other loci or the overall mixed primer concentration can alter amplification product intensity. Modification of the protocol, including lower annealing temperature or more amplification cycles can also change relative amplification product representation. These changes in materials and process did not improve the amount of SE33 amplification product in the 26-locus multiplex set described in Example 1 and displayed in FIG. 1. Dye investigation in Example 7 revealed to us that use of the ATTO488 dye provided relatively stronger representation of amplification products than use of the FAM dye. We re-labeled the labeled SE33 primer with ATTO488 in place of FAM and observed desirable stronger amplification product representation relative to other loci in the multiplex set.

Figure 13:
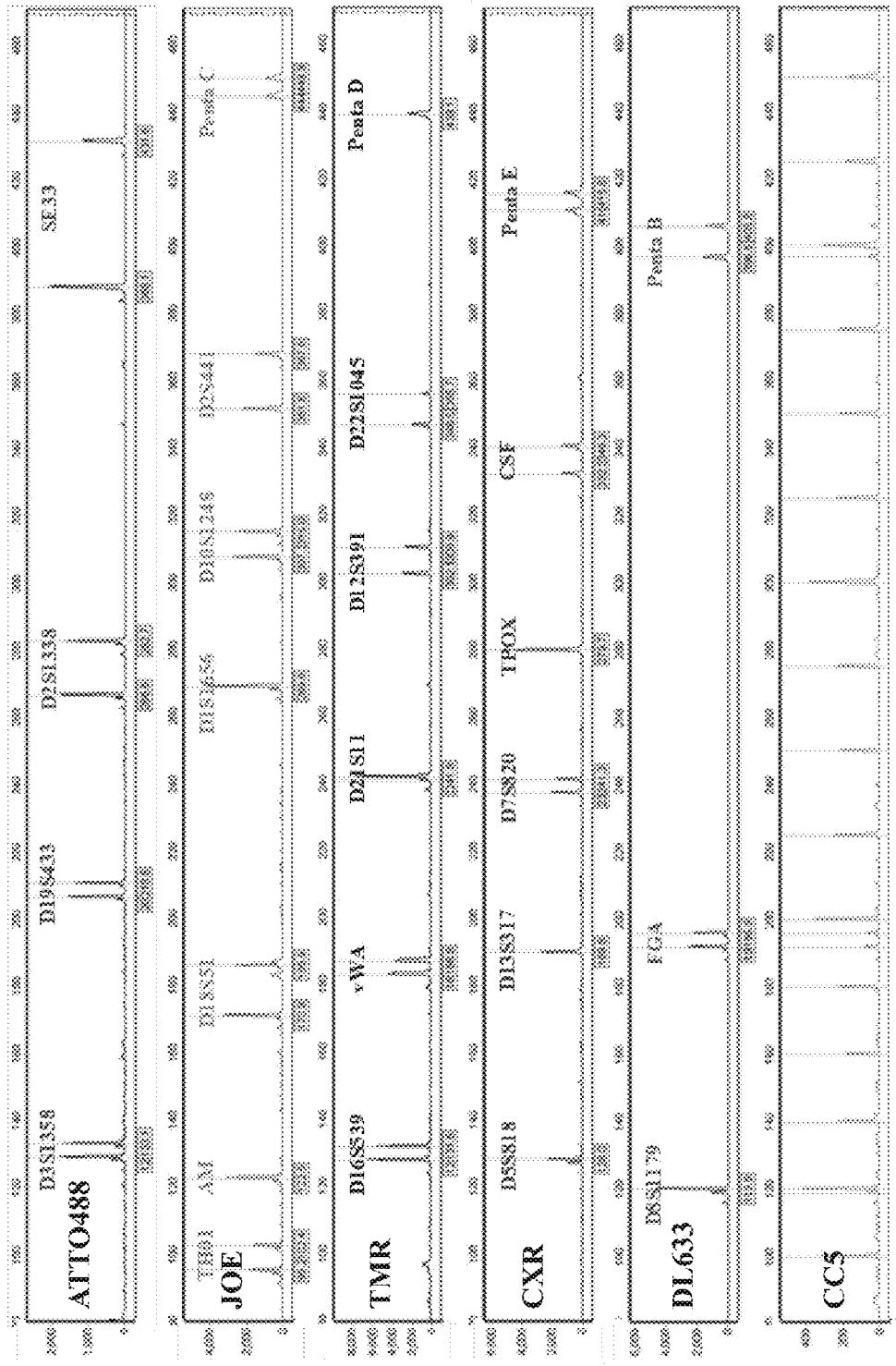
FIG. 13. illustrates a six-color 27-locus amplification product of male DNA separated and detected on the 6-/8-color instrument following development as described in the invention.

In FIG. 13, dyes employed to generate the amplification products displayed in each panel are indicated at the left end of the respective panel. This figure displays a 26-locus amplification that reveals strong SE33 amplification products. Compare the relative intensity of ATTO488-labeled SE33 amplification products of this amplification versus those observed in FIG. 1 with FAM-labeled SE33 products. Stronger representation derives from the more intense light emission detected from the ATTO488 dye. We also converted the labeled primers for D3S1358, D19S433, and D2S1338 from FAM-labeled to ATTO488-labeled to ensure spectral detection for these four loci remained consistent within the context of the multiplex dye set.

Example 13

Building and Combining Miniplexes as a Multiplex Development Strategy

Figure 14A:
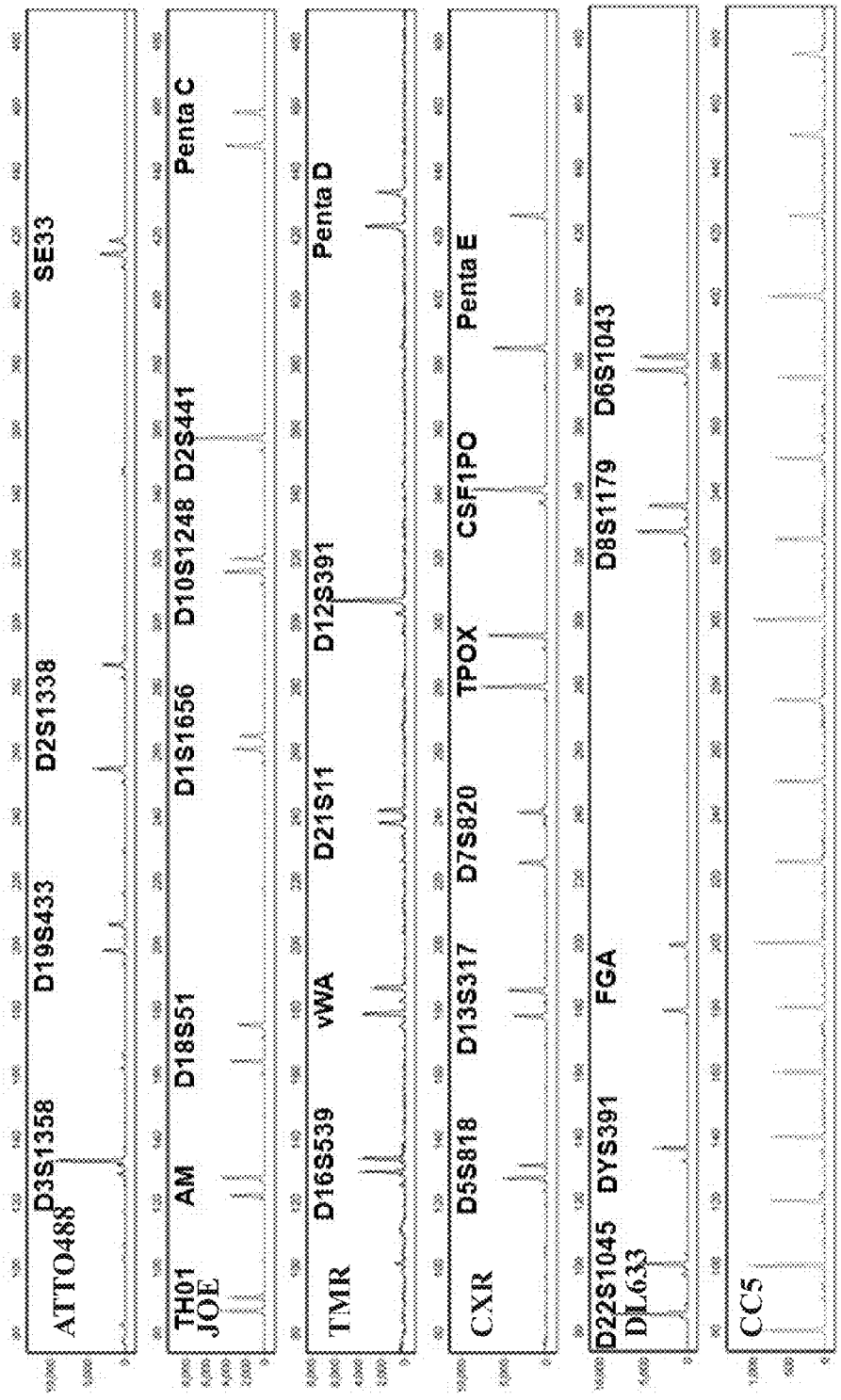
FIG. 14A. illustrates a six-color 27-locus amplification product of male DNA separated and detected on the 6-/8-color instrument.
Figure 14B:
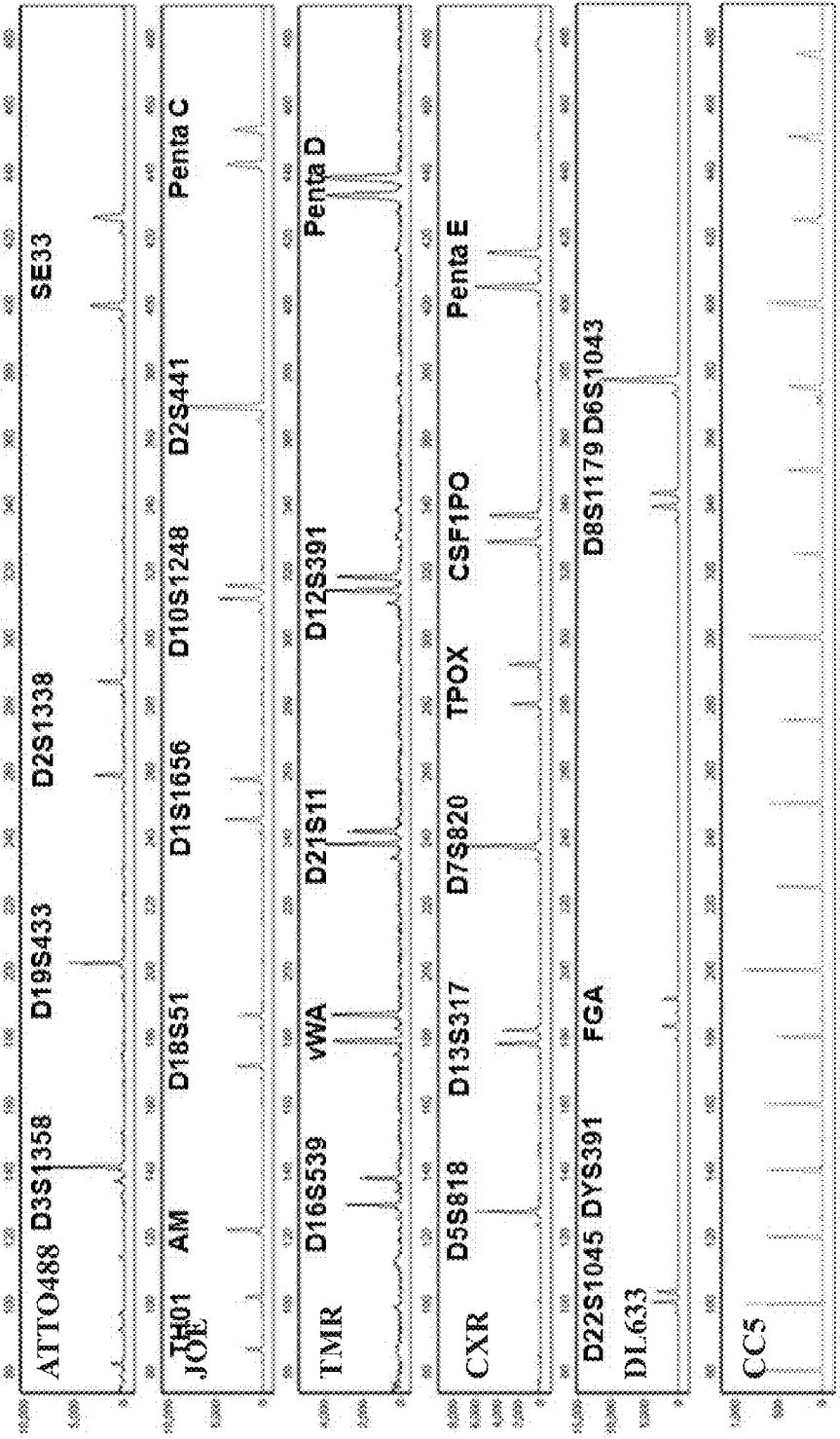
FIG. 14B. illustrates a six-color 27-locus amplification product of female DNA separated and detected on the 6-/8-color instrument.

Several miniplex sets were combined, each displaying successful amplification products for each individual locus and lacked nonspecific products or other primer sequence related artifacts to create a 19-locus multiplex. Three additional loci were added from another miniplex to create a 22-locus version and then added the remaining primer pairs individually. Each intermediate multiplex was tested to identify primer-related artifacts, evaluate locus-to-locus balance and confirm that amplified products of neighboring loci did not overlap. Contributing primers to each of many primer-related artifacts were identified by correlating presence and absence of particular artifacts with presence or absence of one primer from the full primer set. Offending primers were redesigned and retested to resolve most issues at these late developmental stages. Retesting included careful amplicon range size analysis of the empirical, not theoretical, results to ensure that alleles of neighboring loci of the same color did not overlap. Resizing with sequence additions to the 5' terminus of one or both primers was generally used to resolve cases of locus overlap. Locus-to-locus balance was adjusted using three different approaches: a) adjusting the input primer concentrations; b) adjusting the annealing temperature of the PCR amplification reaction, and c) primer redesign. Following these adjustments, FIG. 14A displays a 19.5-minute amplification of 2.8 ng of a male DNA sample employing a locus-balanced 27-locus multiplex set. FIG. 14B illustrates six-color 27-locus amplification of a female DNA sample. The amplified products were separated and detected using the 8-color optical system.

Example 14

Incorporating More Dyes Permits Smaller Amplification Products

Six-color detection or eight-color detection as an improvement over five-color detection permits improved design of multiplex systems for human identification purposes. One of the difficulties in working with human remains, for example, is that some samples contain degraded DNA. When this is the case, amplification of larger amplicons becomes more difficult or even impossible. The presence of six, seven, eight, nine, ten, eleven, twelve, fourteen, sixteen or more dyes enables redesign of a multiplex STR amplification set to generate smaller amplification products. This, in turn, will permit higher success rates in sample amplification.

FIG. 15A displays a 5-color design containing the 13 CODIS STR core loci in a multiplex set. It assumes the constraint of no amplification products below 70 bases and a requirement for 5 to 10 bases between adjacent loci to allow for a Substantially Non-overlapping STR Assay. The CODIS 13 STR loci constitute an STR Locus Size Range Sum of 689 bases. Given the constraints of the locus size range of the selected loci, and the requirement to reserve one color for the size marker, an average of 3.25 loci/color can be designed into each color leaving the a Multiplex Size Range of 235 bases and Multiplex Density of 2.93.

FIG. 15B displays a 6-color design containing the same loci with the same constraints as the 5-color design in FIG. 15A. With the inclusion of a sixth dye, the upper size limit for the multiplex set is approximately 275 bases. In addition, the average loci/color is 2.6 and the lower number of loci in each color makes it easier to avoid the potential for locus-to locus overlap of alleles to allow for a Substantially Non-overlapping STR Assay. The Multiplex Size Range is 205 bases and the Multiplex Density is 3.36.

FIG. 15C displays an 8-color design containing the same loci with the same constraints as the 5-color design in FIG. 15A and the 6-color design in FIG. 15B. With the inclusion of eight dyes, the upper size limit for the multiplex set is approximately 230 bases. Furthermore, the large alleles of the FGA locus are extremely rare, so more common alleles do not exceed 155 bases. This substantial diminution in allele sizes substantially increases the ability to obtain full profiles with degraded samples. In addition, 1.86 is the average loci/color and the lower number of loci in each color makes it easier to avoid the potential for locus-to locus overlap of alleles to allow for a Substantially Non-overlapping STR Assay. In fact, with only two loci or fewer in each color and only six neighbor-to-neighbor locus pairs in the multiplex set, increased spacing between the locus pairs in the same color make it possible to avoid this risk completely as shown in FIG. 15C. The Multiplex Size Range in this format, including the extremely rare high molecular weight FGA alleles, is 160 bases and the Multiplex Density is 4.31.

The Multiplex Content, STR Locus Size Range Sum, Multiplex Size Range, and Multiplex Density for the three versions of a 13-STR CODIS Core multiplex set are compared in Table 7.

TABLE 7

Comparison of 13-STR CODIS Core Loci in Multiplex Sets

| Multiplex Content | STR Locus Size Range Sum | Multiplex Size Range | Multiplex Density |
|---|---|---|---|
| 13 Loci - 5 Dyes | 689 | 235 | 2.93 |
| 13 Loci - 6 Dyes | 689 | 205 | 3.36 |
| 13 Loci - 8 Dyes | 689 | 160 | 4.31 |

Example 15

24-Locus 23-STR Formal Locus Multiplex

Multiplex designs with increased Multiplex Density provide greater efficiency in multiplex amplification assays. This approach permits evaluation of more alternate forms of polymorphic loci in smaller size ranges. In turn, this permits increased information to be obtained and stronger inferences to be made from the obtained information.

FIG. 16 display a means for simultaneous co-amplification of the amelogenin locus plus the following 23 STR loci: D3S1358, SE33, D6S1043, TH01, D18S51, D1S1656, D19S433, D2S441, D16S539, vWA, D21S11, D12S391, CSF1PO, D5S818, D13S317, D7S820, TPOX, D2S1138, D22S1045, DYS391, FGA, D8S1179, and D10S1248. The STR Locus Size Range Sum of this multiplex design is 1286, the Multiplex Size Range is 340 bases, and the Multiplex Density is 3.78.

Example 16

23-Locus 22-STR Formal Locus Multiplex

Multiplex designs with increased Multiplex Density provide greater efficiency in multiplex amplification assays. This approach permits evaluation of more alternate forms of polymorphic loci in smaller size ranges. In turn, this permits increased information to be obtained and stronger inferences to be made from the obtained information.

FIG. 17 display a means for simultaneous co-amplification of the amelogenin locus plus the following 23 STR loci: D3S1358, D6S1043, TH01, D18S51, D1S1656, D19S433, D2S441, D16S539, vWA, D21S11, D12S391, CSF1PO, D5S818, D13S317, D7S820, TPOX, D2S1138, D22S1045, DYS391, FGA, D8S1179, and D10S1248. The STR Locus Size Range Sum of this multiplex design is 1136, the Multiplex Size Range is 300 bases, and the Multiplex Density is 3.79.

Example 17

22-Locus 21-STR Formal Locus Multiplex

Multiplex designs with increased Multiplex Density provide greater efficiency in multiplex amplification assays. This approach permits evaluation of more alternate forms of polymorphic loci in smaller size ranges. In turn, this permits increased information to be obtained and stronger inferences to be made from the obtained information.

FIG. 18 display a means for simultaneous co-amplification of the amelogenin locus plus the following 23 STR loci: D3S1358, TH01, D18S51, D1S1656, D19S433, D2S441, D16S539, vWA, D21S11, D12S391, CSF1PO, D5S818, D13S317, D7S820, TPOX, D2S1138, D22S1045, DYS391, FGA, D8S1179, and D10S1248. The STR Locus Size Range Sum of this multiplex design is 1072, the Multiplex Size Range is 292 bases, and the Multiplex Density is 3.67.

Example 18

21-Locus 20-STR Formal Locus Multiplex

Multiplex designs with increased Multiplex Density provide greater efficiency in multiplex amplification assays. This approach permits evaluation of more alternate forms of polymorphic loci in smaller size ranges. In turn, this permits increased information to be obtained and stronger inferences to be made from the obtained information.

FIG. 19 display a means for simultaneous co-amplification of the amelogenin locus plus the following 23 STR loci: D3S1358, TH01, D18S51, D1S1656, D19S433, D2S441, D16S539, vWA, D21S11, D12S391, CSF1PO, D5S818, D13S317, D7S820, TPOX, D2S1138, D22S1045, FGA, D8S1179, and D10S1248. The STR Locus Size Range Sum of this multiplex design is 1044, the Multiplex Size Range is 278 bases, and the Multiplex Density is 3.76.

Example 19

Six-Color SNP Assay

Detection with more than six, seven, eight, nine, ten, eleven, twelve, fourteen, sixteen, or twenty-four color detection also improves non-STR evaluations, such as SNP testing, by permitting improved design of multiplex systems for human and veterinary identification, clinical and veterinary diagnostic, biothreat detection, food safety, and industrial testing purposes, among others. In particular, smaller products are distinguished with more dyes as demonstrated, above, for STR multiplex assays. Alternately, more loci can be tested within the same size range constraints when more dyes are used. In general, the greater the number of dyes, the more information can be gained from a single sample and single detection lane.

In this example, we describe the use of 6-dye capabilities to assay 6 SNPs to determine iris color in humans. Previously, an assay published by Walsh (Walsh et al. (2011, Iris IrisPlex: A sensitive DNA tool for accurate prediction of blue and brown eye color in the absence of ancestry information. Forensic Science International: Genetics 5: 170-180) was based on amplification of 6 regions of human sample DNA followed by a single base extension assay (Chen et al. 3003, Single nucleotide polymorphism genotyping: biochemistry, protocol, cost, and throughput, The Pharmacogenomics Journal 3: 77-96) to interrogate the presence of one individual base within each of the amplified PCR products. That test was performed as a 5-dye assay with one of the five colors reserved for a size marker. The two potential alternate SNP products for each of the 6 locations of interest, i.e. twelve potential products, are all detected in 4 colors with product sizes ranging from 24 to 54 bases. With the six dye approach of the instant invention, the single base extension product range can be reduced, for example, to 48 bases. The difficulty in preparing and purifying longer oligonucleotides required to detect longer products in single base extension assays demonstrates the advantage of creating assays dependent on shorter oligonucleotides as proposed here.

In an extension of this approach, many SNP assays require more than 10, more than 20, more than 30, more than 50, more than 100, more than 200, more than 300, more than 400, more than 500, more than 1000, more than 2000, more than 300, or more than 5000 individual SNPs to be interrogated in a single reaction and detection lane. The inclusion of a 6-color system, 8-color system, or more-color system in the assay permits many more SNP assays to be performed in the same size ranges as current 5-color assays.

Samples used in SNP analysis can include amplified or unamplified nucleic acids in the sample, including products amplified by PCR. The analyses include but are not limited to electrophoretic separation and detection as well as microarray-based assays. Six or more fluorescent labels can be attached to oligonucleotides prior to, or following exposure, to at least three SNP polymorphisms. For example, the oligonucleotides can be labeled prior to their use in the method, or during the process of n a primer extension assay that incorporates the labels with the nucleotides.

Several alternate methods of SNP analysis can be improved through application of the invention. One method is to amplify a nucleic acid sample, then perform primer extension with unlabeled primers (oligonucleotides) in the presence of differentially labeled dideoxy-dNTPs (Syvanen, A-C et al. 1990. A primer-guided nucleotide incorporation assay in the genotypin of apolipoprotein E, Genomics 8: 684-692). Using different length unlabeled primers to perform the primer extension generates different length products. Using different dyes for detection adds dimensions to the detection process in the same way it does with amplified STR products. In a variation of the method, for example, mixtures of deoxy- and dideoxy-nucleotides can be incorporated.

Yet another alternate method involves allele specific hybridization employing the six or more, preferably eight or more, fluorescently labeled oligonucleotides. (Wallace 1979. Hybriciation of syntheit oligodeoxyribonucleotides to phi chi 174 DNA: the effect of single base pair mismatch, Nucleic Acides Research 10:3543-3557.)

Another implementation of the invention involves the use of PCR in the presence of one unlabeled primer, and two differentially labeled primers with identical (or nearly identical) sequence for each SNP being analyzed (Choi et al., 2012. Integrated allele-specific polymerase chain reaction-capillary electrophoresis microdevice for single nucleotide polymorphism genotyping. Biosens. Bioelectron. 35: 327-334.) Up to 4 differentially labeled primers can be used for each SNP location in rare cases. Separation and detection of these amplification products in the same fashion as STR locus products, that is by size separation or color distinction, Yet another implementation of the invention applied to SNP analyses involves sequence primer extension using a combination of polymerase, buffers, a mixture of deoxynucleotide triphosphates and dideoxynucleotide triphosphates in the presence of a nucleic acid target. During this process, amplification products from one nucleic acid target is labeled with four different fluorescent dyes attached to either the dNTPs or dideoxyNTPs (Sanger, Niclen, and Coulson, 1977. DNA sequencing with chain-terminating inhibitors, Proc Natl Acad Sci USA 74:5463-5467). In a separate location, a second nucleic acid target is labeled with yet four different dyes attached to either the dNTPs or dideoxyNTPs. The samples may be run separately, or in the version of the invention, mixed, then separated and detected for analysis.

The use of at least 6, 7, 8, 9, 10, 11, 12, 13, 14, 15, 16, 17, 18, 19, 20, 25, 30, 35, 40, 50 or more, fluorescent dyes can be applied to a large variety of SNP detection approaches (Chen and Sullivan, 2003, Single nucleotide polymorphism genotyping: biochemistry, protocol, cost, and throughput. The Pharmacogenomics Journal 3: 77-96; Syvänen, 2001, Accessing genetic variation: genotyping single nucleotide polymorphisms, Nature Reviews 2: 930-942; Kwok, 2000. High-throughput genotyping assay approaches, Pharmaco- genetics 1:1-5; Kwok, 2003 Detection of single nucleotide polymorphisms, Current Issues in Molecular Biology 5:43-60; Kim et al. SNP Genotyping: Technologies and Biomedical Applications Annual Review of Biomedical Engineering, Vol. 9: 289-320, 2007; Nassir et al. An ancestry informative marker set for determining continental origin: validation and extension using human genome diversity panels, BMC Genetics 2009, 10:39).

In combination with the electrophoretic separation and optical detection capabilities described herein, forensic, clinical, veterinary, food safety, and industrial microbiological samples, among others, can be interrogated for large numbers of SNPs. In combination with sequencing and multiplexed and other assays of the invention, SNP assays (including highly multiplexed SNP assays) can provide tremendous amounts of critical information. As desired, these SNP assays, alone or in combination, can be adapted to microfluidic biochips including fully integrated microfluidic biochip systems.

Example 20

Six-Color Assay for SNP Analysis Combined with STR Analysis

Example 2, Example 3, Example 5, Example 15, Example 16, Example 17, and Example 18 describe the use of six or more dyes to permit simultaneous amplification and analysis of an increasing number of autosomal STR loci, a larger Locus Size Range Sum analysis, and an increased Multiplex Density. Example 4 describes the use of six or more dyes to permit simultaneous amplification and analysis of an increasing number of autosomal STR loci combined with Y STR loci. Example 19 describes the use of six or more dyes to permit simultaneous amplification and analysis of an increasing number of SNP loci or to Multiplex Size Range requirement in SNP loci analyses.

The increased size range analysis permitted by the inclusion, detection, and color separation of six, seven, eight, ten, twelve, fourteen, twenty-four, or more dyes can also be used to simultaneously analyze different marker types. In particular, the amplification products of the SNP-based iris detection analysis described in Example 19 and the autosomal STR-based identification analysis described in Example 5 and several other Examples can be detected in the same single channel or lane of separated amplification products. Thus, the method can be used to determine identity and physical trait analysis simultaneously.

Multiplex amplification sets that combine different polymorphic marker types (e.g. STR, SNP, sequence variant), and different chromosome type sources (e.g. autosomal, X chromosome, Y chromosome, mitochondrial, bacterial, fungal, plant), and for different purposes (e.g. identity, kinship determination, forensics, physical traits, infectious disease cause, genetic characteristics) can be analyzed for the multiple marker types, multiple DNA sources, and multiple functional purposes simultaneously. Multiplex amplification sets of these types may also be combined with non-polymorphic nucleic acid markers that provide diagnostic information about presence, absence, identification, or condition of an organism or other nucleic acid-containing sample material.

Example 21

Dual Sequence Analyses

DNA sequence analysis is conducted to determine the order of four different nucleotides in the chromosomes that make up the human genome. While multiple methods of sequence analysis are available, a traditional and popular method is that developed by Sanger et al. (1977, DNA sequencing with chain-terminating inhibitors. PNAS 74: 5463-5467) that employs primer extension in the presence of a mixture of unlabeled deoxy-nucleotide triphosphates and fluorescently labeled dideoxy-nucleotide triphosphates. The four differentially fluorescently labeled dideoxy-nucleotide triphosphates terminate chain lengthening for each respective base and at various lengths that indicate the positions or the respective bases.

The use of 8-color detection permits the inclusion of two different non-overlapping dye color sets of Sanger sequenced products for detection and separate interpretation from a single lane of separated products. Thus we detect sequencing products from two sequencing reactions simultaneously in a single separation test. Furthermore, we are able to sequence two different DNA regions simultaneously using non-overlapping dye color sets of dideoxy-nucleotide triphosphates in a single reaction volume for subsequent separation, detection, and analysis of the separate sequences.

Increasing the number of colors by multiples of four proportionately increases the number of DNA sequences that can be analyzed on a single detection lane (e.g. 16 colors allows four sets of sequences). By judicious selection of dye number and assay requirements, a single sample can be used to gather an enormous amount of information. For example, a single human sample could provide identity and kinship information (e.g. using 6 colors and an STR assay), phenotypic information (e.g. using 6 additional colors and a SNP assay), and mitochondrial inheritance information (e.g. using 4 colors and a sequencing assay). Similarly, the approach can be used to perform human identification and kinship analysis (e.g. using 8 colors and an STR assay) and determination of pathogen identity and treatment regimen (e.g. using 8 colors and two multiplexed sequencing assays); this combination would be useful to assay a blood sample of an unidentified individual brought to an emergency room with signs of sepsis. In a third case, an assay may be used to provide identity information (e.g. using 6 colors and an STR assay), clinical diagnostic information related to tissue typing or cancer staging (e.g. using 4 additional colors and a sequencing assay); this combination would be useful to evaluate a tissue intraoperatively while providing assurance as to the identity of the tissue donor.

These applications are but three of an enormous number of combinations of assays that are enabled by the teachings of the invention. Assays that can be performed based on these teachings include individual and combination assays including but not limited to nucleic acid amplification (e.g. both singleplex and multiplex end-point PCR, Real-time PCR, reverse transcription PCR, asymmetric PCR, nested PCR, LATE PCR, touchdown PCR, digital PCR, rolling circle amplification, strand displacement amplification, and multiple displacement amplification); Y-STR amplification; mini-STR amplification; single nucleotide polymorphism analysis; VNTR analysis; RFLP analysis; nucleic acid sequencing (e.g. Sanger sequencing, pyrosequencing, and single molecule sequencing); reverse transcription; nucleic acid ligation; nucleic acid hybridization; immunoassays; binding assays; protein assays; enzymatic assays; mass spectroscopy; and nucleic acid and protein quantification.

The invention claimed is:

1. A method to detect the presence of single nucleotide polymorphisms (SNPs) of a nucleic acid in a sample containing the nucleic acid, comprising:
   (a) contacting in a solution said sample with at least eight unlabeled oligonucleotides under conditions permitting hybridization between said oligonucleotides and the nucleic acids in said sample;
   (b) generating primer extension products, each product labeled with one of at least eight different fluorescent dyes by primer extension reactions in the presence of ddNTPs, each ddNTP labeled with one of at least eight different fluorescent dyes; and
   (c) detecting the SNPs by detecting the primer extension products, each product labeled with one of at least eight different fluorescent dyes by laser-induced fluorescence using a galvanometer in a step and stare mode and a spectrograph to detect the fluorescence from each of said at least eight different fluorescent dyes.

2. A method to detect the presence of single nucleotide polymorphisms (SNPs) of a nucleic acid in a sample containing the nucleic acid, comprising:
   (a) contacting in a solution said sample with at least eight oligonucleotides, each labeled with a different fluorescent dye, under conditions permitting hybridization between said oligonucleotides and the nucleic acid in said sample; and
   (b) detecting the SNPs by detecting the hybridization products, each product labeled with one of at least eight different fluorescent dyes by laser-induced fluorescence using a galvanometer in a step and stare mode and a spectrograph to detect the fluorescence from each of said at least eight different fluorescent dyes.

* * * * *

```
                          SEQUENCE LISTING

<160> NUMBER OF SEQ ID NOS: 52

<210> SEQ ID NO 1
<211> LENGTH: 19
<212> TYPE: DNA
<213> ORGANISM: Artificial
<220> FEATURE:
<223> OTHER INFORMATION: Synthetic Primers

<400> SEQUENCE: 1
ccctgggctc tgtaaagaa                                                    19

<210> SEQ ID NO 2
<211> LENGTH: 24
<212> TYPE: DNA
<213> ORGANISM: Artificial
<220> FEATURE:
<223> OTHER INFORMATION: Synthetic Primers

<400> SEQUENCE: 2
atcagagctt aaactgggaa gctg                                              24

<210> SEQ ID NO 3
<211> LENGTH: 24
<212> TYPE: DNA
<213> ORGANISM: Artificial
<220> FEATURE:
<223> OTHER INFORMATION: Synthetic Primers

<400> SEQUENCE: 3
ccggaggtaa aggtgtctta aagt                                              24
```

```
<210> SEQ ID NO 4
<211> LENGTH: 22
<212> TYPE: DNA
<213> ORGANISM: Artificial
<220> FEATURE:
<223> OTHER INFORMATION: Synthetic Primers

<400> SEQUENCE: 4
atttcctgtg tcagaccctg tt                                             22

<210> SEQ ID NO 5
<211> LENGTH: 19
<212> TYPE: DNA
<213> ORGANISM: Artificial
<220> FEATURE:
<223> OTHER INFORMATION: Synthetic Primers

<400> SEQUENCE: 5
gcgcctggtc tttgtttat                                                 19

<210> SEQ ID NO 6
<211> LENGTH: 25
<212> TYPE: DNA
<213> ORGANISM: Artificial
<220> FEATURE:
<223> OTHER INFORMATION: Synthetic Primers

<400> SEQUENCE: 6
agaaaatccc catataagtt caagc                                          25

<210> SEQ ID NO 7
<211> LENGTH: 22
<212> TYPE: DNA
<213> ORGANISM: Artificial
<220> FEATURE:
<223> OTHER INFORMATION: Synthetic Primers

<400> SEQUENCE: 7
caaaaccctg aaaatggcaa tt                                             22

<210> SEQ ID NO 8
<211> LENGTH: 20
<212> TYPE: DNA
<213> ORGANISM: Artificial
<220> FEATURE:
<223> OTHER INFORMATION: Synthetic Primers

<400> SEQUENCE: 8
agtgttcatg cctacatccc                                                20

<210> SEQ ID NO 9
<211> LENGTH: 22
<212> TYPE: DNA
<213> ORGANISM: Artificial
<220> FEATURE:
<223> OTHER INFORMATION: Synthetic Primers

<400> SEQUENCE: 9
cttcctccag ggtattaatg gg                                             22

<210> SEQ ID NO 10
<211> LENGTH: 24
<212> TYPE: DNA
<213> ORGANISM: Artificial
<220> FEATURE:
<223> OTHER INFORMATION: Synthetic Primers
```

<400> SEQUENCE: 10
acatcacaaa aatcttcact ctcc                                              24

<210> SEQ ID NO 11
<211> LENGTH: 18
<212> TYPE: DNA
<213> ORGANISM: Artificial
<220> FEATURE:
<223> OTHER INFORMATION: Synthetic Primers

<400> SEQUENCE: 11
ccccactgca gtccaatc                                                     18

<210> SEQ ID NO 12
<211> LENGTH: 20
<212> TYPE: DNA
<213> ORGANISM: Artificial
<220> FEATURE:
<223> OTHER INFORMATION: Synthetic Primers

<400> SEQUENCE: 12
aatcaacaga ggcttgcatg                                                   20

<210> SEQ ID NO 13
<211> LENGTH: 23
<212> TYPE: DNA
<213> ORGANISM: Artificial
<220> FEATURE:
<223> OTHER INFORMATION: Synthetic Primers

<400> SEQUENCE: 13
ggtgattttc ctctttggta tcc                                               23

<210> SEQ ID NO 14
<211> LENGTH: 31
<212> TYPE: DNA
<213> ORGANISM: Artificial
<220> FEATURE:
<223> OTHER INFORMATION: Synthetic Primers

<400> SEQUENCE: 14
agtttacaac atttgtatct ttatctgtat c                                      31

<210> SEQ ID NO 15
<211> LENGTH: 21
<212> TYPE: DNA
<213> ORGANISM: Artificial
<220> FEATURE:
<223> OTHER INFORMATION: Synthetic Primers

<400> SEQUENCE: 15
atgttggtca ggctgactat g                                                 21

<210> SEQ ID NO 16
<211> LENGTH: 24
<212> TYPE: DNA
<213> ORGANISM: Artificial
<220> FEATURE:
<223> OTHER INFORMATION: Synthetic Primers

<400> SEQUENCE: 16
gattccacat ttatcctcat tgac                                              24

<210> SEQ ID NO 17
<211> LENGTH: 28

```
<212> TYPE: DNA
<213> ORGANISM: Artificial
<220> FEATURE:
<223> OTHER INFORMATION: Synthetic Primers

<400> SEQUENCE: 17
gtatttcatg tgtacattcg tatctatc                                    28

<210> SEQ ID NO 18
<211> LENGTH: 27
<212> TYPE: DNA
<213> ORGANISM: Artificial
<220> FEATURE:
<223> OTHER INFORMATION: Synthetic Primers

<400> SEQUENCE: 18
gccttaattt atttacctat cctgtag                                     27

<210> SEQ ID NO 19
<211> LENGTH: 21
<212> TYPE: DNA
<213> ORGANISM: Artificial
<220> FEATURE:
<223> OTHER INFORMATION: Synthetic Primers

<400> SEQUENCE: 19
aaagcaaacc tgagcattag c                                           21

<210> SEQ ID NO 20
<211> LENGTH: 23
<212> TYPE: DNA
<213> ORGANISM: Artificial
<220> FEATURE:
<223> OTHER INFORMATION: Synthetic Primers

<400> SEQUENCE: 20
gtgagaaacc atacttttc cct                                          23

<210> SEQ ID NO 21
<211> LENGTH: 23
<212> TYPE: DNA
<213> ORGANISM: Artificial
<220> FEATURE:
<223> OTHER INFORMATION: Synthetic Primers

<400> SEQUENCE: 21
ctggtgaagg aagaaaagag aat                                         23

<210> SEQ ID NO 22
<211> LENGTH: 22
<212> TYPE: DNA
<213> ORGANISM: Artificial
<220> FEATURE:
<223> OTHER INFORMATION: Synthetic Primers

<400> SEQUENCE: 22 ttggcttta gacctggact ga                                           22

<210> SEQ ID NO 23
<211> LENGTH: 26
<212> TYPE: DNA
<213> ORGANISM: Artificial
<220> FEATURE:
<223> OTHER INFORMATION: Synthetic Primers

<400> SEQUENCE: 23
```

-continued

```
attacagaag tctgggatgt ggagga                                              26

<210> SEQ ID NO 24
<211> LENGTH: 19
<212> TYPE: DNA
<213> ORGANISM: Artificial
<220> FEATURE:
<223> OTHER INFORMATION: Synthetic Primers

<400> SEQUENCE: 24
ggcagcccaa aaagacaga                                                      19

<210> SEQ ID NO 25
<211> LENGTH: 27
<212> TYPE: DNA
<213> ORGANISM: Artificial
<220> FEATURE:
<223> OTHER INFORMATION: Synthetic Primers

<400> SEQUENCE: 25
tcaatacaga cagacagaca ggtggat                                             27

<210> SEQ ID NO 26
<211> LENGTH: 29
<212> TYPE: DNA
<213> ORGANISM: Artificial
<220> FEATURE:
<223> OTHER INFORMATION: Synthetic Primers

<400> SEQUENCE: 26
gtttgtgtgt gcatctgtaa gcatgtatc                                           29

<210> SEQ ID NO 27
<211> LENGTH: 22
<212> TYPE: DNA
<213> ORGANISM: Artificial
<220> FEATURE:
<223> OTHER INFORMATION: Synthetic Primers

<400> SEQUENCE: 27
cacttcactc tgagtgacaa at                                                  22

<210> SEQ ID NO 28
<211> LENGTH: 27
<212> TYPE: DNA
<213> ORGANISM: Artificial
<220> FEATURE:
<223> OTHER INFORMATION: Synthetic Primers

<400> SEQUENCE: 28
tctggtgtgt ggagatgtct tacaata                                             27

<210> SEQ ID NO 29
<211> LENGTH: 24
<212> TYPE: DNA
<213> ORGANISM: Artificial
<220> FEATURE:
<223> OTHER INFORMATION: Synthetic Primers

<400> SEQUENCE: 29
gcaaaaagct ataattgtac cact                                                24

<210> SEQ ID NO 30
<211> LENGTH: 27
<212> TYPE: DNA
<213> ORGANISM: Artificial
```

```
<220> FEATURE:
<223> OTHER INFORMATION: Synthetic Primers

<400> SEQUENCE: 30
agttctttag cagtgatttc tgatatt                                              27

<210> SEQ ID NO 31
<211> LENGTH: 22
<212> TYPE: DNA
<213> ORGANISM: Artificial
<220> FEATURE:
<223> OTHER INFORMATION: Synthetic Primers

<400> SEQUENCE: 31
atatgtgagt caattcccca ag                                                   22

<210> SEQ ID NO 32
<211> LENGTH: 26
<212> TYPE: DNA
<213> ORGANISM: Artificial
<220> FEATURE:
<223> OTHER INFORMATION: Synthetic Primers

<400> SEQUENCE: 32
tgtattagtc aatgttctcc agagac                                               26

<210> SEQ ID NO 33
<211> LENGTH: 22
<212> TYPE: DNA
<213> ORGANISM: Artificial
<220> FEATURE:
<223> OTHER INFORMATION: Synthetic Primers

<400> SEQUENCE: 33
atcgttggaa ttccccaaac tg                                                   22

<210> SEQ ID NO 34
<211> LENGTH: 21
<212> TYPE: DNA
<213> ORGANISM: Artificial
<220> FEATURE:
<223> OTHER INFORMATION: Synthetic Primers

<400> SEQUENCE: 34
gtgacctcag gcaagtccct a                                                    21

<210> SEQ ID NO 35
<211> LENGTH: 26
<212> TYPE: DNA
<213> ORGANISM: Artificial
<220> FEATURE:
<223> OTHER INFORMATION: Synthetic Primers

<400> SEQUENCE: 35
ccataggttt tgaactcaca gattaa                                               26

<210> SEQ ID NO 36
<211> LENGTH: 22
<212> TYPE: DNA
<213> ORGANISM: Artificial
<220> FEATURE:
<223> OTHER INFORMATION: Synthetic Primers

<400> SEQUENCE: 36
gccagcaaaa aagaaaggaa ga                                                   22
```

```
<210> SEQ ID NO 37
<211> LENGTH: 23
<212> TYPE: DNA
<213> ORGANISM: Artificial
<220> FEATURE:
<223> OTHER INFORMATION: Synthetic Primers

<400> SEQUENCE: 37
cttgaagctg ggagacggaa agt                                          23

<210> SEQ ID NO 38
<211> LENGTH: 22
<212> TYPE: DNA
<213> ORGANISM: Artificial
<220> FEATURE:
<223> OTHER INFORMATION: Synthetic Primers

<400> SEQUENCE: 38
agctctctta ctttgggtgg gc                                           22

<210> SEQ ID NO 39
<211> LENGTH: 22
<212> TYPE: DNA
<213> ORGANISM: Artificial
<220> FEATURE:
<223> OTHER INFORMATION: Synthetic Primers

<400> SEQUENCE: 39
cttgcaggag acagggttta ta                                           22

<210> SEQ ID NO 40
<211> LENGTH: 19
<212> TYPE: DNA
<213> ORGANISM: Artificial
<220> FEATURE:
<223> OTHER INFORMATION: Synthetic Primers

<400> SEQUENCE: 40
cgccactgct acaagagag                                               19

<210> SEQ ID NO 41
<211> LENGTH: 21
<212> TYPE: DNA
<213> ORGANISM: Artificial
<220> FEATURE:
<223> OTHER INFORMATION: Synthetic Primers

<400> SEQUENCE: 41
gtgaggctga agtaggatca c                                            21

<210> SEQ ID NO 42
<211> LENGTH: 26
<212> TYPE: DNA
<213> ORGANISM: Artificial
<220> FEATURE:
<223> OTHER INFORMATION: Synthetic Primers

<400> SEQUENCE: 42
gacacaagtc cttttttaga tatgtg                                       26

<210> SEQ ID NO 43
<211> LENGTH: 20
<212> TYPE: DNA
<213> ORGANISM: Artificial
<220> FEATURE:
<223> OTHER INFORMATION: Synthetic Primers
```

```
<400> SEQUENCE: 43
gggcgactga gcaagactca                                              20

<210> SEQ ID NO 44
<211> LENGTH: 28
<212> TYPE: DNA
<213> ORGANISM: Artificial
<220> FEATURE:
<223> OTHER INFORMATION: Synthetic Primers

<400> SEQUENCE: 44
gacatttctt attttctcat attggtgg                                     28

<210> SEQ ID NO 45
<211> LENGTH: 21
<212> TYPE: DNA
<213> ORGANISM: Artificial
<220> FEATURE:
<223> OTHER INFORMATION: Synthetic Primers

<400> SEQUENCE: 45
tctgtaattc cagctcctag g                                            21

<210> SEQ ID NO 46
<211> LENGTH: 29
<212> TYPE: DNA
<213> ORGANISM: Artificial
<220> FEATURE:
<223> OTHER INFORMATION: Synthetic Primers

<400> SEQUENCE: 46
aggtttatat atatttctac aacatctcc                                    29

<210> SEQ ID NO 47
<211> LENGTH: 22
<212> TYPE: DNA
<213> ORGANISM: Artificial
<220> FEATURE:
<223> OTHER INFORMATION: Synthetic Primers

<400> SEQUENCE: 47
ggcctgttcc tcccttattt cc                                           22

<210> SEQ ID NO 48
<211> LENGTH: 20
<212> TYPE: DNA
<213> ORGANISM: Artificial
<220> FEATURE:
<223> OTHER INFORMATION: Synthetic Primers

<400> SEQUENCE: 48
gagtgcaggt cacagggaac                                              20

<210> SEQ ID NO 49
<211> LENGTH: 20
<212> TYPE: DNA
<213> ORGANISM: Artificial
<220> FEATURE:
<223> OTHER INFORMATION: Synthetic Primers

<400> SEQUENCE: 49
gcacagaaca ggcacttagg                                              20

<210> SEQ ID NO 50
```

```
<211> LENGTH: 24
<212> TYPE: DNA
<213> ORGANISM: Artificial
<220> FEATURE:
<223> OTHER INFORMATION: Synthetic Primers

<400> SEQUENCE: 50
ccccaacgct caaacgtgag gttg                                              24

<210> SEQ ID NO 51
<211> LENGTH: 20
<212> TYPE: DNA
<213> ORGANISM: Artificial
<220> FEATURE:
<223> OTHER INFORMATION: Synthetic Primers

<400> SEQUENCE: 51
tccaagttga cttggctgag                                                   20

<210> SEQ ID NO 52
<211> LENGTH: 26
<212> TYPE: DNA
<213> ORGANISM: Artificial
<220> FEATURE:
<223> OTHER INFORMATION: Synthetic Primers

<400> SEQUENCE: 52
cagatgataa atacatagga tggatg                                            26
```